US012760015B2

(12) United States Patent
Yao et al.

(10) Patent No.: US 12,760,015 B2
(45) Date of Patent: Oct. 13, 2026

(54) CRYSTAL OF PDE3/PDE4 DUAL INHIBITOR AND USE THEREOF

(71) Applicant: Chia Tai Tianqing Pharmaceutical Group Co., Ltd., Lianyungang City (CN)

(72) Inventors: Wenjun Yao, Shanghai (CN); Yunfu Luo, Shanghai (CN); Peng Zhang, Shanghai (CN); Ting Yao, Shanghai (CN)

(73) Assignee: Chia Tai Tianqing Pharmaceutical Group Co., Ltd., Lianyungang City (CN)

( * ) Notice: Subject to any disclaimer, the term of this patent is extended or adjusted under 35 U.S.C. 154(b) by 1090 days.

(21) Appl. No.: 17/792,192

(22) PCT Filed: Jan. 15, 2021

(86) PCT No.: PCT/CN2021/072151

§ 371 (c)(1),
(2) Date: Jul. 12, 2022

(87) PCT Pub. No.: WO2021/143843

PCT Pub. Date: Jul. 22, 2021

(65) Prior Publication Data

US 2023/0115817 A1 Apr. 13, 2023

(30) Foreign Application Priority Data

Jan. 15, 2020 (CN) ......................... 202010043882.5

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
See application file for complete search history.

(56) References Cited

U.S. PATENT DOCUMENTS

| | | | |
|---|---|---|---|
| 4,482,556 | A | 11/1984 | Lal |
| 4,581,172 | A | 4/1986 | Kaiser |
| 6,794,391 | B2 | 9/2004 | Oxford |
| 2021/0323960 | A1 | 10/2021 | Luo |

FOREIGN PATENT DOCUMENTS

| | | | | |
|---|---|---|---|---|
| CN | 1348453 A | 5/2002 | | |
| EP | 0 124 893 A2 | 11/1984 | | |
| WO | 0058308 A1 | 10/2000 | | |
| WO | WO-2020011254 A1 * | 1/2020 | ........... C07D 498/04 | |
| WO | WO-2021143841 A1 * | 7/2021 | ............... A61K 9/10 | |

OTHER PUBLICATIONS

Elder, D.P., et al., Journal of Pharmaceutical Sciences, 2010, 99(7), 2948-2961 (Year: 2010).*

Berge, S.M. et al., Journal of Pharmaceutical Sciences, 1977, 66(1), 1-19 (Year: 1977).*

Boswell-Smith et al. "The Pharmacology of Two Novel Long-Acting Phosphodiesterase 3/4 Inhibitors, RPL554 [9,10-Dimethoxy-2 (2, 4, 6-trimethylphenylimino)-3-(N-carbamoyl-2-aminoethyl)-3, 4, 6, 7-tetrahydro-2H-pyrimido [6, 1-a] isoquinolin-4-one] and RPL565 [6, 7-Dihydro-2-(2, 6-diisopropylphenoxy)-9, 10-dimethoxy-4H-pyrimido [6, 1-a] isoquinolin-4-one]." Journal of Pharmacology and Experimental Therapeutics 318.2 (2006) pp. 840-848.

Extended European Search Report issued in EP21740747 on Jan. 2, 2024.

International Search Report in International Patent Application No. PCT/CN2021/072151, mailed Apr. 15, 2021 (8 pages w/English translation).

* cited by examiner

*Primary Examiner* — Noble E Jarrell
*Assistant Examiner* — Sara Elizabeth Bell
(74) *Attorney, Agent, or Firm* — Nixon Peabody LLP

(57) ABSTRACT

Provided are a crystal of a tricyclic compound as shown in formula (I) or a pharmaceutically acceptable salt thereof and a preparation method therefor, and the use thereof in preparing a drug for treating PDE3- and/or PDE4-related diseases.

(I)

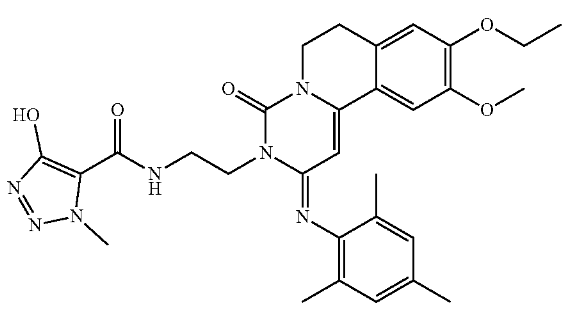

20 Claims, 20 Drawing Sheets

CRYSTAL OF PDE3/PDE4 DUAL INHIBITOR AND USE THEREOF

CROSS-REFERENCE TO RELATED APPLICATIONS

The present application is a U.S. National Stage Entry of International Application No. PCT/CN2021/072151 filed on Jan. 15, 2021, which claims the benefit and priority to Chinese Patent Application No. 202010043882.5 filed to China National Intellectual Property Administration on Jan. 15, 2020, which is incorporated herein by reference in their entireties.

TECHNICAL FIELD

The present application relates to a crystalline form of a PDE3/PDE4 dual inhibitor and use thereof in treating a disease associated with PDE3/PDE4, particularly chronic obstructive pulmonary disease (COPD).

BACKGROUND

Phosphodiesterases (PDEs) are a superfamily of enzyme systems including 11 members that participate in different signaling pathways and regulate different physiological processes. Among them, PDE3 is a major phosphodiesterase in human airway smooth muscle (ASM), and inhibition of PDE3 increases intracellular cAMP concentration and thus slackens bronchial smooth muscle. PDE4 plays a major regulatory role in the expression of proinflammatory and anti-inflammatory mediators, and a PDE4 inhibitor can inhibit the release of harmful mediators from inflammatory cells. Thus, in theory, an inhibitor that inhibits both PDE3 and PDE4 would have both the bronchodilation of a beta-adrenoreceptor agonist and the anti-inflammatory action of an inhaled glucocorticoid. The functional complementation of dual targeting is theoretically more effective than a sole targeting, providing a therapeutic effect which can be achieved only by a combination at present is achieved through a monotherapy and thus eliminating the defect that the physicochemical properties of the ingredients of medicaments used in a combination cannot be completely matched. In this way, the administration is simplified, and is convenient for a fixed dose regimen.

Victoria Boswell et al, *J. Pharmaco. Experi. Therap.*, 2006, 318:840-848 and WO200005830 reported that compounds RPL554 and RPL565 have long-acting bronchodilator and anti-inflammatory effect, as well as poor solubility, high plasma clearance and other physicochemical properties, and are suitable for inhalational administration. But the data also showed that the PDE4 inhibitory activity is unsatisfactory, and the anti-inflammatory effect is insufficient. Thus there's still a need for developing a compound having good PDE3/4 inhibitory activity. It is generally desirable for medicaments to have excellent properties in: pharmaceutical activity, pharmacokinetics, bioavailability, hygroscopicity, melting point, stability, solubility, purity, ease of preparation, etc., to meet the requirements of medicaments in terms of production, storage, formulation, etc. Thus there's still a need for developing a crystalline form of a compound having PDE3/4 inhibitory activity.

RPL554

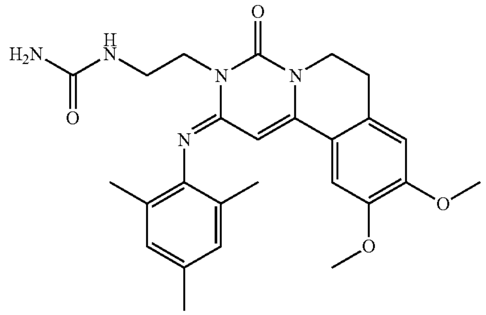

RPL565

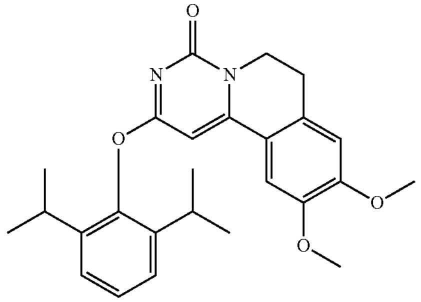

SUMMARY

In one aspect, the present application provides a crystalline form of a compound of formula (I) or a pharmaceutically acceptable salt thereof:

(I)

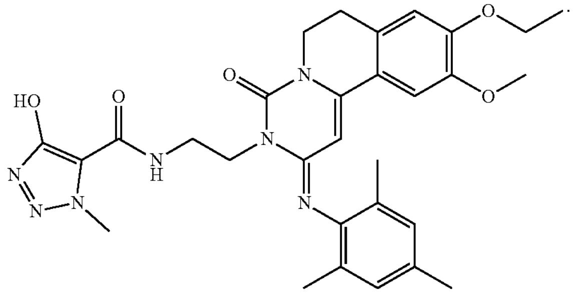

In some embodiments, the present application provides a crystalline form of the compound of formula (I).

In another aspect, the present application further provides a crystalline form A of the compound of formula (I) having diffraction peaks in an X-ray powder diffraction pattern using Cu Kα radiation at the following 2θ angles: 4.14±0.2°, 6.98±0.2°, 8.20±0.2° and 11.50±0.2°.

In some embodiments of the present application, the crystalline form A has diffraction peaks in an X-ray powder diffraction pattern using Cu Kα radiation at the following 2θ angles: 4.14±0.2°, 6.56±0.2°, 6.98±0.2°, 8.20±0.2°, 11.50±0.2°, 12.66±0.2°, 13.94±0.2° and 16.35±0.2°.

In some embodiments of the present application, the crystalline form A has diffraction peaks in an X-ray powder diffraction pattern using Cu Kα radiation at the following 2θ angles: 4.14±0.2°, 6.56±0.2°, 6.98±0.2°, 8.20±0.2°, 9.35±0.2°, 11.50±0.2°, 12.66±0.2°, 13.94±0.2°, 14.52±0.2°, 16.35±0.2°, 21.52±0.2° and 24.57±0.2°.

In some embodiments of the present application, the crystalline form A comprises 4, 5, 6, 7, 8, 9, 10, 11 or 12 diffraction peaks in an X-ray powder diffraction pattern using Cu Kα radiation selected from the following 2θ angles: 4.14±0.2°, 6.56±0.2°, 6.98±0.2°, 8.20±0.2°, 9.35±0.2°, 11.50±0.2°, 12.66±0.2°, 13.94±0.2°, 14.52±0.2°, 16.35±0.2°, 21.52±0.2° and 24.57±0.2°.

In some embodiments of the present application, the crystalline form A comprises 4, 5, 6, 7 or 8 diffraction peaks in an X-ray powder diffraction pattern using Cu Kα radiation selected from the following 2θ angles: 4.14±0.2°, 6.56±0.2°, 6.98±0.2°, 8.20±0.2°, 11.50±0.2°, 12.66±0.2°, 13.94±0.2° and 16.35±0.2°.

In some embodiments of the present application, the positions and relative intensities of diffraction peaks in the XRPD pattern using Cu Kα radiation of the crystalline form A described above are shown in Table 1 below:

TABLE 1

| No. | 2θ (±0.2°) | Relative intensity (%) |
|---|---|---|
| 1 | 4.14 | 34.6 |
| 2 | 6.56 | 56.0 |
| 3 | 6.98 | 100.0 |
| 4 | 8.20 | 60.0 |
| 5 | 9.35 | 27.1 |
| 6 | 11.50 | 73.0 |
| 7 | 12.66 | 27.2 |
| 8 | 13.94 | 41.8 |
| 9 | 14.52 | 12.3 |
| 10 | 16.05 | 4.5 |
| 11 | 16.35 | 41.1 |
| 12 | 18.87 | 7.7 |
| 13 | 19.80 | 10.4 |
| 14 | 20.67 | 10.3 |
| 15 | 21.52 | 16.4 |
| 16 | 21.93 | 4.0 |
| 17 | 22.33 | 4.0 |
| 18 | 22.91 | 8.2 |
| 19 | 23.94 | 9.5 |
| 20 | 24.57 | 14.0 |
| 21 | 25.16 | 7.5 |
| 22 | 27.75 | 9.0 |
| 23 | 29.17 | 7.2 |

In some embodiments of the present application, the crystalline form A has an XRPD pattern using Cu Kα radiation as shown in FIG. 1.

In some embodiments of the present application, the crystalline form A has endothermic peaks in a differential scanning calorimetry curve at 146.23±2° C. and/or 162.19±2° C.

In some embodiments of the present application, the crystalline form A has exothermic peaks in a differential scanning calorimetry curve at 172.65±2° C. and/or 241.73±2° C.

In some embodiments of the present application, the crystalline form A has endothermic peaks at 146.23±2° C. and 162.19±2° C. and exothermic peaks at 172.65±2° C. and 241.73±2° C. in a differential scanning calorimetry curve.

In some embodiments of the present application, the crystalline form A has a differential scanning calorimetry pattern as shown in FIG. 2.

In some embodiments of the present application, the crystalline form A has a weight loss of 0.4611% at 118.40±2° C., a weight loss of 0.8796% at 118.40±2° C. to 185.65±2° C., and a weight loss of 7.177% at 185.65±2° C. to 260.07±2° C. in a thermogravimetric analysis curve.

In some embodiments of the present application, the crystalline form A has a thermogravimetric analysis pattern as shown in FIG. 3.

In another aspect, the present application provides a method for preparing the crystalline form A comprising: precipitating a compound of formula (I) in a solvent of methanol.

In some embodiments, the procedure is conducted under a stirring condition at 40° C.

In another aspect, the present application further provides a crystalline form B of the compound of formula (I) having diffraction peaks in an X-ray powder diffraction pattern using Cu Kα radiation at the following 2θ angles: 5.81±0.2°, 13.96±0.2°, 15.01±0.2°, 17.95±0.2° and 24.73±0.2°.

In some embodiments of the present application, the crystalline form B has diffraction peaks in an X-ray powder diffraction pattern using Cu Kα radiation at the following 2θ angles: 5.81±0.2°, 8.38±0.2°, 11.16±0.2°, 13.96±0.2°, 14.47±0.2°, 15.01±0.2°, 17.95±0.2°, 24.73±0.2° and 26.13±0.2°.

In some embodiments of the present application, the crystalline form B has diffraction peaks in an X-ray powder diffraction pattern using Cu Kα radiation at the following 2θ angles: 5.81±0.2°, 8.38±0.2°, 11.16±0.2°, 13.96±0.2°, 14.47±0.2°, 15.01±0.2°, 16.76±0.2°, 17.95±0.2°, 20.83±0.2°, 24.73±0.2° and 26.13±0.2°.

In some embodiments of the present application, the crystalline form B has diffraction peaks in an X-ray powder diffraction pattern using Cu Kα radiation at the following 2θ angles: 5.81±0.2°, 8.38±0.2°, 9.13±0.2°, 11.16±0.2°, 11.60±0.2°, 12.82±0.2°, 13.96±0.2°, 14.47±0.2°, 15.01±0.2°, 16.76±0.2°, 17.95±0.2°, 18.91±0.2°, 20.83±0.2°, 24.36±0.2°, 24.73±0.2°, 25.78±0.2° and 26.13±0.2°.

In some embodiments of the present application, the crystalline form B comprises 5, 6, 7, 8, 9, 10, 11, 12 or more diffraction peaks in an X-ray powder diffraction pattern using Cu Kα radiation selected from the following 2θ angles: 5.81±0.2°, 8.38±0.2°, 9.13±0.2°, 11.16±0.2°, 11.60±0.2°, 12.82±0.2°, 13.96±0.2°, 14.47±0.2°, 15.01±0.2°, 16.76±0.2°, 17.95±0.2°, 18.91±0.2°, 20.83±0.2°, 24.36±0.2°, 24.73±0.2°, 25.78±0.2° and 26.13±0.2°.

In some embodiments of the present application, the crystalline form B comprises 5, 6, 7, 8, 9, 10 or 11 diffraction peaks in an X-ray powder diffraction pattern using Cu Kα radiation selected from the following 2θ angles: 5.81±0.2°, 8.38±0.2°, 11.16±0.2°, 13.96±0.2°, 14.47±0.2°, 15.01±0.2°, 16.76±0.2°, 17.95±0.2°, 20.83±0.2°, 24.73±0.2° and 26.13±0.2°.

In some embodiments of the present application, the crystalline form B comprises 5, 6, 7, 8 or 9 diffraction peaks in an X-ray powder diffraction pattern using Cu Kα radiation selected from the following 2θ angles: 5.81±0.2°, 8.38±0.2°, 11.16±0.2°, 13.96±0.2°, 14.47±0.2°, 15.01±0.2°, 17.95±0.2°, 24.73±0.2° and 26.13±0.2°.

In some embodiments of the present application, the positions and relative intensities of diffraction peaks in the XRPD pattern using Cu Kα radiation of the crystalline form B described above are shown in Table 2 below:

TABLE 2

| No. | 2θ (±0.2°) | Relative intensity (%) |
|---|---|---|
| 1 | 5.81 | 47.9 |
| 2 | 8.38 | 23.7 |

TABLE 2-continued

| No. | 2θ (±0.2°) | Relative intensity (%) |
|---|---|---|
| 3 | 9.13 | 15.4 |
| 4 | 10.57 | 8.2 |
| 5 | 11.16 | 46.9 |
| 6 | 11.60 | 17.6 |
| 7 | 11.77 | 6.2 |
| 8 | 12.82 | 16.5 |
| 9 | 13.96 | 99.5 |
| 10 | 14.47 | 38.4 |
| 11 | 15.01 | 80.7 |
| 12 | 15.71 | 8.0 |
| 13 | 16.03 | 9.1 |
| 14 | 16.54 | 9.2 |
| 15 | 16.76 | 24.4 |
| 16 | 17.47 | 8.3 |
| 17 | 17.69 | 20.9 |
| 18 | 17.95 | 69.7 |
| 19 | 18.91 | 15.0 |
| 20 | 20.21 | 8.0 |
| 21 | 20.83 | 24.3 |
| 22 | 21.25 | 5.3 |
| 23 | 22.96 | 9.9 |
| 24 | 24.14 | 5.1 |
| 25 | 24.36 | 19.5 |
| 26 | 24.73 | 100.0 |
| 27 | 25.48 | 11.1 |
| 28 | 25.78 | 19.9 |
| 29 | 26.13 | 61.8 |
| 30 | 29.05 | 12.5 |
| 31 | 29.37 | 6.3 |

In some embodiments of the present application, the crystalline form B has an XRPD pattern using Cu Kα radiation as shown in FIG. 4.

In some embodiments of the present application, the crystalline form B has exothermic peaks in a differential scanning calorimetry curve at 247.70±2° C.

In some embodiments of the present application, the crystalline form B has a differential scanning calorimetry pattern as shown in FIG. 5.

In some embodiments of the present application, the crystalline form B has a weight loss of 0.4870% at 155.75±2° C. and a weight loss of 7.287% at 155.75±2° C. to 262.18±2° C. in a thermogravimetric analysis curve.

In some embodiments of the present application, the crystalline form B has a thermogravimetric analysis pattern as shown in FIG. 6.

In another aspect, the present application provides a method for preparing the crystalline form B comprising: precipitating the compound of formula (I) in a mixed solvent of ethanol and water.

In some embodiments, the procedure is conducted under a stirring condition at 40° C.

In another aspect, the present application further provides a crystalline form C of the compound of formula (I) having diffraction peaks in an X-ray powder diffraction pattern using Cu Kα radiation at the following 2θ angles: 4.57±0.2°, 6.41±0.2°, 7.18±0.2° and 14.34±0.2°.

In some embodiments of the present application, the crystalline form C has diffraction peaks in an X-ray powder diffraction pattern using Cu Kα radiation at the following 2θ angles: 4.57±0.2°, 6.41±0.2°, 7.18±0.2°, 11.58±0.2°, 12.84±0.2°, 13.21±0.2°, 14.34±0.2°, 16.05±0.2° and 23.41±0.2°.

In some embodiments of the present application, the crystalline form C has diffraction peaks in an X-ray powder diffraction pattern using Cu Kα radiation at the following 2θ angles: 4.57±0.2°, 6.41±0.2°, 7.18±0.2°, 9.07±0.2°, 11.58±0.2°, 12.84±0.2°, 13.21±0.2°, 14.34±0.2°, 16.05±0.2°, 18.15±0.2°, 19.26±0.2°, 20.85±0.2° and 23.41±0.2°.

In some embodiments of the present application, the crystalline form C comprises 4, 5, 6, 7, 8, 9, 10, 11, 12 or 13 diffraction peaks in an X-ray powder diffraction pattern using Cu Kα radiation selected from the following 2θ angles: 4.57±0.2°, 6.41±0.2°, 7.18±0.2°, 9.07±0.2°, 11.58±0.2°, 12.84±0.2°, 13.21±0.2°, 14.34±0.2°, 16.05±0.2°, 18.15±0.2°, 19.26±0.2°, 20.85±0.2° and 23.41±0.2°.

In some embodiments of the present application, the crystalline form C comprises 4, 5, 6, 7, 8 or 9 diffraction peaks in an X-ray powder diffraction pattern using Cu Kα radiation selected from the following 2θ angles: 4.57±0.2°, 6.41±0.2°, 7.18±0.2°, 11.58±0.2°, 12.84±0.2°, 13.21±0.2°, 14.34±0.2°, 16.05±0.2° and 23.41±0.2°.

In some embodiments of the present application, the positions and relative intensities of diffraction peaks in the XRPD pattern using Cu Kα radiation of the crystalline form C described above are shown in Table 3 below:

TABLE 3

| No. | 2θ (±0.2°) | Relative intensity (%) |
|---|---|---|
| 1 | 4.57 | 38.7 |
| 2 | 6.41 | 39.3 |
| 3 | 7.18 | 100.0 |
| 4 | 9.07 | 12.4 |
| 5 | 10.15 | 6.3 |
| 6 | 11.18 | 3.9 |
| 7 | 11.58 | 31.3 |
| 8 | 12.84 | 36.7 |
| 9 | 13.21 | 29.3 |
| 10 | 13.98 | 7.1 |
| 11 | 14.34 | 70.9 |
| 12 | 16.05 | 39.6 |
| 13 | 18.15 | 9.6 |
| 14 | 18.68 | 6.8 |
| 15 | 19.26 | 11.8 |
| 16 | 19.76 | 5.4 |
| 17 | 20.10 | 6.7 |
| 18 | 20.85 | 10.4 |
| 19 | 22.74 | 5.6 |
| 20 | 23.41 | 25.7 |
| 21 | 25.14 | 5.1 |
| 22 | 25.82 | 6.8 |
| 23 | 28.82 | 6.2 |

In some embodiments of the present application, the crystalline form C has an XRPD pattern using Cu Kα radiation as shown in FIG. 7.

In some embodiments of the present application, the crystalline form C has exothermic peaks in a differential scanning calorimetry curve at 152.26±2° C. and/or 247.92±2° C.

In some embodiments of the present application, the crystalline form C has a differential scanning calorimetry pattern as shown in FIG. 8.

In some embodiments of the present application, the crystalline form C has a weight loss of 1.1460% at 152.80±2° C. and a weight loss of 7.871% at 152.80±2° C. to 262.77±2° C. in a thermogravimetric analysis curve.

In some embodiments of the present application, the crystalline form C has a thermogravimetric analysis pattern as shown in FIG. 9.

In another aspect, the present application provides a method for preparing the crystalline form C comprising: precipitating a compound of formula (I) in a solvent of acetonitrile.

In some embodiments, the procedure is conducted under a stirring condition at 40° C.

In another aspect, the present application provides a pharmaceutically acceptable salt of the compound of formula (I), wherein the pharmaceutically acceptable salt is sulfate, p-toluenesulfonate, methanesulfonate, or maleate.

In another aspect, the present application provides a crystalline form of the salt of the compound of formula (I).

In another aspect, the present application further provides sulfate of the compound of formula (I); in some embodiments, the sulfate of the compound of formula (I) is selected from a compound of formula (II), (II)

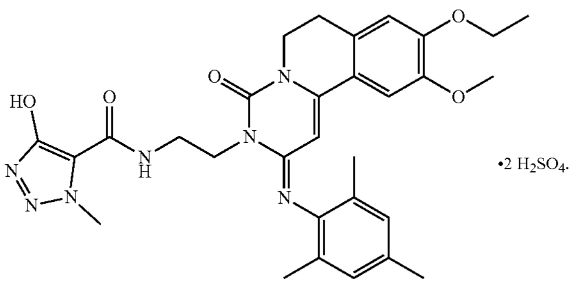

•2 $H_2SO_4$.

In another aspect, the present application further provides a crystalline form of the compound of formula (II) having diffraction peaks in an X-ray powder diffraction pattern using Cu Kα radiation at the following 2θ angles: 4.84±0.2°, 9.58±0.2°, 11.97±0.2° and 14.75±0.2°.

In some embodiments of the present application, the crystalline form of the compound of formula (II) has diffraction peaks in an X-ray powder diffraction pattern using Cu Kα radiation at the following 2θ angles: 4.84±0.2°, 9.58±0.2°, 10.93±0.2°, 11.97±0.2°, 14.31±0.2°, 14.75±0.2°, 16.49±0.2° and 24.42±0.2°.

In some embodiments of the present application, the crystalline form of the compound of formula (II) has diffraction peaks in an X-ray powder diffraction pattern using Cu Kα radiation at the following 2θ angles: 4.84±0.2°, 9.58±0.2°, 10.93±0.2°, 11.97±0.2°, 12.72±0.2°, 13.93±0.2°, 14.31±0.2°, 14.75±0.2°, 16.49±0.2°, 17.91±0.2°, 19.25±0.2°, 19.90±0.2°, 20.57±0.2°, 24.42±0.2° and 25.70±0.2°.

In some embodiments of the present application, the crystalline form of the compound of formula (II) comprises 4, 5, 6, 7, 8, 9, 10, 11, 12 or more diffraction peaks in an X-ray powder diffraction pattern using Cu Kα radiation selected from the following 2θ angles: 4.84±0.2°, 9.58±0.2°, 10.93±0.2°, 11.97±0.2°, 12.72±0.2°, 13.93±0.2°, 14.31±0.2°, 14.75±0.2°, 16.49±0.2°, 17.91±0.2°, 19.25±0.2°, 19.90±0.2°, 20.57±0.2°, 24.42±0.2° and 25.70±0.2°.

In some embodiments of the present application, the crystalline form of the compound of formula (II) comprises 4, 5, 6, 7 or 8 diffraction peaks in an X-ray powder diffraction pattern using Cu Kα radiation selected from the following 2θ angles: 4.84±0.2°, 9.58±0.2°, 10.93±0.2°, 11.97±0.2°, 14.31±0.2°, 14.75±0.2°, 16.49±0.2° and 24.42±0.2°.

In some embodiments of the present application, the crystalline form of the compound of formula (II) has diffraction peaks in an XRPD pattern using Cu Kα radiation with peak positions and relative intensities as shown in Table 4 below:

TABLE 4

| No. | 2θ (±0.2°) | Relative intensity |
|---|---|---|
| 1 | 4.84 | 88.1 |
| 2 | 7.42 | 4.7 |
| 3 | 9.58 | 76.3 |
| 4 | 10.26 | 5.6 |
| 5 | 10.93 | 26.6 |
| 6 | 11.97 | 90.1 |
| 7 | 12.72 | 13.6 |
| 8 | 13.93 | 15.1 |
| 9 | 14.31 | 24.4 |
| 10 | 14.75 | 100 |
| 11 | 16.49 | 20.9 |
| 12 | 17.91 | 17.2 |
| 13 | 18.44 | 8.7 |
| 14 | 19.25 | 10.5 |
| 15 | 19.90 | 18.8 |
| 16 | 20.57 | 10.7 |
| 17 | 21.21 | 4.2 |
| 18 | 22.50 | 9.3 |
| 19 | 22.97 | 5.2 |
| 20 | 23.57 | 5.1 |
| 21 | 24.42 | 39.4 |
| 22 | 24.39 | 6.2 |
| 23 | 25.70 | 10.5 |
| 24 | 27.31 | 7.7 |
| 25 | 27.70 | 4.5 |
| 26 | 29.42 | 8.8 |
| 27 | 32.23 | 4.8 |

In some embodiments of the present application, the crystalline form of the compound of formula (II) has an XRPD pattern using Cu Kα radiation as shown in FIG. 10.

In another aspect, the present application further provides p-toluenesulfonate of the compound of formula (I); in some embodiments, the p-toluenesulfonate of the compound of formula (I) is selected from a compound of formula (III), (III)

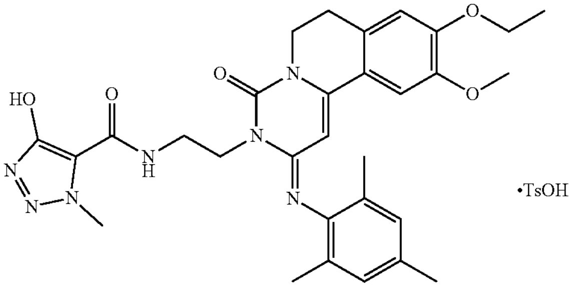

•TsOH

In another aspect, the present application further provides a crystalline form of the compound of formula (III) having diffraction peaks in an X-ray powder diffraction pattern using Cu Kα radiation at the following 2θ angles: 6.53±0.2°, 12.48±0.2° and 13.11±0.2°.

In some embodiments of the present application, the crystalline form of the compound of formula (III) has diffraction peaks in an X-ray powder diffraction pattern using Cu Kα radiation at the following 2θ angles: 6.53±0.2°, 10.87±0.2°, 12.48±0.2°, 13.11±0.2°, 16.58±0.2° and 25.03±0.2°.

In some embodiments of the present application, the crystalline form of the compound of formula (III) has diffraction peaks in the X-ray powder diffraction pattern using Cu Kα radiation at the following 2θ angles: 6.53±0.2°, 10.87±0.2°, 12.48±0.2°, 13.11±0.2°, 14.04±0.2°, 16.58±0.2°, 25.03±0.2°, 25.56±0.2° and 26.66±0.2°.

In some embodiments of the present application, the crystalline form of the compound of formula (III) comprises 3, 4, 5, 6, 7, 8 or 9 diffraction peaks in an X-ray powder diffraction pattern using Cu Kα radiation selected from the following 2θ angles: 6.53±0.2°, 10.87±0.2°, 12.48±0.2°, 13.11±0.2°, 14.04±0.2°, 16.58±0.2°, 25.03±0.2°, 25.56±0.2° and 26.66±0.2°.

In some embodiments of the present application, the crystalline form of the compound of formula (III) comprises 3, 4, 5 or 6 diffraction peaks in an X-ray powder diffraction pattern using Cu Kα radiation selected from the following 2θ angles: 6.53±0.2°, 10.87±0.2°, 12.48±0.2°, 13.11±0.2°, 16.58±0.2° and 25.03±0.2°.

In some embodiments of the present application, the crystalline form of the compound of formula (III) has diffraction peaks in an XRPD pattern using Cu Kα radiation with peak positions and relative intensities as shown in Table 5 below:

TABLE 5

| No. | 2θ (±0.2°) | Relative intensity (%) |
|---|---|---|
| 1 | 6.53 | 100 |
| 2 | 9.69 | 4.7 |
| 3 | 10.87 | 11.1 |
| 4 | 12.48 | 28.7 |
| 5 | 13.11 | 57.4 |
| 6 | 14.04 | 9.1 |
| 7 | 15.91 | 4.8 |
| 8 | 16.58 | 15.9 |
| 9 | 18.67 | 7.8 |
| 10 | 20.49 | 4.5 |
| 11 | 21.44 | 5.1 |
| 12 | 22.01 | 7.2 |
| 13 | 24.13 | 6.6 |
| 14 | 25.03 | 11.2 |
| 15 | 25.56 | 8.3 |
| 16 | 26.66 | 8.2 |
| 17 | 27.67 | 4.9 |
| 18 | 28.25 | 4.8 |

In some embodiments of the present application, the crystalline form of the compound of formula (III) has an XRPD pattern using Cu Kα radiation as shown in FIG. 11.

In some embodiments of the present application, the crystalline form of the compound of formula (III) has a weight loss of 1.785% at 148.23±2° C. and a weight loss of 5.790% at 148.23±2° C. to 240.99±2° C. in a thermogravimetric analysis curve.

In some embodiments of the present application, the crystalline form of the compound of formula (III) has a TGA pattern as shown in FIG. 12.

In another aspect, the present application further provides methanesulfonate of the compound of formula (I); in some embodiments, the methanesulfonate of the compound of formula (I) is selected from a compound of formula (IV), (IV)

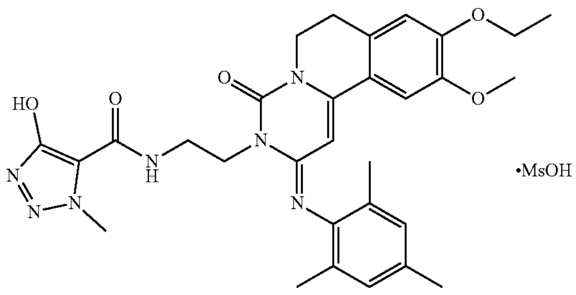

The present application further provides a crystalline form of the compound of formula (IV) having diffraction peaks in an X-ray powder diffraction pattern using Cu Kα radiation at the following 2θ angles: 11.22±0.2°, 18.85±0.2°, 22.62±0.2° and 24.45±0.2°.

In some embodiments of the present application, the crystalline form of the compound of formula (IV) has diffraction peaks in an X-ray powder diffraction pattern using Cu Kα radiation at the following 2θ angles: 11.22±0.2°, 12.58±0.2°, 16.43±0.2°, 17.90±0.2°, 18.85±0.2°, 22.62±0.2°, 24.45±0.2° and 25.87±0.2°.

In some embodiments of the present application, the crystalline form of the compound of formula (IV) has diffraction peaks in the X-ray powder diffraction pattern using Cu Kα radiation at the following 2θ angles: 11.22±0.2°, 12.58±0.2°, 16.43±0.2°, 17.08±0.2°, 17.90±0.2°, 18.85±0.2°, 19.23±0.2°, 19.72±0.2°, 22.62±0.2°, 23.27±0.2°, 24.45±0.2° and 25.87±0.2°.

In some embodiments of the present application, the crystalline form of the compound of formula (IV) has diffraction peaks in an X-ray powder diffraction pattern using Cu Kα radiation at the following 2θ angles: 11.22±0.2°, 12.58±0.2°, 13.88±0.2°, 15.49±0.2°, 16.04±0.2°, 16.43±0.2°, 17.08±0.2°, 17.90±0.2°, 18.54±0.2°, 18.85±0.2°, 19.23±0.2°, 19.72±0.2°, 20.02±0.2°, 20.51±0.2°, 22.62±0.2°, 23.27±0.2°, 24.45±0.2°, 24.83±0.2°, 25.42±0.2°, 25.87±0.2°, 26.09±0.2° and 29.53±0.2°.

In some embodiments of the present application, the crystalline form of the compound of formula (IV) comprises 4, 5, 6, 7, 8, 9, 10, 11, 12 or more diffraction peaks in an X-ray powder diffraction pattern using Cu Kα radiation selected from the following 2θ angles: 11.22±0.2°, 12.58±0.2°, 13.88±0.2°, 15.49±0.2°, 16.04±0.2°, 16.43±0.2°, 17.08±0.2°, 17.90±0.2°, 18.54±0.2°, 18.85±0.2°, 19.23±0.2°, 19.72±0.2°, 20.02±0.2°, 20.51±0.2°, 22.62±0.2°, 23.27±0.2°, 24.45±0.2°, 24.83±0.2°, 25.42±0.2°, 25.87±0.2°, 26.09±0.2° and 29.53±0.2°.

In some embodiments of the present application, the crystalline form of the compound of formula (IV) comprises 4, 5, 6, 7, 8, 9, 10, 11 or 12 diffraction peaks in an X-ray powder diffraction pattern using Cu Kα radiation selected from the following 2θ angles: 11.22±0.2°, 12.58±0.2°, 16.43±0.2°, 17.08±0.2°, 17.90±0.2°, 18.85±0.2°, 19.23±0.2°, 19.72±0.2°, 22.62±0.2°, 23.27±0.2°, 24.45±0.2° and 25.87±0.2°.

In some embodiments of the present application, the crystalline form of the compound of formula (IV) comprises 4, 5, 6, 7 or 8 diffraction peaks in an X-ray powder diffraction pattern using Cu Kα radiation selected from the following 2θ angles: 11.22±0.2°, 12.58±0.2°, 16.43±0.2°, 17.90±0.2°, 18.85±0.2°, 22.62±0.2°, 24.45±0.2° and 25.87±0.2°.

In some embodiments of the present application, the crystalline form of the compound of formula (IV) has diffraction peaks in an XRPD pattern using Cu Kα radiation with peak positions and relative intensities as shown in Table 6 below:

TABLE 6

| No. | 2θ (±0.2°) | Relative intensity (%) |
|---|---|---|
| 1 | 8.71 | 9.3 |
| 2 | 11.22 | 91.6 |
| 3 | 12.58 | 49.1 |
| 4 | 13.88 | 11.5 |
| 5 | 15.49 | 11.4 |
| 6 | 16.04 | 23.7 |
| 7 | 16.43 | 51.1 |
| 8 | 17.08 | 25.9 |
| 9 | 17.90 | 32.5 |
| 10 | 18.54 | 31.5 |
| 11 | 18.85 | 100.0 |
| 12 | 19.23 | 28.1 |
| 13 | 19.72 | 27.3 |
| 14 | 20.02 | 13.5 |
| 15 | 20.51 | 14.0 |
| 16 | 20.86 | 10.2 |
| 17 | 21.26 | 10.1 |
| 18 | 22.62 | 79.6 |
| 19 | 23.27 | 19.0 |
| 20 | 24.06 | 8.2 |
| 21 | 24.45 | 75.1 |
| 22 | 24.83 | 18.1 |
| 23 | 25.10 | 11.4 |
| 24 | 25.42 | 16.9 |
| 25 | 25.87 | 28.4 |
| 26 | 26.09 | 18.2 |
| 27 | 26.76 | 8.5 |
| 28 | 27.22 | 7.8 |
| 29 | 27.93 | 10.1 |
| 30 | 28.87 | 9.6 |
| 31 | 29.17 | 9.7 |
| 32 | 29.53 | 13.8 |
| 33 | 31.14 | 7.1 |
| 34 | 32.46 | 8.3 |
| 35 | 33.63 | 9.6 |
| 36 | 36.29 | 6.4 |

In some embodiments of the present application, the crystalline form of the compound of formula (IV) has an XRPD pattern using Cu Kα radiation as shown in FIG. 13.

In some embodiments of the present application, the crystalline form of the compound of formula (IV) has an endothermic peaks at 191.35±2° C. and/or an exothermic peak at 222.21±2° C. in a differential scanning calorimetry curve.

In some embodiments of the present application, the crystalline form of the compound of formula (IV) has a differential scanning calorimetry pattern as shown in FIG. 14.

In some embodiments of the present application, the crystalline form of the compound of formula (IV) has a weight loss of 5.427% at 168.57±2° C., a weight loss of 4.678% at 168.57±2° C. to 192.84±2° C., and a weight loss of 4.621% at 192.84±2° C. to 238.22±2° C. in a thermogravimetric analysis curve.

In some embodiments of the present application, the crystalline form of the compound of formula (IV) has a thermogravimetric analysis pattern as shown in FIG. 15.

In another aspect, the present application further provides maleate of the compound of formula (I); in some embodiments, the maleate of the compound of formula (I) is selected from a compound of formula (V), (V)

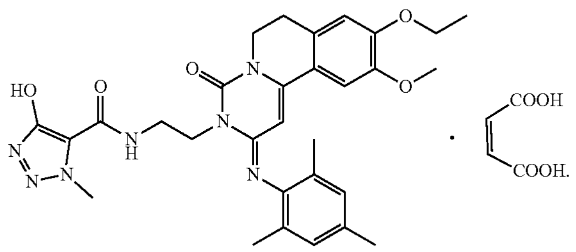

In another aspect, the present application further provides a crystalline form of the compound of formula (V) having diffraction peaks in an X-ray powder diffraction pattern using Cu Kα radiation at the following 2θ angles: 5.83±0.2°, 6.62±0.2°, 9.50±0.2° and 10.98±0.2°.

In some embodiments of the present application, the crystalline form of the compound of formula (V) has diffraction peaks in an X-ray powder diffraction pattern using Cu Kα radiation at the following 2θ angles: 5.83±0.2°, 6.62±0.2°, 9.50±0.2°, 10.98±0.2°, 17.16±0.2°, 19.05±0.2°, 24.71±0.2° and 25.16±0.2°.

In some embodiments of the present application, the crystalline form of the compound of formula (V) has diffraction peaks in the X-ray powder diffraction pattern using Cu Kα radiation at the following 2θ angles: 5.83±0.2°, 6.62±0.2°, 9.50±0.2°, 10.98±0.2°, 11.59±0.2°, 13.23±0.2°, 16.27±0.2°, 17.16±0.2°, 19.05±0.2°, 21.63±0.2°, 24.71±0.2° and 25.16±0.2°.

In some embodiments of the present application, the crystalline form of the compound of formula (V) comprises 4, 5, 6, 7, 8, 9, 10, 11 or 12 diffraction peaks in an X-ray powder diffraction pattern using Cu Kα radiation selected from the following 2θ angles: 5.83±0.2°, 6.62±0.2°, 9.50±0.2°, 10.98±0.2°, 11.59±0.2°, 13.23±0.2°, 16.27±0.2°, 17.16±0.2°, 19.05±0.2°, 21.63±0.2°, 24.71±0.2° and 25.16±0.2°.

In some embodiments of the present application, the crystalline form of the compound of formula (V) comprises 4, 5, 6, 7 or 8 diffraction peaks in an X-ray powder diffraction pattern using Cu Kα radiation selected from the following 2θ angles: 5.83±0.2°, 6.62±0.2°, 9.50±0.2°, 10.98±0.2°, 17.16±0.2°, 19.05±0.2°, 24.71±0.2° and 25.16±0.2°.

In some embodiments of the present application, the crystalline form of the compound of formula (V) has diffraction peaks in an XRPD pattern using Cu Kα radiation with peak positions and relative intensities as shown in Table 7 below:

TABLE 7

| No. | 2θ (±0.2°) | Relative intensity (%) |
|---|---|---|
| 1 | 5.83 | 12.3 |
| 2 | 6.62 | 100.0 |
| 3 | 9.50 | 11.7 |
| 4 | 10.98 | 14.7 |
| 5 | 11.59 | 3.8 |
| 6 | 13.23 | 4.3 |
| 7 | 16.27 | 4.1 |
| 8 | 17.16 | 10.2 |

TABLE 7-continued

| No. | 2θ (±0.2°) | Relative intensity (%) |
|---|---|---|
| 9 | 19.05 | 9.5 |
| 10 | 19.72 | 2.8 |
| 11 | 21.00 | 3.3 |
| 12 | 21.63 | 4.1 |
| 13 | 24.71 | 8.9 |
| 14 | 25.16 | 8.2 |
| 15 | 26.39 | 3.6 |
| 16 | 28.75 | 2.3 |
| 17 | 30.55 | 2.0 |
| 18 | 33.27 | 3.2 |

In some embodiments of the present application, the crystalline form of the compound of formula (V) has an XRPD pattern using Cu Kα radiation as shown in FIG. 16.

In some embodiments of the present application, the crystalline form of the compound of formula (V) has a weight loss of 1.928% at 155.26±2° C. in a thermogravimetric analysis curve.

In some embodiments of the present application, the crystalline form of the compound of formula (V) has a thermogravimetric analysis pattern as shown in FIG. 17.

In another aspect, the present application provides a method for preparing a salt of the compound of formula (I) comprising: mixing the compound of formula (I) with tetrahydrofuran; adding an aqueous solution of an acid (or a base); and separating the mixture to give the corresponding salt.

In still another aspect, the present application provides a crystalline composition comprising the crystalline form, wherein the crystalline form accounts for 50% or more, preferably 80% or more, more preferably 90% or more, and most preferably 95% or more of the weight of the crystalline composition.

In another aspect, the present application provides a compound of formula (I) or a pharmaceutically acceptable salt thereof, (I)

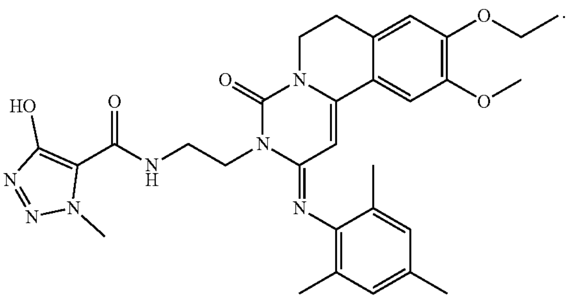

The compound of formula (I) is prepared by the following procedures:

(1) reacting compound 1-2a to give compound BB-4; and (2) reacting compound BB-4 with 5-hydroxy-3-methyl-1,2,3-triazole-4-carboxylic acid to give the compound of formula (I).

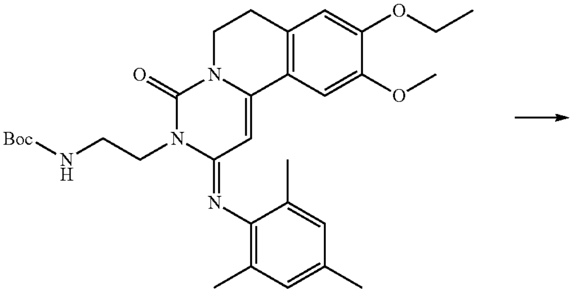

1-2a

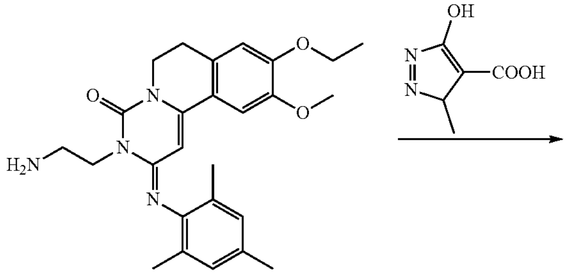

BB-4

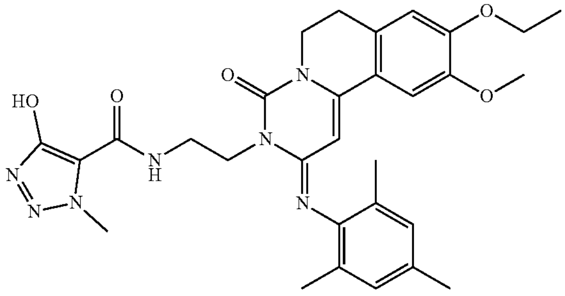

(I)

In another aspect, the present application provides a method for preparing the compound of formula (I), comprising the steps (1) and (2) above.

In still another aspect, the present application provides a method for preparing compound 1-2a comprising: reacting compound BB-1 with compound 1-1a to give compound 1-2a

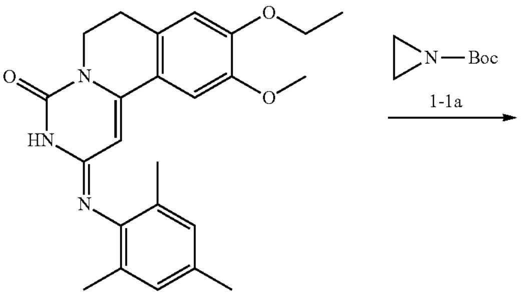

BB-1

-continued

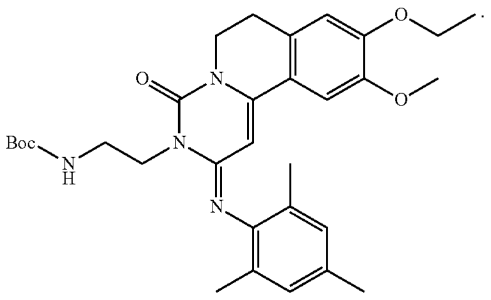

1-2a

In yet another aspect, the present application provides compound 1-2a or a pharmaceutically acceptable salt thereof 1-2a

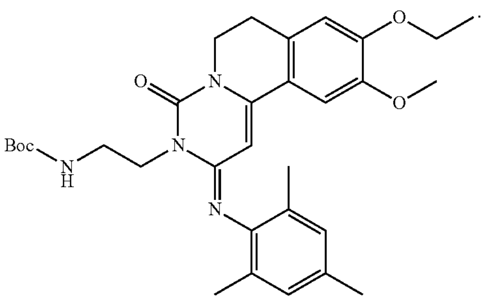

In yet another aspect, the present application provides a method for preparing compound BB-4 comprising:

(a) reacting compound BB-1 with compound 1-1a to give compound 1-2a; and (b) reacting compound 1-2a to give compound BB-4;

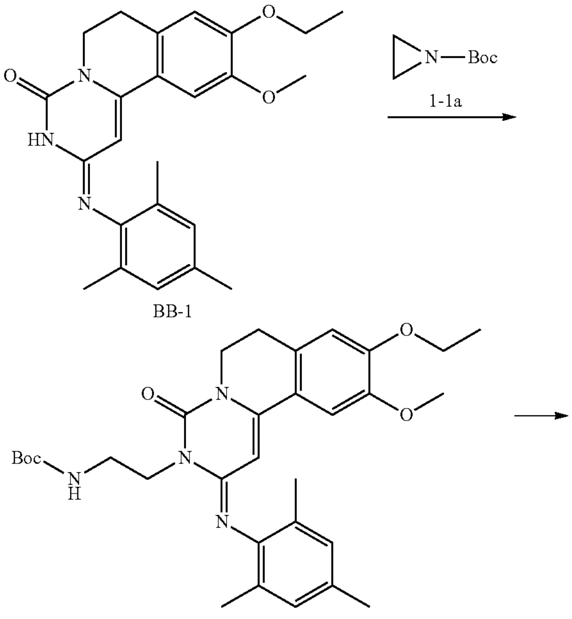

BB-1

1-2a

-continued

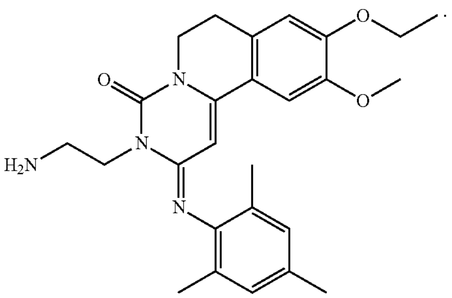

BB-4

In yet another aspect, the present application provides a compound of formula (I) or a pharmaceutically acceptable salt thereof (I)

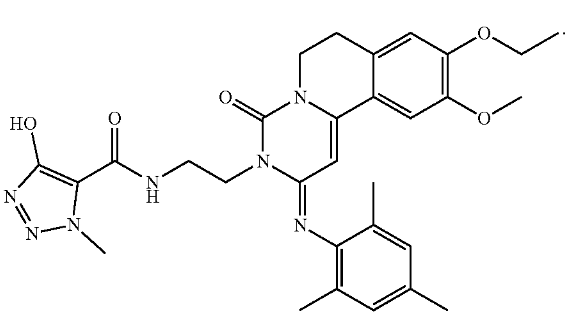

The compound of formula (I) is prepared by the following procedures:

(1') reacting compound BB-1 with compound 1-1a to give compound 1-2a;

(2') reacting compound 1-2a to give compound BB-4; and (3') reacting compound BB-4 with 5-hydroxy-3-methyl-1,2,3-triazole-4-carboxylic acid to give the compound of formula (I);

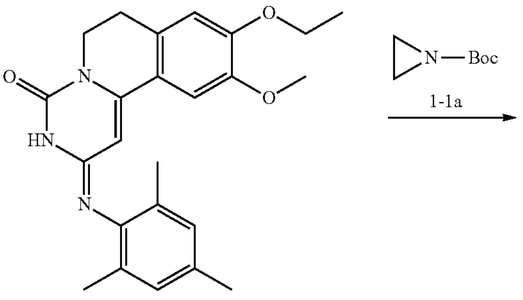

BB-1

-continued

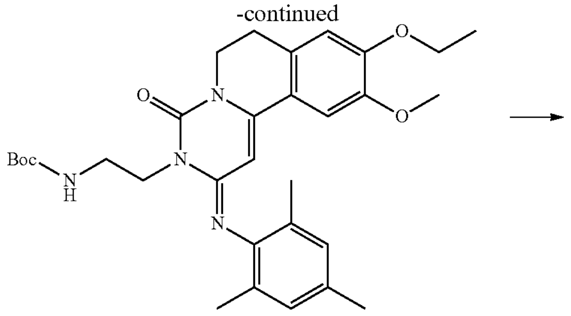

1-2a

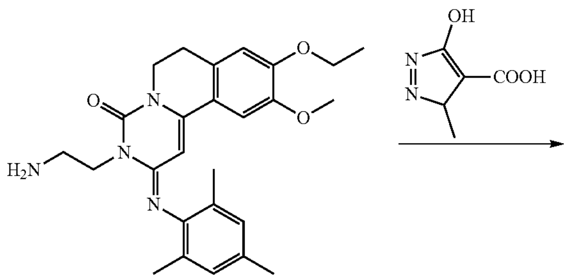

BB-4

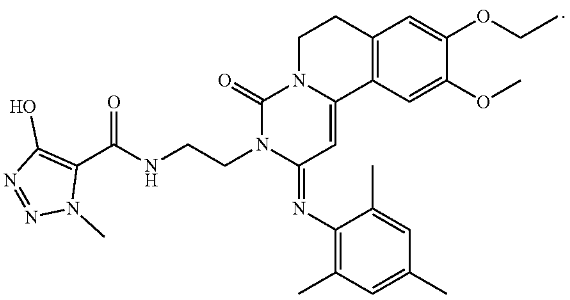

(I)

In yet another aspect, the present application provides a method for preparing the compound of formula (I), comprising the steps (1'), (2') and (3') above.

In some embodiments, the preparation of compound 1-2a is conducted in the presence of a solvent; in some embodiments, the solvent is selected from the group consisting of acetonitrile and water.

In some embodiments, the preparation of compound 1-2a is conducted in the presence of a base; in some embodiments, the base is selected from lithium carbonate.

In some embodiments, compound 1-2a is prepared by the following procedures: dissolving compound BB-1 and compound 1-1a in acetonitrile, and adding lithium carbonate and water for reaction.

In some embodiments, the reaction temperature for the preparation of compound 1-2a is 100° C.

In some embodiments, the reaction time for the preparation of compound 1-2a is 70 h.

In some embodiments, in preparing compound 1-2a, the molar ratio of compound BB-1 to compound 1-1a is 1:6.

In some embodiments, the preparation of compound BB-4 is conducted in the presence of hydrogen chloride.

In some embodiments, the preparation of compound BB-4 is conducted in the presence of a solvent; in some embodiments, the solvent is selected from methanol.

In some embodiments, compound BB-4 is prepared by the following procedures: reacting compound 1-2a in a solution of hydrogen chloride in methanol to give compound BB-4.

In some embodiments, the reaction temperature for the preparation of compound BB-4 is 60° C.

In some embodiments, the reaction time for the preparation of compound BB-4 is 2 h.

In some embodiments, the preparation of compound BB-4 further comprise treating the resulting mixture with petroleum ether and ethyl acetate after the reaction.

In some embodiments, the preparation of the compound of formula (I) by compound BB-4 is conducted in the presence of a solvent; in some embodiments, the solvent is selected from dichloromethane.

In some embodiments, the preparation of the compound of formula (I) by compound BB-4 is conducted in the presence of a base; in some embodiments, the base is selected from triethylamine.

In some embodiments, the preparation of the compound of formula (I) by compound BB-4 is conducted in the presence of a condensing agent; in some embodiments, the condensing agent is selected from HATU.

In some embodiments, in the preparation of the compound of formula (I) by compound BB-4, the molar ratio of 5-hydroxy-3-methyl-1,2,3-triazole-4-carboxylic acid to compound BB-4 is 1:(1-1.2).

In some embodiments, the reaction temperature for the preparation of the compound of formula (I) by compound BB-4 is 20° C.

In some embodiments, the reaction time for the preparation of the compound of formula (I) by compound BB-4 is 16 h.

In yet another aspect, the present application provides a compound of formula (I) or a pharmaceutically acceptable salt thereof (I)

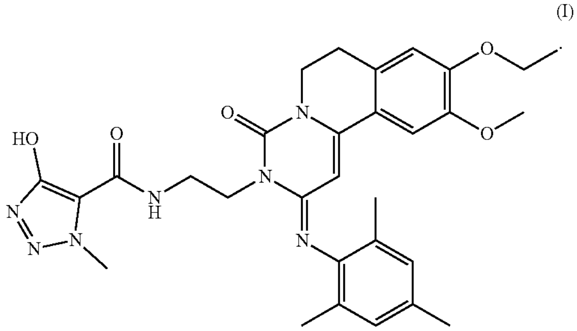

The compound of formula (I) is prepared by the following procedure: reacting compound 1-4b to give the compound of formula (I)

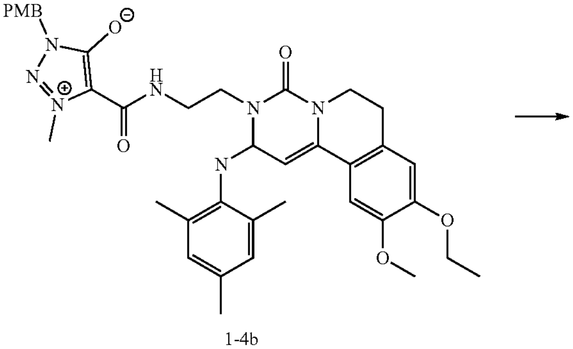

1-4b

-continued

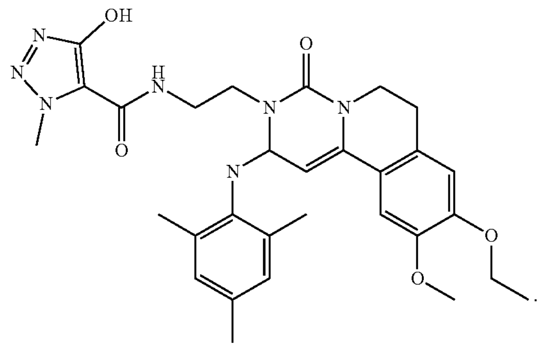

(I)

In yet another aspect, the present application provides a method for preparing the compound of formula (I), comprising: reacting compound 1-4b to give the compound of formula (I).

In yet another aspect, the present application provides a method for preparing compound 1-4b, comprising: reacting compound BB-4 with compound 1-3b to give compound 1-4b

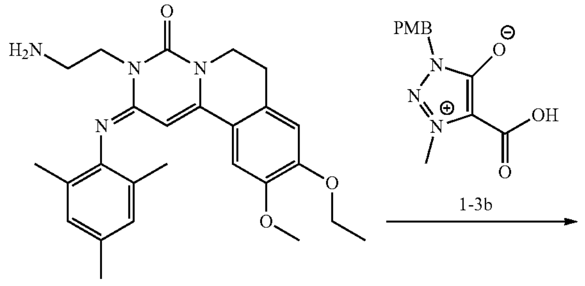

BB-4

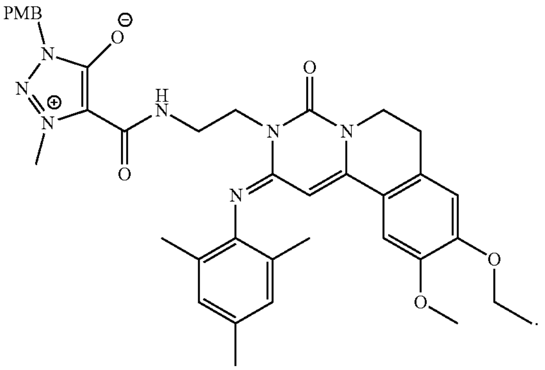

1-4b

In yet another aspect, the present application provides a method for preparing compound BB-4, comprising: reacting compound 1-1b to give compound BB-4

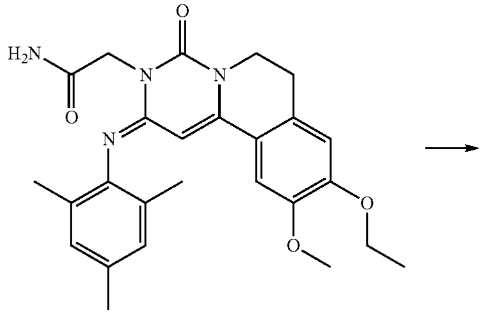

1-1b

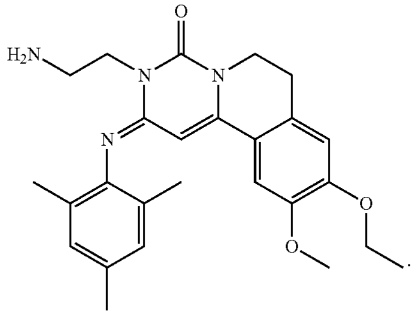

BB-4

In yet another aspect, the present application provides a method for preparing compound 1-1b, comprising: reacting compound BB-1 with compound a to give compound 1-1b

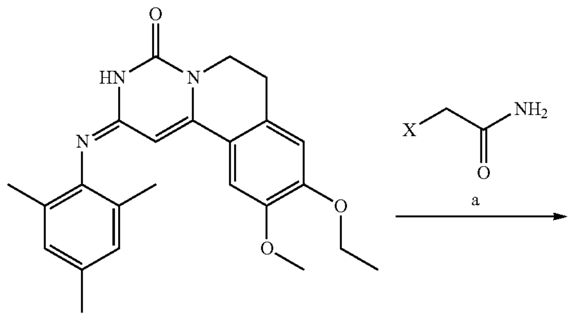

BB-1

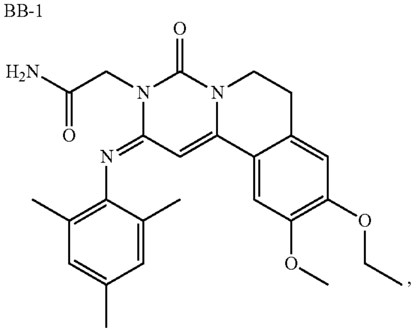

1-1b wherein X is selected from the group consisting of halogens.

In some embodiments, X is selected from the group consisting of Cl and Br; in some embodiments, X is selected from Br.

In yet another aspect, the present application provides a compound of formula (I) or a pharmaceutically acceptable salt thereof (I)

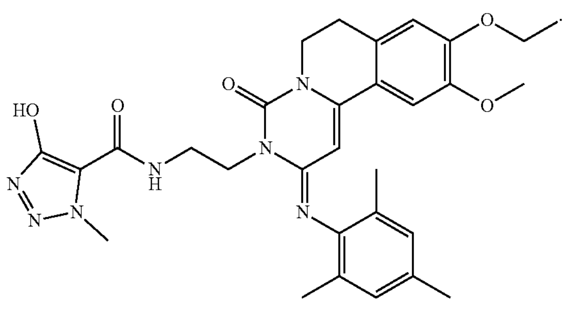

The compound of formula (I) is prepared by the following procedures:

(i) reacting compound BB-4 with compound 1-3b to give compound 1-4b; and (ii) reacting compound 1-4b to give the compound of formula (I).

In yet another aspect, the present application provides a method for preparing the compound of formula (I), comprising the steps (i) and (ii) above.

In yet another aspect, the present application provides a compound of formula (I) or a pharmaceutically acceptable salt thereof (I)

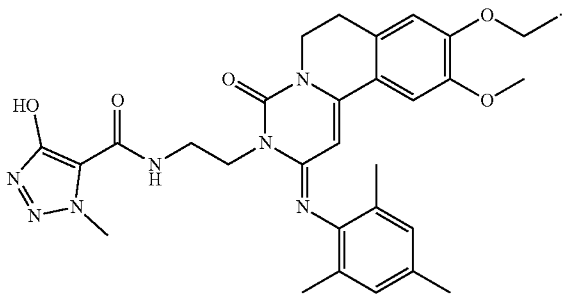

The compound of formula (I) is prepared by the following procedures:

(i') reacting compound 1-1b to give compound BB-4;

(ii') reacting compound BB-4 with compound 1-3b to give compound 1-4b; and (iii') reacting compound 1-4b to give the compound of formula (I).

In yet another aspect, the present application provides a method for preparing the compound of formula (I), comprising the steps (i'), (ii') and (iii') above.

In yet another aspect, the present application provides a compound of formula (I) or a pharmaceutically acceptable salt thereof (I)

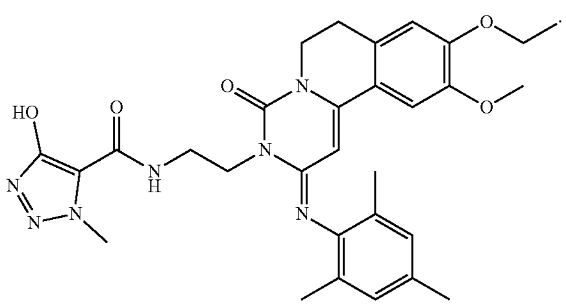

The compound of formula (I) is prepared by the following procedures:

(i") reacting compound BB-1 with compound a to give compound 1-1b;

(ii") reacting compound 1-1b to give compound BB-4;

(iii") reacting compound BB-4 with compound 1-3b to give compound 1-4b; and (iv") reacting compound 1-4b to give the compound of formula (I);

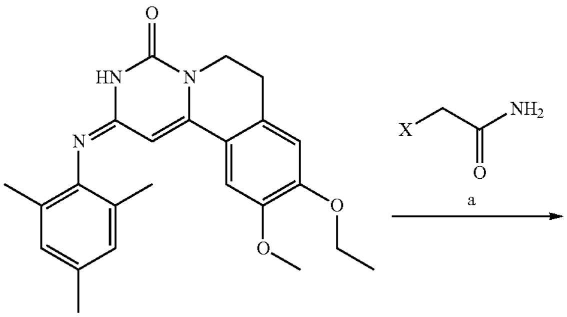

BB-1

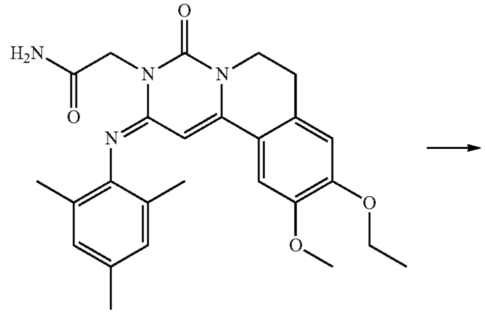

1-1b

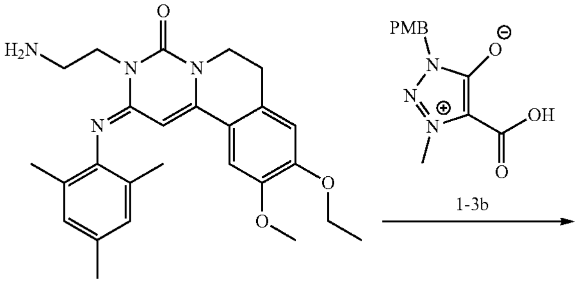

BB-4

-continued

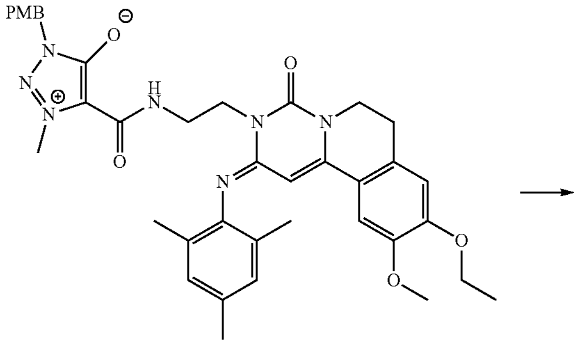

1-4b

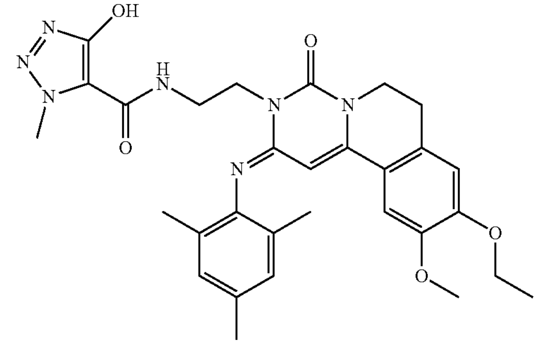

(I)

wherein X is selected from the group consisting of halogens.

In some embodiments, X is selected from the group consisting of Cl and Br; in some embodiments, X is selected from Br.

In yet another aspect, the present application provides a method for preparing the compound of formula (I), and the method comprises the steps (i"), (ii"), (iii") and (iv") above.

In yet another aspect, the present application provides compound 1-1b or a pharmaceutically acceptable salt thereof 1-1b

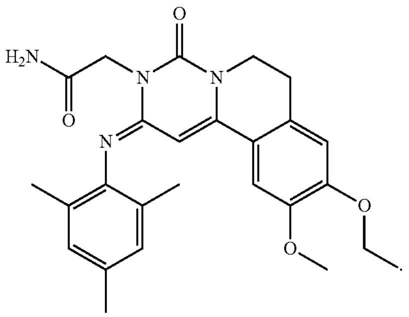

In yet another aspect, the present application provides compound 1-4b or a pharmaceutically acceptable salt thereof 1-4b

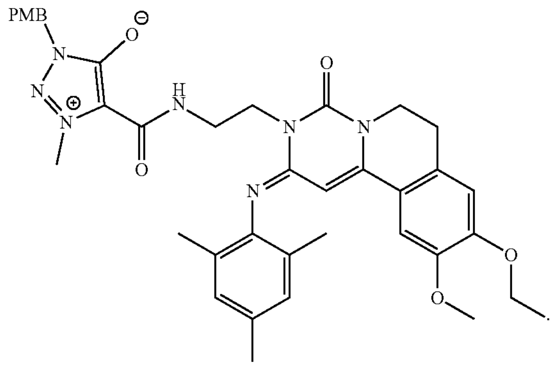

In some embodiments, the preparation of compound 1-1b is conducted in the presence of a solvent; in some embodiments, the solvent is selected from 2-butanone.

In some embodiments, the preparation of compound 1-1b is conducted in the presence of a catalyst; in some embodiments, the catalyst is selected from potassium phosphate, e.g., anhydrous potassium phosphate.

In some embodiments, the preparation of compound 1-1b is conducted in the presence of a co-solvent; in some embodiments, the co-solvent is selected from sodium iodide.

In some embodiments, the preparation of compound 1-1b is conducted in the presence of potassium phosphate and sodium iodide.

In some embodiments, in the preparation of compound 1-1b, the molar ratio of compound BB-1 to the compound a is 1:3.

In some embodiments, the reaction temperature for the preparation of compound 1-1b is 90° C.

In some embodiments, the reaction time for the preparation of compound 1-1b is 18 h.

In some embodiments, the preparation of compound BB-4 is conducted in the presence of a solvent; in some embodiments, the solvent is selected from tetrahydrofuran.

In some embodiments, the preparation of compound BB-4 is conducted in the presence of borane-dimethyl sulfide.

In some embodiments, the reaction temperature for the preparation of compound BB-4 is 20-25° C.

In some embodiments, the reaction time for the preparation of compound BB-4 is 18 h.

In some embodiments, the preparation of compound BB-4 comprises: adding compound 1-1b to a mixture of tetrahydrofuran and borane-dimethyl sulfide at 0° C.; and heating the system for reaction.

In some embodiments, the system is heated to 20-25° C. for reaction.

In some embodiments, the preparation of compound BB-4 comprises: cooling the system (e.g., to 0° C.) after a period of reaction (e.g., 18 h); the preparation further comprises: adding methanol after cooling; the preparation further comprises: adjusting pH after adding methanol; the preparation further comprises: concentrating after adjusting pH; the preparation further comprises: purifying.

In some embodiments, adjusting pH after adding methanol comprises adjusting pH to 2-3.

In some embodiments, adjusting pH after adding methanol comprises adjusting pH using hydrochloric acid.

In some embodiments, in the preparation of compound 1-4b, the molar ratio of compound BB-4 to compound 1-3b is 1:(1-1.5).

In some embodiments, the preparation of compound 1-4b is conducted in the presence of a condensing agent; in some embodiments, the condensing agent is N,N-carbonyldiimidazole.

In some embodiments, the preparation of compound 1-4b comprises: reacting compound 1-3b with a condensing agent (e.g., N,N-carbonyldiimidazole), and reacting the resulting mixture with compound BB-4 to give compound 1-4b.

In some embodiments, in the preparation of compound 1-4b, reacting compound 1-3b with an activating agent is conducted in the presence of a solvent; in some embodiments, the solvent is selected from dichloromethane.

In some embodiments, in the preparation of compound 1-4b, the reaction temperature for reacting compound 1-3b with the activating agent is 25° C.

In some embodiments, in the preparation of compound 1-4b, the reaction time for reacting compound 1-3b with the activating agent is 5 h.

In some embodiments, in the preparation of compound 1-4b, reacting compound 1-3b with the activating agent and reacting the resulting mixture with compound BB-4 are conducted in the presence of a solvent; in some embodiments, the solvent is selected from DMF.

In some embodiments, in the preparation of compound 1-4b, the reaction temperature for reacting compound 1-3b with the activating agent and reacting the resulting mixture with compound BB-4 is 20-25° C.

In some embodiments, in the preparation of compound 1-4b, the reaction time for reacting compound 1-3b with the activating agent and reacting the resulting mixture with compound BB-4 is 18 h.

In some embodiments, the preparation of compound 1-4b further comprise: adding methanol for treatment after the reaction.

In some embodiments, the preparation of the compound of formula (I) by compound 1-4b is conducted in the presence of a solvent; in some embodiments, the solvent is selected from a mixed solvent of trifluoroacetic acid and acetic acid.

In some embodiments, the volume ratio of trifluoroacetic acid to acetic acid is 5:1.

In some embodiments, the reaction temperature for the preparation of the compound of formula (I) by compound 1-4b is 90-100° C.

In some embodiments, the reaction time for the preparation of the compound of formula (I) by compound 1-4b is 48 h.

In some embodiments, for the compound of formula (I) or the pharmaceutically acceptable salt thereof, the compound of formula (I) is a crystalline form, and the crystalline form is a crystalline form A of the compound of formula (I), a crystalline form B of the compound of formula (I), or a crystalline form C of the compound of formula (I).

In some embodiments, for the compound of formula (I) or the pharmaceutically acceptable salt thereof, the pharmaceutically acceptable salt is sulfate, p-toluenesulfonate, methanesulfonate or maleate.

Compound BB-1 of the present application is prepared by the following procedures:

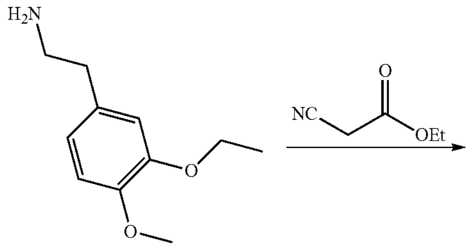

BB-1-1

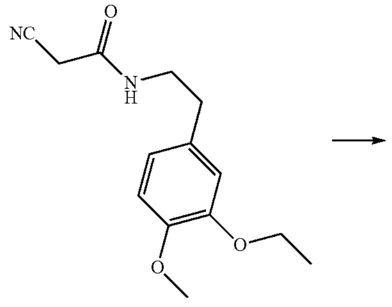

BB-1-2

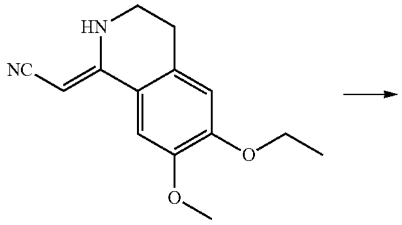

BB-1-3

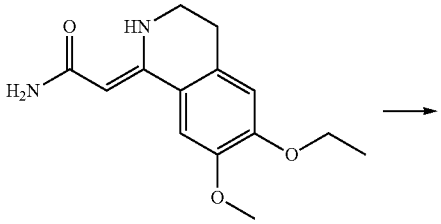

BB-1-4

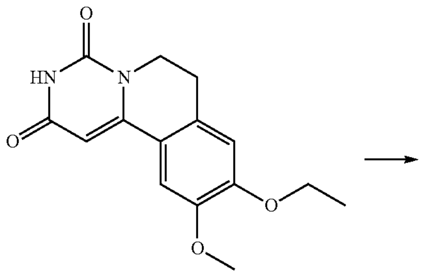

BB-1-5

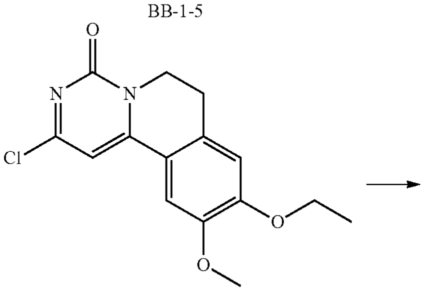

BB-1-6

-continued

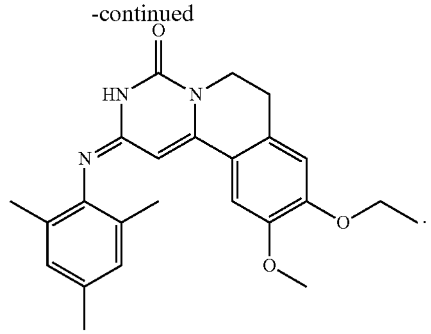

BB-1

In another aspect, the present application provides a method for preparing the crystalline form of the compound of formula (I) or the pharmaceutically acceptable salt thereof, comprising: preparing the compound of formula (I) or the pharmaceutically acceptable salt thereof by any of the above-mentioned methods for preparing the compound of formula (I) or the salt thereof and precipitating the compound of formula (I) or the pharmaceutically acceptable salt thereof in a solvent selected from the group consisting of: methanol, a mixed solvent of ethanol and water, acetonitrile and a mixed solvent of tetrahydrofuran and water. In some specific embodiments, the present application provides a method for preparing the crystalline form of the pharmaceutically acceptable salt of the compound of formula (I), comprising: precipitating the salt of the compound of formula (I) in a mixed solvent of tetrahydrofuran and water. In other specific embodiments, the present application provides a method for preparing the crystalline form of the pharmaceutically acceptable salt of the compound of formula (I) comprising: mixing the compound of formula (I) with tetrahydrofuran, adding an aqueous solution of acid (and/or base) for reaction, and precipitating the salt of the compound of formula (I) in a mixed solvent of tetrahydrofuran and water in a form of the crystalline form.

In yet another aspect, the present application provides a pharmaceutical composition comprising a therapeutically effective amount of the compound of formula (I) or the pharmaceutically acceptable salt thereof, the crystalline form, or the crystalline composition thereof disclosed herein. The pharmaceutical composition disclosed herein may or may not contain a pharmaceutically acceptable excipient. In addition, the pharmaceutical composition disclosed herein may further comprise one or more additional therapeutic agents.

In another aspect, the present application further provides a method for preventing or treating a condition associated with PDE3 and/or PDE4 in a mammal, comprising administering to a mammal, preferably a human, in need thereof a therapeutically effective amount of the compound of formula (I) or the pharmaceutically acceptable salt thereof, the crystalline form thereof, the crystalline composition thereof, or the pharmaceutical composition thereof.

In another aspect, the present application further provides use of the compound of formula (I) or the pharmaceutically acceptable salt thereof, the crystalline form thereof, the crystalline composition thereof, or the pharmaceutical composition thereof in preparing a medicament for preventing or treating a condition associated with PDE3 and/or PDE4.

In another aspect, the present application further provides use of the compound of formula (I) or the pharmaceutically acceptable salt thereof, the crystalline form thereof, the crystalline composition thereof, or the pharmaceutical composition thereof in preventing or treating a condition associated with PDE3 and/or PDE4.

In another aspect, the present application further provides the compound of formula (I) or the pharmaceutically acceptable salt thereof, the crystalline form thereof, the crystalline composition thereof, or the pharmaceutical composition thereof for use in preventing or treating a condition associated with PDE3 and/or PDE4.

In some embodiments of the present application, the condition associated with PDE3 and/or PDE4 is selected from the group consisting of asthma and chronic obstructive pulmonary disease (COPD).

Technical Effects

The compound of formula (I) disclosed herein has remarkable dual inhibitory effect on PDE3 and PDE4, has significant inhibitory effect on TNF-α in human peripheral blood mononuclear cells (hPBMCs), and also shows excellent anti-inflammatory effect in rat acute lung injury model induced by lipopolysaccharide (LPS). The compound has high in vivo plasma clearance, low systemic exposure in plasma by oral administration and low oral bioavailability, and good safety in administration via a local route. Its inhibitory effect is low on 5 isoenzymes (CYP1A2, CYP2C9, CYP2C19, CYP2D6 and CYP3A4) of human liver microsomal cytochrome P450, and the risk of drug-drug interaction is avoided. Besides, the compound reduces the total white blood cells in BALF, has remarkable anti-inflammatory effect, takes effect at a low dose, and reduces the airway resistance index Penh.

The crystalline form of the compound of formula (I) and the pharmaceutically acceptable salt thereof of the present application have advantages in terms of pharmaceutical activity, pharmacokinetics, bioavailability, hygroscopicity, melting point, stability, solubility, purity, ease of preparation, etc., to meet the requirements of pharmaceutics in terms of production, storage, transportation, formulation, etc.

In the methods for preparing the compound of formula (I) disclosed herein, in the method 2, the aminoethyl-substituted compound can be obtained in one step, the reaction system is clean, and no further reduction is needed after an amide or a cyano group is introduced in the conventional method. The method 3 replaces the genotoxic reagent bromoacetonitrile with non-genotoxic bromoacetamide, thereby reducing the safety risk for the synthesis and development of the medicament.

Definitions and Description

Unless otherwise stated, the following terms and phrases used herein are intended to have the following meanings. A particular phrase or term, unless otherwise specifically defined, should not be considered as uncertain or unclear, but construed according to its common meaning. When referring to a trade name, it is intended to refer to its corresponding commercial product or its active ingredient.

It should be noted that in the X-ray powder diffraction pattern, the position and relative intensity of a peak may vary due to measuring instruments, measuring methods/conditions, and other factors. For any specific crystal form, the position of a peak may have an error, and the measurement of 2θ may have an error of ±0.2°. Therefore, this error should be considered when determining each crystal form, and crystal forms within this margin of error are within the scope of the present application.

It should be noted that, for the same crystal form, the position of an endothermic peak in the DSC (differential scanning calorimetry) pattern may vary due to measuring instruments, measuring methods/conditions, and other factors. For any specific crystal form, the position of an endothermic peak may have an error of ±5° C. or ±3° C. Therefore, this error should be considered when determining each crystal form, and crystal forms within this margin of error are within the scope of the present application.

The word "comprise", and variants thereof such as "comprises" or "comprising", or equivalents shall be understood in an open, non-exclusive sense, i.e., "includes but is not limit to", indicating that in addition to the listed elements, components and procedures, other unspecified elements, components and procedures may also be encompassed.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt", as a pharmaceutically acceptable salt, for example, may refer to a metal salt, an ammonium salt, a salt formed with an organic base, a salt formed with an inorganic acid, a salt formed with an organic acid, a salt formed with a basic or acidic amino acid, and the like.

The term "pharmaceutically acceptable excipient" refers to an inert substance administered with active ingredient to facilitate administration of the active ingredient, including, but not limited to, any glidant, sweetener, diluent, preservative, dye/coloring agent, flavor enhancer, surfactant, wetting agent, dispersant, disintegrant, suspending agent, stabilizer, isotonizing agent, solvent or emulsifier acceptable for use in humans or animals (e.g., domesticated animals) as permitted by the National Medical Products Administration, PRC. Non-limiting examples of the excipients include calcium carbonate, calcium phosphate, various sugars and types of starch, cellulose derivatives, gelatin, vegetable oils, and polyethylene glycols.

The term "pharmaceutical composition" refers to a mixture consisting of one or more of the compounds or the salts thereof disclosed herein and a pharmaceutically acceptable excipient. The pharmaceutical composition is intended to facilitate the administration of the compound to an organic entity.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere and aerosol.

Typical routes of administration of the crystalline form or the pharmaceutical composition thereof disclosed herein include, but are not limited to, oral, rectal, topical, inhalational, parenteral, sublingual, intravaginal, intranasal, intraocular, intraperitoneal, intramuscular, subcutaneous and intravenous administrations.

The pharmaceutical composition disclosed herein can be manufactured using methods well known in the art, such as conventional mixing, dissolving, granulating, dragee-making, levigating, emulsifying, and lyophilizing.

In some embodiments, the pharmaceutical composition is in an oral form. For oral administration, the pharmaceutical composition can be formulated by mixing the active compounds with pharmaceutically acceptable excipients well known in the art. These excipients enable the compound disclosed herein to be formulated into tablets, pills, pastilles, dragees, capsules, liquids, gels, slurries, suspensions, etc. for oral administration to a patient.

Therapeutic dosages of the compounds disclosed herein may be determined by, for example, the specific use of a treatment, the route of administration of the compound, the health and condition of a patient, and the judgment of a prescribing physician. The proportion or concentration of the compound disclosed herein in a pharmaceutical composition may not be constant and depends on a variety of factors including dosages, chemical properties (e.g., hydrophobicity), and routes of administration. The term "treating" or "treatment" means administering the compound or formulation described herein to ameliorate or eliminate a disease or one or more symptoms associated with the disease, and includes:

(i) inhibiting a disease or disease state, i.e., arresting its development; and (ii) alleviating a disease or disease state, i.e., causing its regression.

The term "prevent" or "prevention" means administering the compound or formulation described herein to prevent a disease or one or more symptoms associated with the disease, and includes: preventing the occurrence of the disease or disease state in a mammal, particularly when such a mammal is predisposed to the disease state but has not yet been diagnosed with it.

For drugs and pharmacological active agents, the term "therapeutically effective amount" refers to an amount of a drug or a medicament that is sufficient to provide the desired effect and is non-toxic. The determination of the effective amount varies from person to person. It depends on the age and general condition of a subject, as well as the particular active substance used. The appropriate effective amount in a case may be determined by those skilled in the art in the light of conventional tests.

The therapeutically effective amount of the crystalline form disclosed herein is from about 0.0001 to 20 mg/kg body weight (bw)/day, for example from 0.001 to 10 mg/kg bw/day.

The dosage frequency of the crystalline form disclosed herein depends on needs of an individual patient, e.g., once or twice daily or more times daily. Administration may be intermittent, for example, in a period of several days, the patient receives a daily dose of the crystal forms, and in the following period of several days or more days, the patient does not receive the daily dose of the crystal forms.

Unless otherwise specified clearly herein, singular terms encompass plural terms, and vice versa.

Unless otherwise indicated herein, parameter values (including 20 values, reaction conditions) are to be construed as modified by the term "about" to reflect the measurement error and the like existing in the values, e.g., there is an error of ±5% relative to the given value.

All patents, patent applications and other identified publications are expressly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates or the content of these documents. Moreover, in any country or region, any reference to these publications herein is not to be construed as an admission that the publications form part of the commonly recognized knowledge in the art.

The present application is described in detail below by way of examples, which are not intended to limit the present application in any way.

The intermediate compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein.

The chemical reactions of the embodiments disclosed herein are carried out in a proper solvent that must be suitable for the chemical changes in the present application and the reagents and materials required. In order to acquire the compounds disclosed herein, it is sometimes necessary for those skilled in the art to modify or select a synthesis procedure or a reaction scheme based on the existing embodiments.

The present application is described in detail below by way of examples, which are not intended to limit the present application in any way.

All solvents used in the present application are commercially available and can be used without further purification.

The solvents used in the present application are commercially available. The following abbreviations are used in the present application: DMSO denotes dimethyl sulfoxide; TsOH denotes p-toluenesulfonic acid; MsOH denotes methanesulfonic acid.

X-Ray Powder Diffraction (XRPD)

Instrument model: Bruker D8 advance X-ray diffractometer; light tube: Cu, Kα (λ=1.54056 Å).

Differential Scanning Calorimetry (DSC)

Instrument model: TA Q2000 differential scanning calorimeter

Thermogravimetric Analysis (TGA)

Instrument model: TA Q5000IR thermogravimetric analyzer

DETAILED DESCRIPTION

Figure 1:
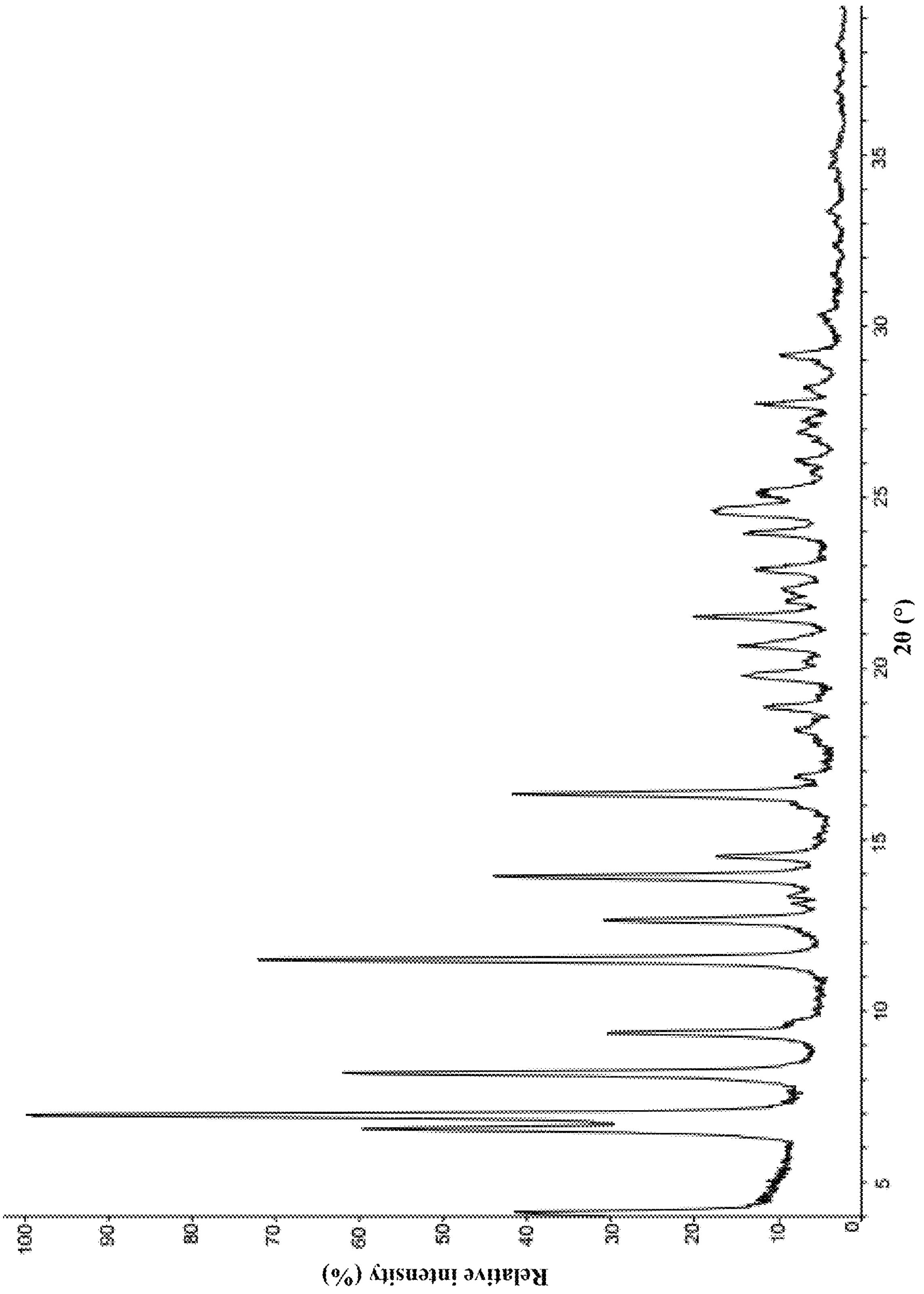
FIG. 1 is an XRPD pattern of a crystalline form A of the compound of formula (I)

In order to better understand the content of the present application, further description is given with reference to specific examples, but the specific embodiments are not intended to limit the content of the present application.

Synthesis of Intermediate BB-1

BB-1

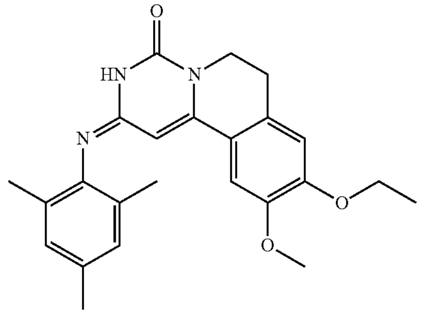

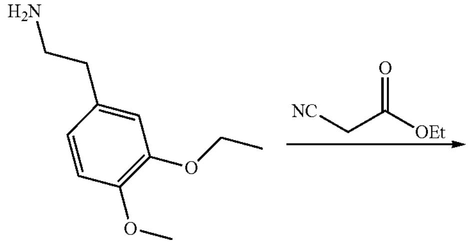

BB-1-1

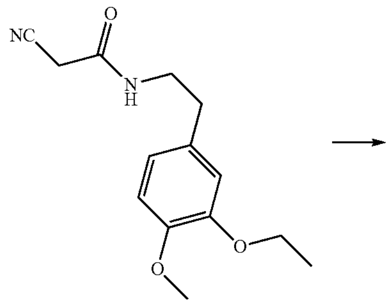

BB-1-2

-continued

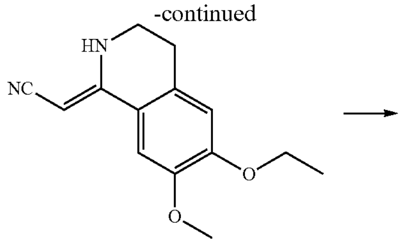

BB-1-3

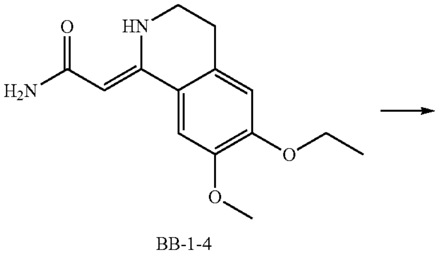

BB-1-4

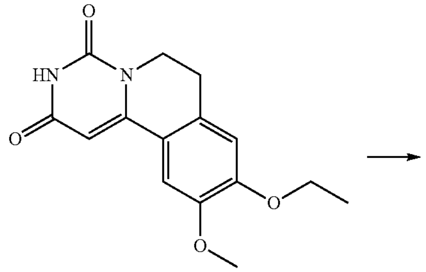

BB-1-5

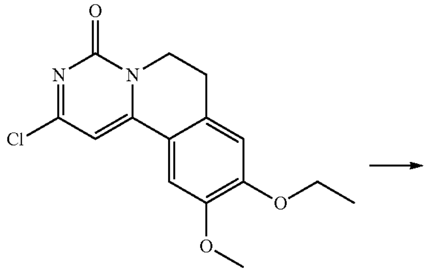

BB-1-6

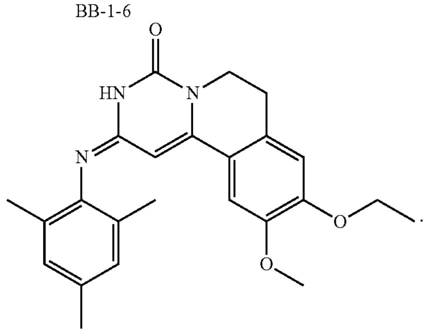

BB-1

Step 1: Synthesis of Compound BB-1-2

A mixture of compound BB-1-1 (21.10 g) and ethyl cyanoacetate (11.00 g, 10.38 mL) was stirred at 100° C. for 16 h in nitrogen atmosphere. After completion of the reaction, the mixture was cooled to 70° C., ethanol (30 mL) was slowly and dropwise added, and a large amount of solid was precipitated. The resulting mixture was filtered, and the filter cake was dried under reduced pressure to give product BB-1-2.

$^1$H NMR (400 MHz, DMSO-d6) δ=8.26 (t, J=5.2 Hz, 1H), 6.86 (d, J=8.0 Hz, 1H), 6.79 (br s, 1H), 6.71 (d, 8.0 Hz, 1H), 4.00 (q, J=6.8 Hz, 2H), 3.72 (s, 3H), 3.59 (s, 2H), 3.31-3.23 (m, 2H), 2.64 (t, J=7.2 Hz, 2H), 1.32 (t, J=6.8 Hz, 3H). MS-ESI m/z: 263.1[M+H]$^+$.

Step 2: Synthesis of Compound BB-1-3

In nitrogen atmosphere, phosphorus oxychloride (379.50 g, 230.00 mL) was heated to 85° C., and compound BB-1-2 (26.00 g) was added in portions. The reaction mixture was stirred at 85° C. for 2 h for reaction. After the reaction was completed, most of the phosphorus oxychloride was removed by reduced pressure distillation. To the residue was added dichloromethane (200 mL) and the mixture was washed with water (100 mL×2). The organic phase was dried over anhydrous sodium sulfate, filtered to remove the desiccant, and then concentrated under reduced pressure. The resulting crude product was purified by slurrying with ethyl acetate (20 mL) to give compound BB-1-3.

$^1$H NMR (400 MHz, $CD_3OD$) δ=7.16 (s, 1H), 6.83 (s, 1H), 4.62 (s, 1H), 4.12 (q, J=6.8 Hz, 2H), 3.86 (s, 3H), 3.35 (d, J=6.4 Hz, 2H), 2.84 (t, J=6.4 Hz, 2H), 1.44 (t, J=6.8 Hz, 3H). MS-ESI m/z: 245.1[M+H]$^+$.

Step 3: Synthesis of Compound BB-1-4

Compound BB-1-3 (1.00 g) was added to 98% concentrated sulfuric acid (12.88 g, 128.69 mmol, 7.00 mL) in portions at 0° C. The reaction mixture was stirred at 27° C. for 3 h. After the reaction was completed, the mixture was added to cold water (15 mL), and then aqueous sodium hydroxide solution (4 mol/L, 32 mL) was added dropwise to adjust to a neutral pH, followed by extraction with ethyl acetate (100 mL×3). The organic phases were combined, dried over anhydrous sodium sulfate, filtered to remove the desiccant, and concentrated under reduced pressure to give compound BB-1-4.

MS-ESI m/z: 263.1[M+H]$^+$.

Step 4: Synthesis of Compound BB-1-5

Sodium (2.42 g) was added in portions to ethanol (80 mL) at 0° C. After the mixture was stirred at 28° C. for 0.5 h, compound BB-1-4 (6.90 g) was added to the solution in portions, and the mixture was stirred at 80° C. for 0.5 h. Then, diethyl carbonate (9.32 g, 9.51 mL) was added in one portion, and the mixture was stirred for 5 h at 80° C. After the reaction was completed, the mixture was cooled to room temperature, ice water (30 mL) was slowly added, and then diluted hydrochloric acid (2 mol/L, 53 mL) was added to adjust the mixture to a neutral pH. A large amount of solid was precipitated. The mixture was filtered, and the resulting filter cake was purified by slurrying with ethanol (10 mL) to give compound BB-1-5.

$^1$H NMR (400 MHz, DMSO-$d_6$) δ=11.22 (br s, 1H), 7.35 (s, 1H), 6.95 (s, 1H), 6.22 (s, 1H), 4.09 (q, J=6.8 Hz, 2H), 3.90 (br s, 2H), 3.83 (s, 3H), 2.89 (br s, 2H), 1.35 (t, J=6.8 Hz, 3H). MS-ESI m/z: 289.1[M+H]$^+$.

Step 5: Synthesis of Compound BB-1-6

Compound BB-1-5 (5.00 g) was dissolved in phosphorus oxychloride (30 mL) at room temperature. The reaction mixture was stirred at 100° C. for 16 h in nitrogen atmosphere. After the reaction was completed, most of the solvent was removed by reduced pressure distillation. Water (100 mL) was added and the resulting mixture was extracted with dichloromethane (150 mL×2). The organic phases were combined, dried over anhydrous sodium sulfate, filtered to remove the desiccant, and concentrated under reduced pressure to give compound BB-1-6. MS-ESI m/z: 306.9[M+H]$^+$.

Step 6: Synthesis of Compound BB-1

Compound BB-1-6 (925.67 mg) was dissolved in isopropanol (8 mL) at room temperature, and 2,4,6-trimethylaniline (2.10 g) was added. The reaction mixture was stirred at 90° C. for 15 h in nitrogen atmosphere. After the reaction was completed, the mixture was cooled to room temperature and concentrated under reduced pressure, and the resulting residue was purified by slurrying with ethanol (6 mL) to give compound BB-1.

$^1$H NMR (400 MHz, DMSO-$d_6$) δ=8.85 (br s, 1H), 7.27 (s, 1H), 6.97 (s, 1H), 6.90 (s, 2H), 6.45 (s, 1H), 4.10 (q, J=6.8 Hz, 2H), 3.90 (t, J=6.0 Hz, 2H), 3.86 (s, 3H), 2.87 (t, J=6.0 Hz, 2H), 2.45 (s, 3H), 2.11 (s, 6H), 1.37 (t, J=6.8 Hz, 3H). MS-ESI m/z: 406.2[M+H]$^+$.

Synthesis of compound BB-4

BB-4

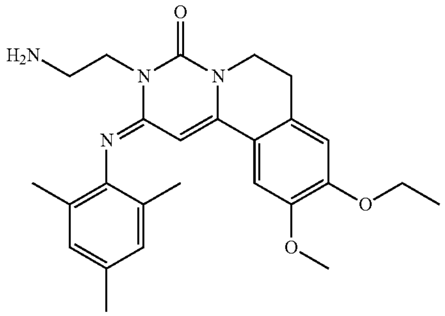

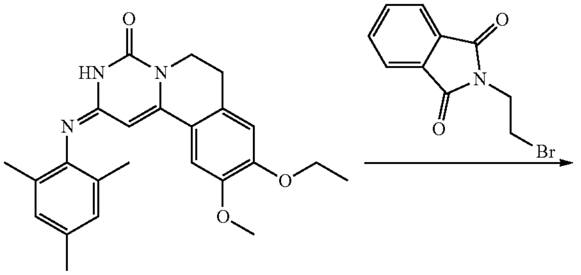

BB-1

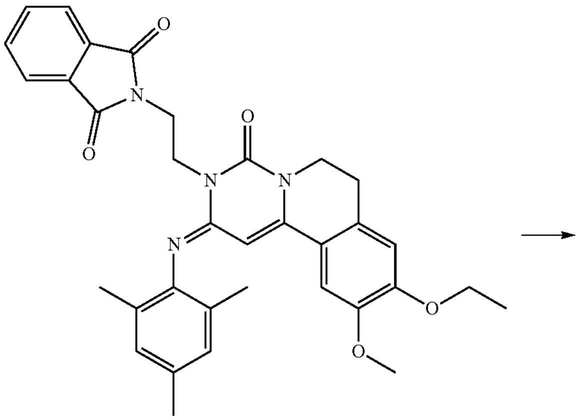

BB-4-1

-continued

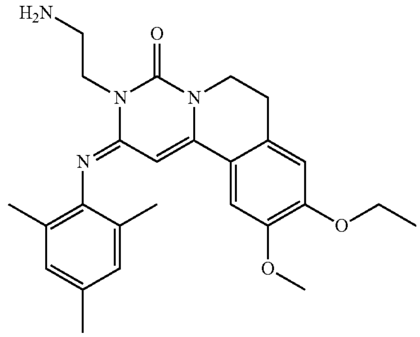

BB-4

Step 1: Synthesis of Compound BB-4-1

Compound BB-1 (1.00 g) was dissolved in 2-butanone (35 mL) at room temperature, and 2-(2-bromoethyl)isoindoline-1,3-dione (3.76 g), potassium carbonate (3.07 g) and sodium iodide (2.22 g) were added successively. The reaction mixture was stirred at 85° C. for 72 h in nitrogen atmosphere. After the reaction was completed, the mixture was concentrated to remove most of the organic solvent before water (30 mL) and ethyl acetate (25 mL×3) were added for extraction. The organic phases were combined, dried over anhydrous sodium sulfate, filtered to remove the desiccant and concentrated under reduced pressure. The resulting residue was purified by flash silica gel column chromatography (eluent:petroleum ether:ethyl acetate=15:1-3:1) to give compound BB-4-1.

MS-ESI m/z: 579.3[M+H]$^+$.

Step 2: Synthesis of Compound BB-4

Compound BB-4-1 (500.00 mg) was dissolved in trichloromethane (3 mL) and ethanol (3 mL) at room temperature, and hydrazine hydrate (152.67 mg, 85% purity) was added. The mixture was stirred at 28° C. for 16 h in nitrogen atmosphere. After the reaction was completed, the mixture was concentrated to remove most of the organic solvent before water (15 mL) and dichloromethane (15 mL×3) were added for extraction. The organic phases were combined, dried over anhydrous sodium sulfate, filtered to remove the desiccant, and concentrated under reduced pressure to give compound BB-4.

$^1$H NMR (400 MHz, DMSO-$d_6$) δ=6.95 (s, 1H), 6.85 (br s, 2H), 6.66 (s, 1H), 5.31 (s, 1H), 4.14 (t, J=6.8 Hz, 2H), 4.05 (q, J=6.8 Hz, 2H), 3.91 (t, J=6.4 Hz, 2H), 3.62 (s, 3H), 2.90-2.86 (m, 4H), 2.22 (s, 3H), 1.95 (br s, 6H), 1.33 (t, J=6.8 Hz, 3H). MS-ESI m/z: 449.2[M+H]$^+$.

Example 1: Preparation of Compound of Formula (I)

Method 1

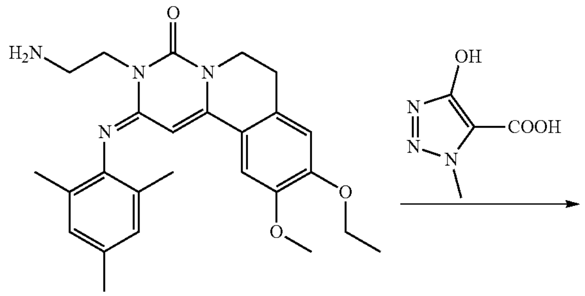

BB-4

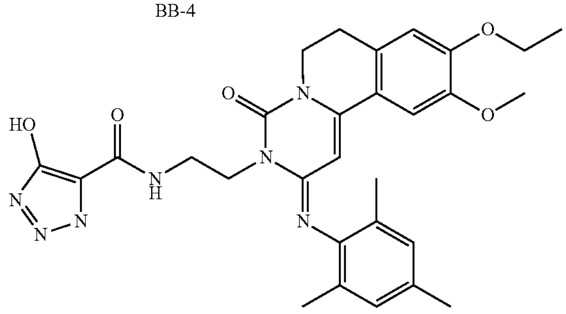

(I)

5-Hydroxy-3-methyl-1,2,3-triazole-4-carboxylic acid (18.50 mg) was dissolved in DCM (1 mL) at 20° C. HATU (8.80 mg) and triethylamine (57.40 μL) were added and the mixture was stirred for 2 h. Compound BB-4 (50 mg) was added and the system was stirred at the temperature for 16 h. The mixture was diluted to 10 mL with DCM, washed with water (30 mL×3), dried over anhydrous sodium sulfate, and filtered to remove the desiccant, and the filtrate was concentrated under reduced pressure to remove the solvent to give a crude product. The crude product was separated and purified by prep-HPLC to give the target compound of formula (I) in the form of a yellow solid.

$^1$H NMR (400 MHz, $CD_3OD$) δ=6.94 (s, 2H), 6.87 (s, 1H), 6.77 (s, 1H), 5.52 (s, 1H), 4.48 (t, J=6.0 Hz, 2H), 4.15 (s, 3H), 4.12-4.08 (m, 2H), 4.01 (t, J=6.0 Hz, 2H), 3.87 (t, J=6.0 Hz, 2H), 3.69 (s, 3H), 2.94 (t, J=6.0 Hz, 2H), 2.29 (s, 3H), 2.06 (s, 6H), 1.41 (t, J=6.8 Hz, 3H). MS m/z $[M+H]^+$ 574.1.

Method 2

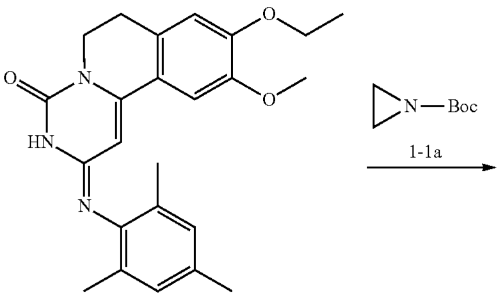

BB-1

-continued

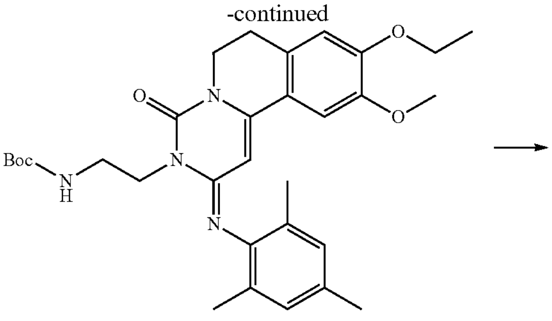

1-2a

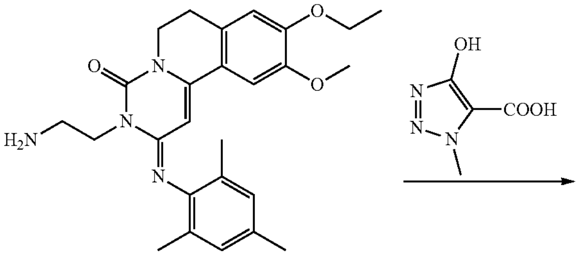

BB-4

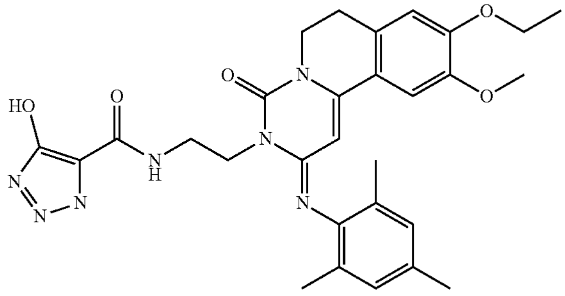

(I)

Step One: Preparation of Compound 1-1a

N-Boc-ethanolamine (50 g, 48.08 mL) and p-toluenesulfonyl chloride (70.96 g) were dissolved in methyl tert-butyl ether (500 mL), potassium hydroxide (52.21 g) was added, and the mixture was heated to 80° C. and refluxed for 4 h. The mixture was cooled to room temperature and poured into a mixture of ice and water (1000 mL) to separate the organic phases. The aqueous phase was extracted with methyl tert-butyl ether (100 mL×2). The organic phases were combined, washed with cold water (1000 mL), dried over anhydrous sodium sulfate, and filtered to remove the desiccant. The filtrate was concentrated under reduced pressure to remove the solvent to give crude product 1-1a (28.5 g) in the form of a yellow oily liquid, which was directly used in the next step without purification.

$^1$H NMR (400 MHz, CHLOROFORM-d) δ (ppm) 2.15 (s, 4H), 1.47 (s, 9H).

Step Two: Preparation of Compound 1-2a

Compound BB-1 (2 g) and compound 1-1a (4.24 g) were dissolved in acetonitrile (17 mL), and lithium carbonate (2.19 g) and water (3 mL) were added. The system was heated to 100° C. and stirred for 70 h. The mixture was cooled, let stand, and filtered to remove the precipitate. The filtrate was concentrated under reduced pressure to remove the solvent and mixed with 50 mL of water. The mixture was extracted with ethyl acetate (20 mL×3). The organic phases were combined, washed with 0.5 M sodium hydroxide solution (100 mL), dried over anhydrous sodium sulfate and filtered. The filtrate was concentrated under reduced pressure to remove the solvent to give a crude product. The crude product was separated and purified by column chromatography to give the target compound 1-2a (1.08 g) in the form of a pale yellow solid.

MS-ESI (m/z): 549.2 $[M+1]^+$ $^1$H NMR (400 MHz, METHANOL-$d_4$) δ (ppm) 6.91 (s, 2H), 6.85 (s, 1H), 6.75 (s, 1H), 5.49 (s, 1H), 4.36 (t, J=5.9 Hz, 2H), 4.09 (q, J=7.0 Hz, 2H), 4.00 (t, J=6.1 Hz, 2H), 3.68 (s, 3H), 3.56-3.48 (m, 2H), 2.91 (t, J=6.3 Hz, 2H), 2.27 (s, 3H), 2.06 (s, 6H), 1.39 (s, 12H).

Step Three: Preparation of Compound BB-4

Compound 1-2a (1 g) and 4 M hydrogen chloride in methanol (20 mL) were mixed uniformly. The system was heated to 60° C. and stirred for 2 h. The mixture was concentrated under reduced pressure to remove the solvent to give a crude product in the form of a pale yellow oily liquid. 20 mL of petroleum ether and 5 mL of ethyl acetate were added to the crude product. The mixture was stirred for 30 min and then filtered. The solid was collected and dried to give the target compound BB-4 (810 mg, 91.63% yield) in the form of a pale yellow solid.

$^1$H NMR (400 MHz, METHANOL-$d_4$) δ (ppm) 7.16 (s, 2H), 6.98 (s, 1H), 6.80 (s, 1H), 5.68 (s, 1H), 4.72 (br s, 2H), 4.22 (br s, 2H), 4.16 (q, J=7.0 Hz, 2H), 3.69 (s, 3H), 3.48 (br s, 2H), 3.08 (br s, 2H), 2.37 (s, 3H), 2.30 (s, 6H), 1.43 (t, J=7.0 Hz, 3H).

Step Four: Preparation of Compound (I)

5-Hydroxy-3-methyl-1,2,3-triazole-4-carboxylic acid (18.50 mg) was dissolved in DCM (1 mL) at 20° C. HATU (8.80 mg) and triethylamine (57.40 pt) were added and the mixture was stirred for 2 h. Compound BB-4 (50 mg) was added and the system was stirred at the temperature for 16 h. The mixture was diluted to 10 mL with DCM, then washed with water (30 mL×3), dried over anhydrous sodium sulfate, and filtered to remove the desiccant, and the filtrate was concentrated under reduced pressure to remove the solvent to give a crude product. The crude product was separated and purified by prep-HPLC to give the target compound of formula (I) (22 mg, 37.2% yield) in the form of a yellow solid.

MS-ESI (m/z): 574.5 $[M+1]^+$ $^1$H NMR (400 MHz, METHANOL-$d_4$) δ (ppm) 6.94 (s, 2H), 6.87 (s, 1H), 6.75 (s, 1H), 5.51 (s, 1H), 4.47 (br t, J=6.0 Hz, 2H), 4.14 (s, 3H), 4.10 (q, J=7.0 Hz, 2H), 4.01 (br t, J=5.9 Hz, 2H), 3.85 (br t, J=5.9 Hz, 2H), 3.68 (s, 3H), 2.92 (br t, J=6.0 Hz, 2H), 2.29 (s, 3H), 2.05 (s, 6H), 1.41 (t, J=6.9 Hz, 3H).

Method 3

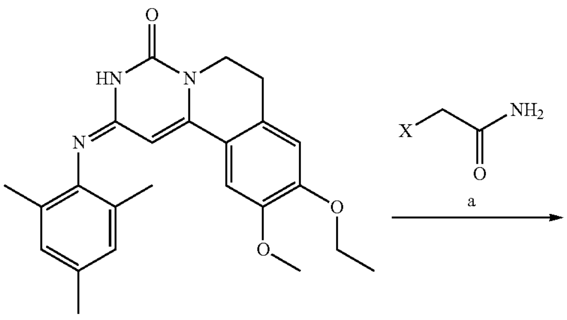

BB-1

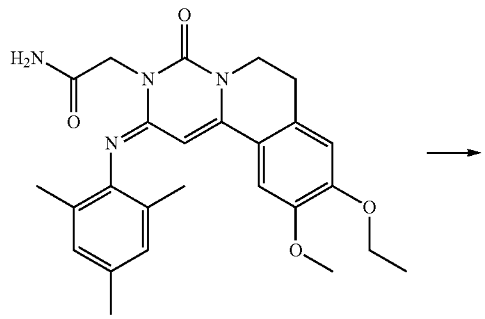

1-1b

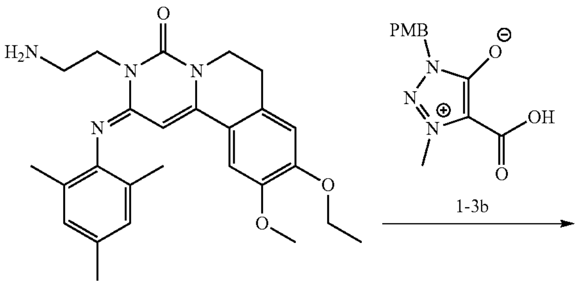

BB-4

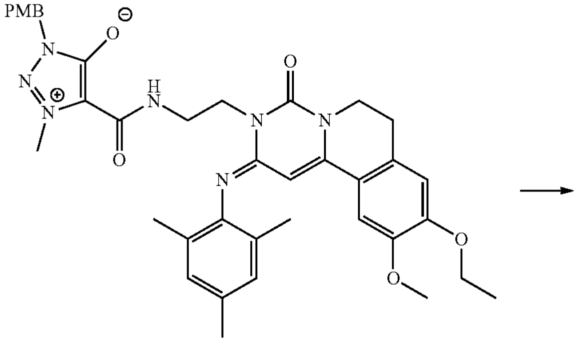

1-4b

-continued

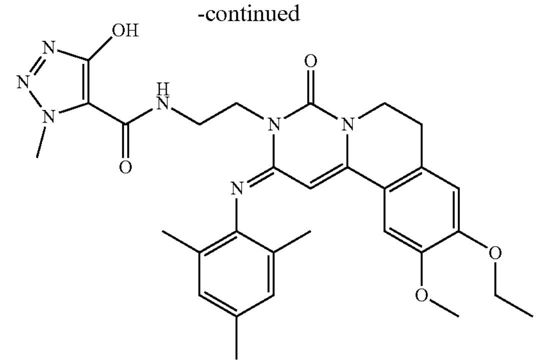

(I)

Step One: Preparation of Compound 1-1b

2-Butanone (12 L) was added to a 50-L jacketed kettle at 20° C. Compound BB-1 (615 g) and 2-bromoacetamide (612.4 g) were added with stirring. Anhydrous potassium phosphate (1.57 kg) and sodium iodide (665.4 g) were added to the system. The reaction system was heated to 90° C. and stirred for 18 h in nitrogen atmosphere. The reaction mixture was cooled to room temperature before water (12 L) was added. The mixture was stirred for 1 h, and filtered to give a solid. The resulting solid was dried in vacuum to give the target compound 1-1b (575 g, 81.96% yield) in the form of a yellow solid.

MS-ESI (m/z): 463.23 $[M+1]^+$ $^1$H NMR (400 MHz, DMSO-$d_6$) δ=7.49 (br s, 1H), 7.06 (br s, 1H), 6.95 (s, 1H), 6.82 (s, 2H), 6.69 (s, 1H), 5.33 (s, 1H), 4.66 (s, 2H), 4.07 (q, J=6.9 Hz, 2H), 3.91 (br t, J=6.0 Hz, 2H), 3.63 (s, 3H), 2.90 (br t, J=5.9 Hz, 2H), 2.20 (s, 3H), 1.92 (s, 6H), 1.33 (t, J=7.0 Hz, 3H).

Step Two: Preparation of Compound BB-4

Tetrahydrofuran (8.6 L) was added to a 50-L dry jacketed kettle at 20° C., and a borane-dimethyl sulfide solution (10 M, 950 mL) was added dropwise to the kettle with stirring. After addition, the system was cooled to 0° C. before compound 1-1b (440 g) was added. The cooling unit was turned off. The mixture was naturally warmed to 20-25° C., and stirred for another 18 h. The reaction mixture was cooled to 0° C., methanol (~1.5 L) was added dropwise to quench the reaction until no bubbles were generated, and a 3 M hydrochloric acid solution (~800 mL) was added dropwise to the reaction mixture to adjust to pH 2-3. The reaction mixture was concentrated under reduced pressure to remove the solvent. The residue was dissolved in dichloromethane, and a saturated sodium bicarbonate solution was added to adjust the mixture to pH 7-8. The phases were separated, and the aqueous phase was extracted with dichloromethane (3000 mL×2). The organic phases were combined, dried over anhydrous sodium sulfate, filtered to remove the desiccant, and concentrated under reduced pressure. The resulting product was separated and purified by flash column chromatography to give the target compound BB-4 (125 g).

MS-ESI (m/z): 449.25 $[M+1]^+$ $^1$H NMR (400 MHz, DMSO-$d_6$) δ=7.91 (br s, 2H), 6.96 (s, 1H), 6.87 (s, 2H), 6.69 (s, 1H), 5.35 (s, 1H), 4.41 (br t, J=5.8 Hz, 2H), 4.07 (q, J=6.8 Hz, 2H), 3.92 (br t, J=5.8 Hz, 2H), 3.63 (s, 3H), 3.21 (br s, 2H), 2.90 (br t, J=5.8 Hz, 2H), 2.22 (s, 3H), 1.98 (s, 6H), 1.33 (t, J=7.0 Hz, 3H).

Step Three: Preparation of Compound 1-4b

Compound 1-3b (68.68 g) was dissolved in dichloromethane (700 mL) at 20° C., N,N-carbonyldiimidazole (61.56 g) was added, and the system was stirred at 25° C. for 5 h. The mixture was washed with saturated brine (700 mL), dried over anhydrous sodium sulfate, filtered, and concentrated under reduced pressure. The residue was dissolved in DMF (675 mL), compound BB-4 (95 g) was added in portions, and the system was stirred at 20-25° C. for 18 h. Methanol (675 mL) was added to the reaction mixture, and the mixture was stirred for 1 h and filtered to give the target compound 1-4b (120 g, 81.49% yield).

MS-ESI (m/z): 694.33 $[M+1]^+$ $^1$H NMR (400 MHz, DMSO-$d_6$) δ=8.36 (t, J=6.1 Hz, 1H), 7.26 (d, J=8.6 Hz, 2H), 6.96-6.87 (m, 3H), 6.82 (s, 2H), 6.66 (s, 1H), 5.14 (s, 2H), 4.31 (br t, J=6.3 Hz, 2H), 4.16 (s, 3H), 4.06 (q, J=6.8 Hz, 2H), 3.86 (br t, J=5.8 Hz, 2H), 3.75-3.66 (m, 5H), 3.62 (s, 3H), 2.86 (br t, J=5.9 Hz, 2H), 2.21 (s, 3H), 1.91 (s, 6H), 1.33 (t, J=6.9 Hz, 3H).

Step Four: Preparation of Compound (I)

Compound 1-4b (120 g) was dissolved in a mixed solvent of trifluoroacetic acid (1000 mL) and glacial acetic acid (200 mL) at 20° C., and the system was heated to 90-100° C. and stirred for 48 h. The reaction mixture was concentrated under reduced pressure to remove most of the solvent. The residue was dissolved in DCM (1000 mL), and a saturated sodium bicarbonate solution was added to adjust to pH 7-8. The organic phase and the aqueous phase were separated. The aqueous phase was extracted with DCM (1000 mL×3). The organic phases were combined, dried over anhydrous sodium sulfate, and filtered to remove the desiccant. The filtrate was concentrated under reduced pressure to remove the solvent to give the target compound of formula (I) (80 g, 80.60% yield). MS-ESI (m/z): 574.27 $[M+1]^+$ $^1$H NMR (400 MHz, DMSO-$d_6$) δ=7.73-7.65 (m, 1H), 6.94 (s, 1H), 6.84 (s, 2H), 6.66 (s, 1H), 5.32 (s, 1H), 4.35 (t, J=6.1 Hz, 2H), 4.12-4.01 (m, 5H), 3.88 (t, J=6.1 Hz, 2H), 3.70 (q, J=6.1 Hz, 2H), 3.62 (s, 3H), 2.87 (br t, J=6.0 Hz, 2H), 2.21 (s, 3H), 1.93 (s, 6H), 1.33 (t, J=6.9 Hz, 3H), 0.90-0.90 (m, 1H).

Example 2: Preparation of Crystalline Form a of Compound of Formula (I)

Figure 2:
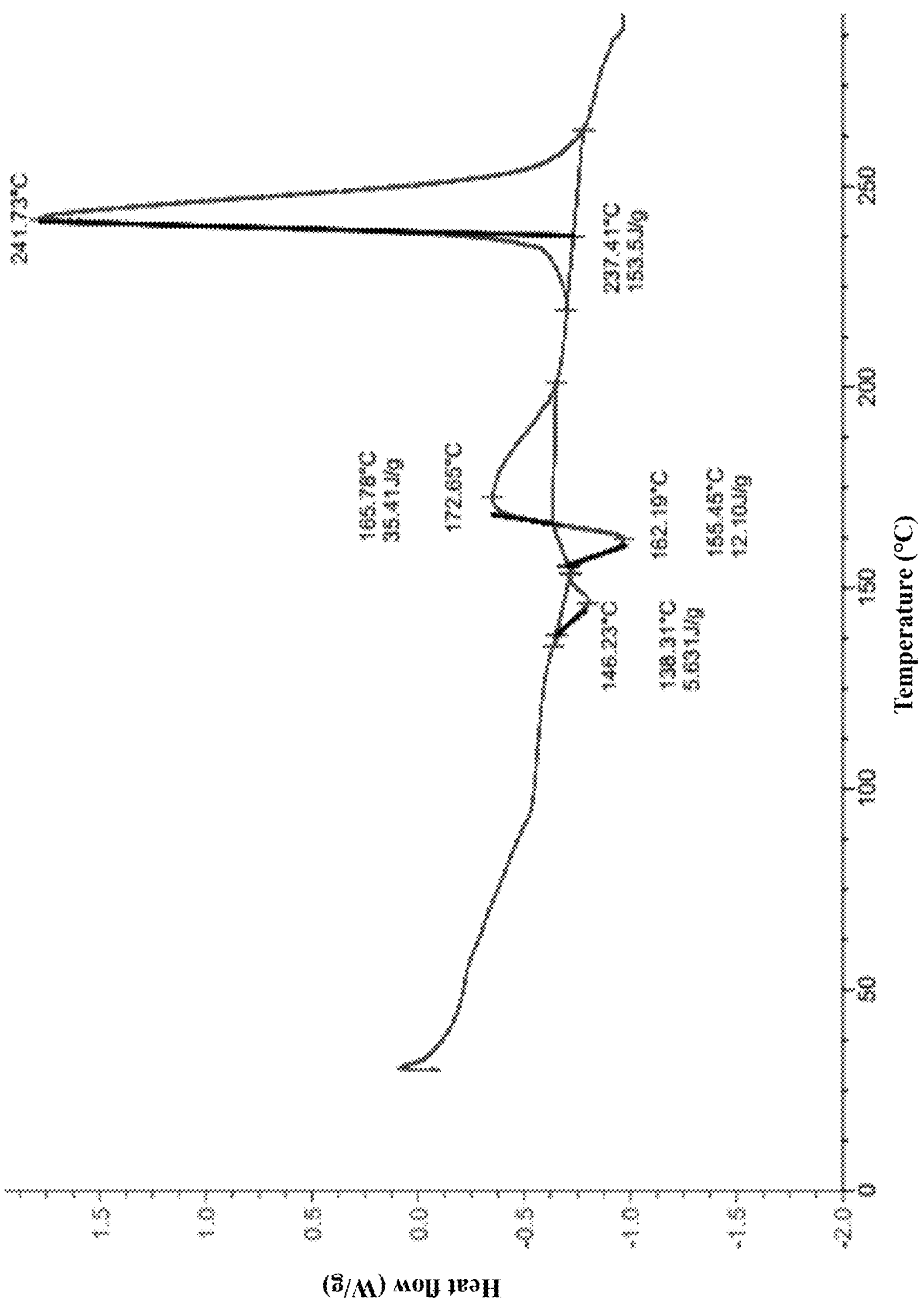
FIG. 2 is a DSC pattern of the crystalline form A of the compound of formula (I)
Figure 3:
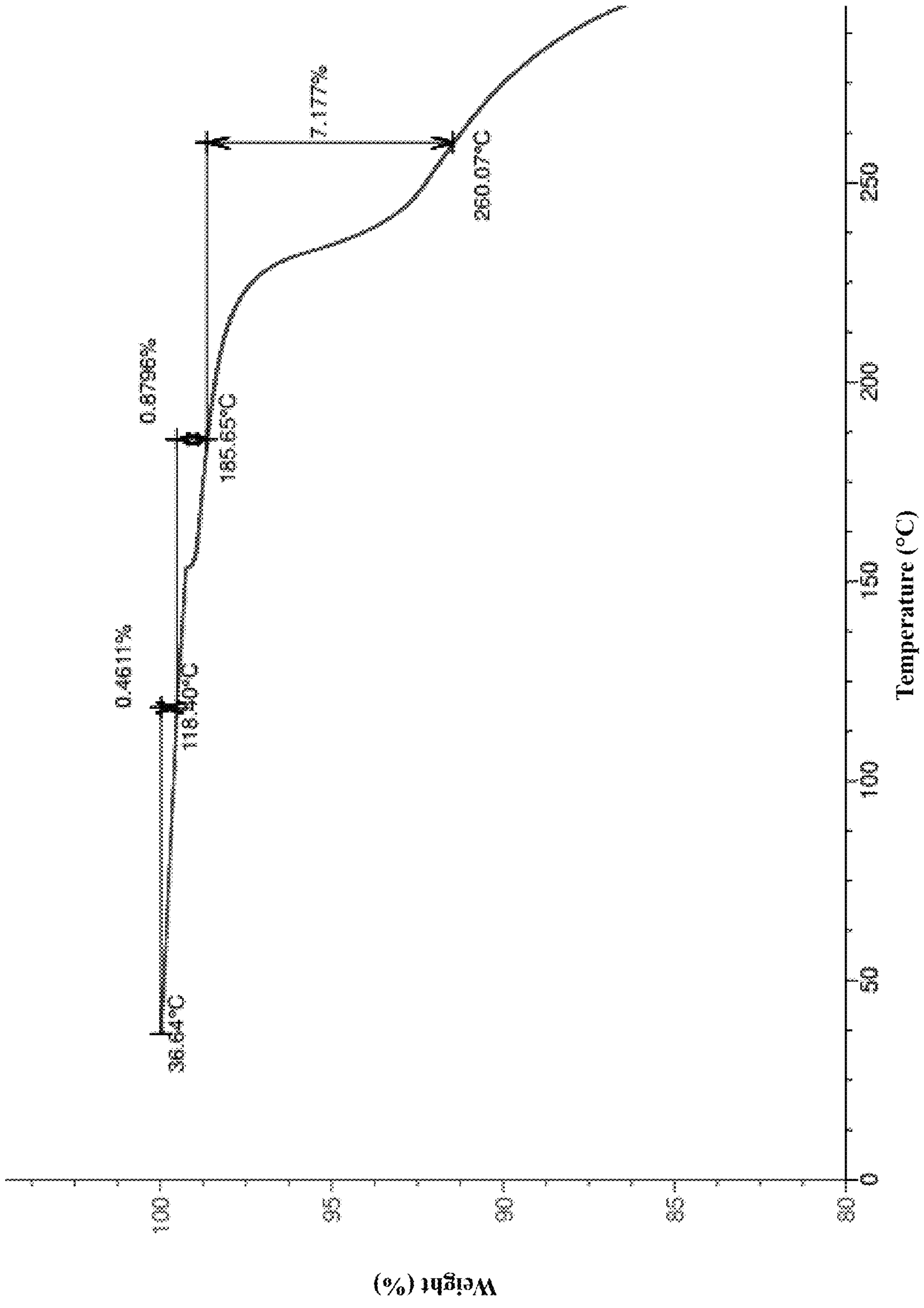
FIG. 3 is a TGA pattern of the crystalline form A of the compound of formula (I)

50 mg of the compound of formula (I) was added to a 4-mL glass bottle, 1 mL of anhydrous methanol was added, and the mixture was heated to 40° C. and stirred for 48 h. The mixture was naturally cooled to room temperature, centrifuged to separate the solid, and dried in vacuum to give 34 mg of solid, namely the crystalline form A. The XRPD pattern is shown in FIG. 1, the DSC pattern is shown in FIG. 2, and the TGA pattern is shown in FIG. 3.

Example 3: Preparation of Crystalline Form B of Compound of Formula (I)

Figure 4:
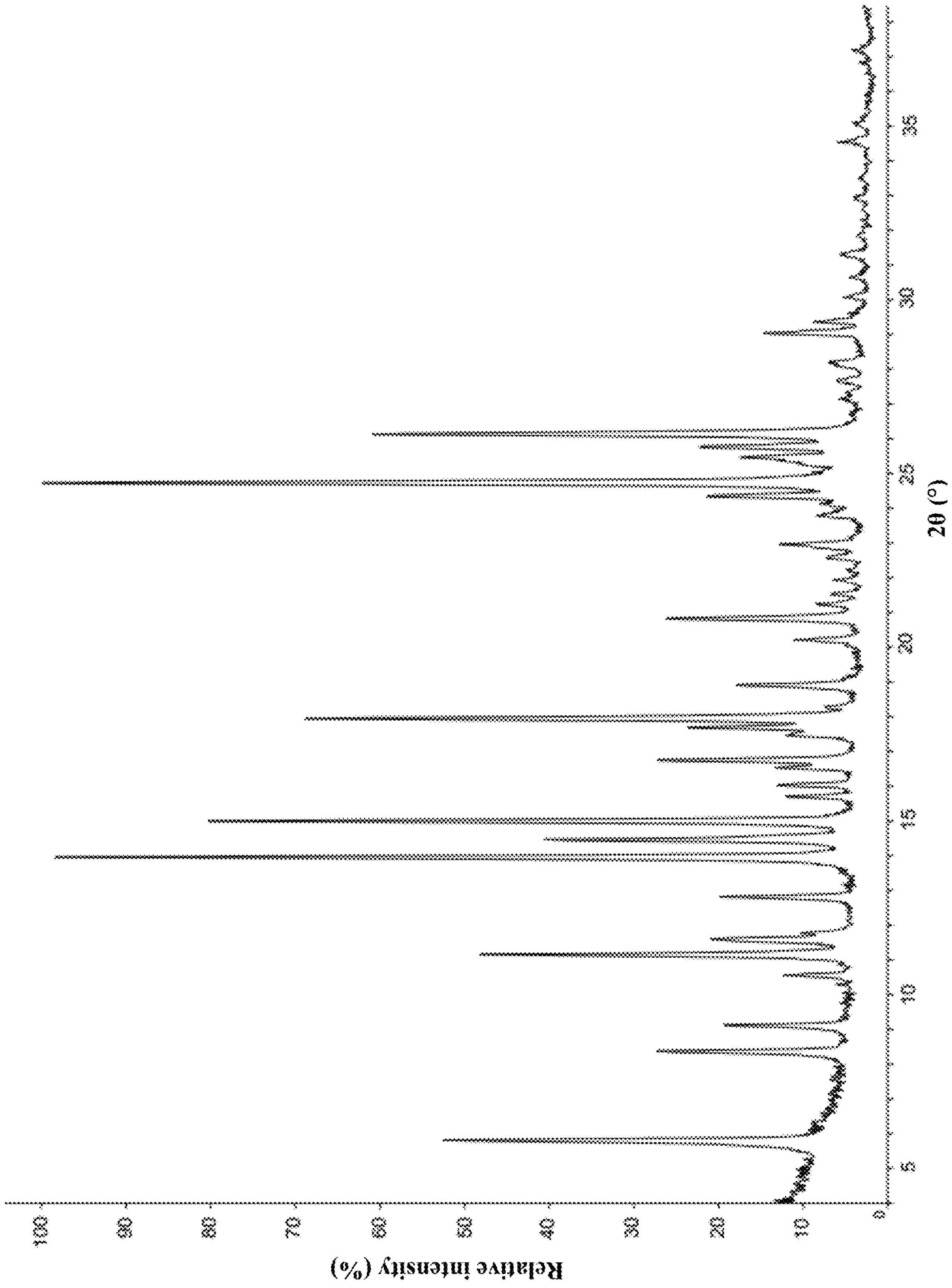
FIG. 4 is an XRPD pattern of a crystalline form B of the compound of formula (I)
Figure 5:
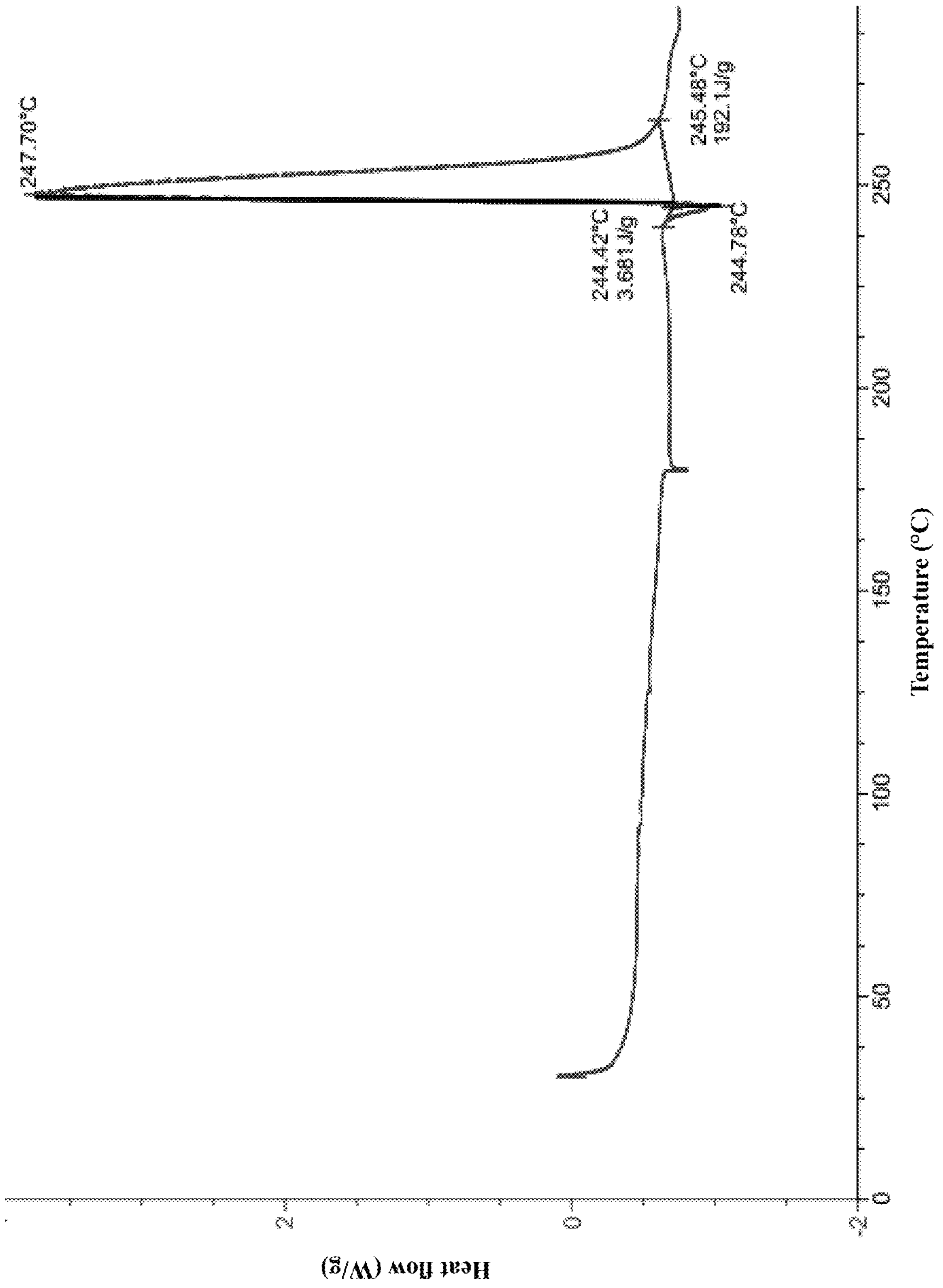
FIG. 5 is a DSC pattern of the crystalline form B of the compound of formula (I)
Figure 6:
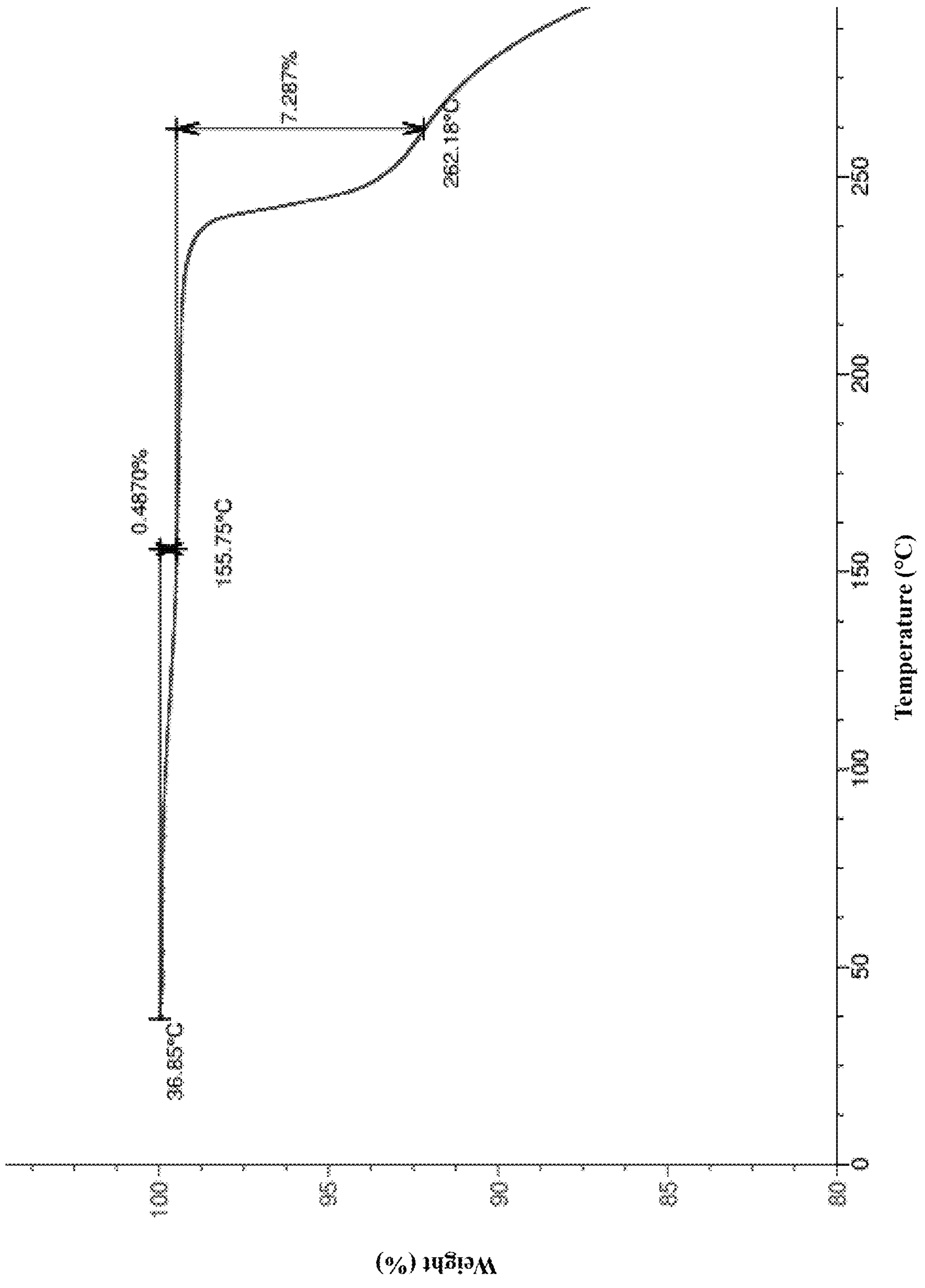
FIG. 6 is a TGA pattern of the crystalline form B of the compound of formula (I)

50 mg of the compound of formula (I) was added to a 4-mL glass bottle, 1 mL of anhydrous ethanol and 0.2 mL of water were added, and the mixture was heated to 40° C. and stirred for 48 h. The mixture was naturally cooled to room temperature, centrifuged to separate the solid, and dried in vacuum to give 46 mg of solid, namely the crystalline form B. The XRPD pattern is shown in FIG. 4, the DSC pattern is shown in FIG. 5, and the TGA pattern is shown in FIG. 6.

Example 4: Preparation of Crystalline Form C of Compound of Formula (I)

Figure 7:
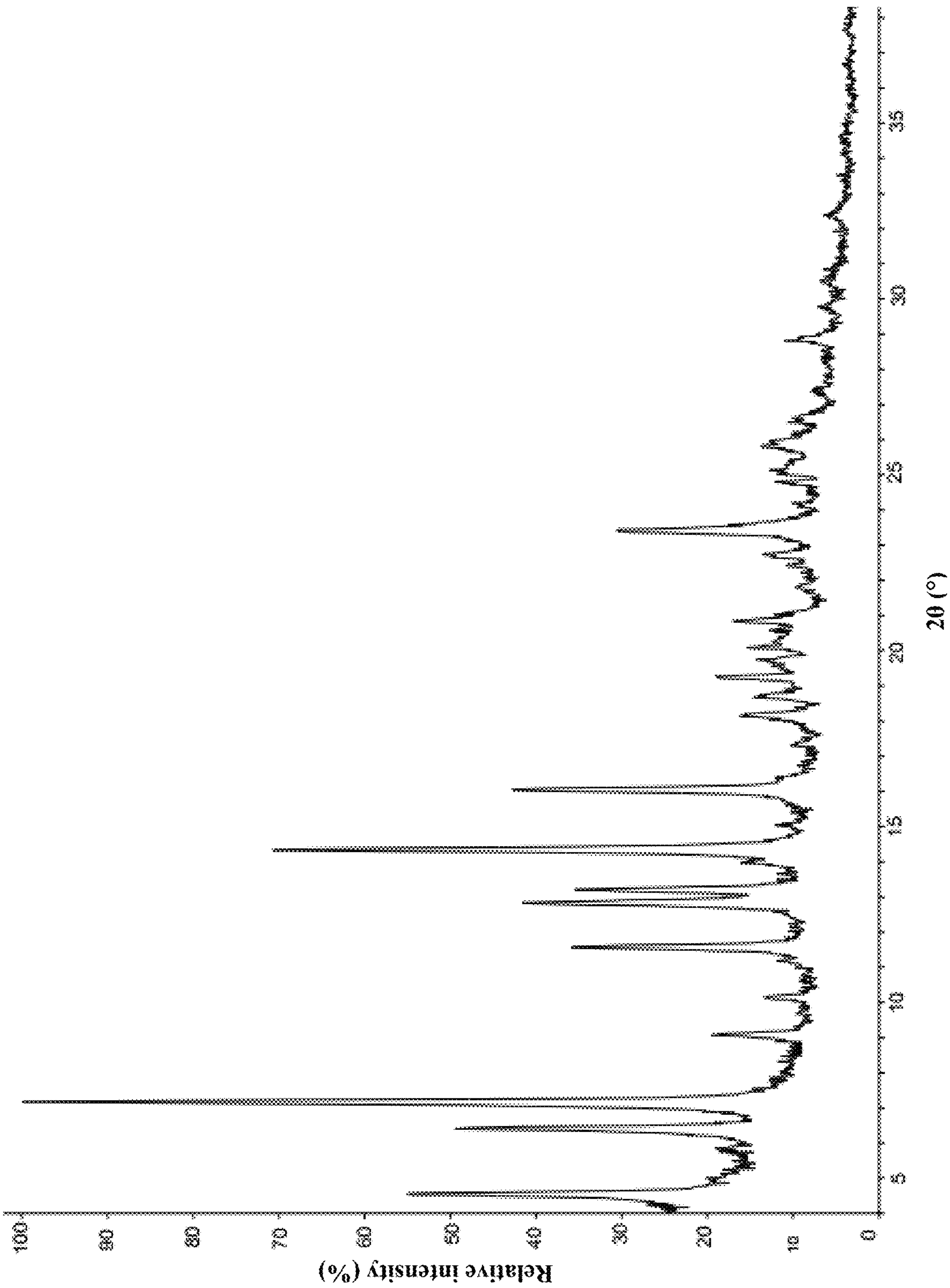
FIG. 7 is an XRPD pattern of a crystalline form C of the compound of formula (I)
Figure 8:
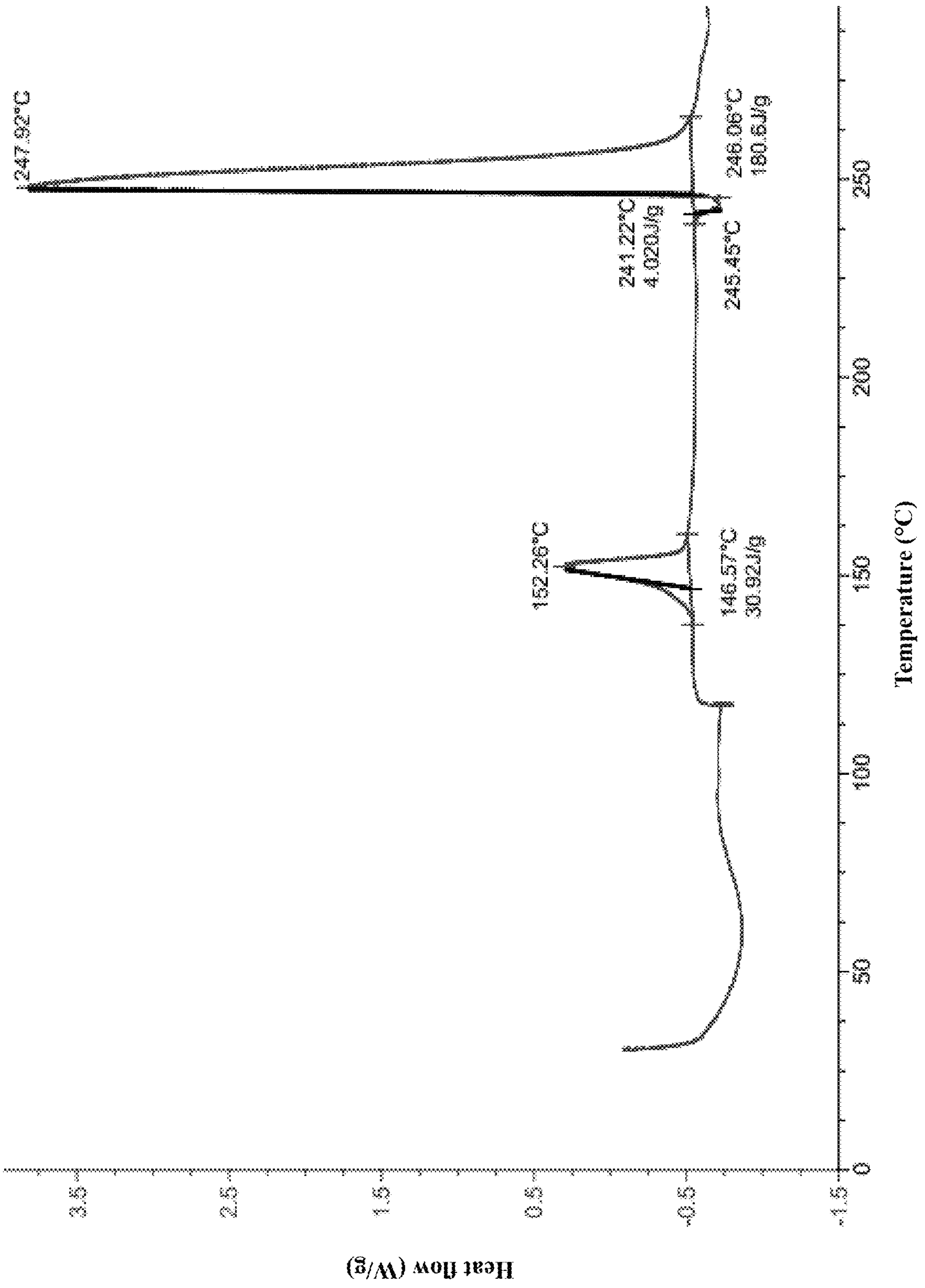
FIG. 8 is a DSC pattern of the crystalline form C of the compound of formula (I)
Figure 9:
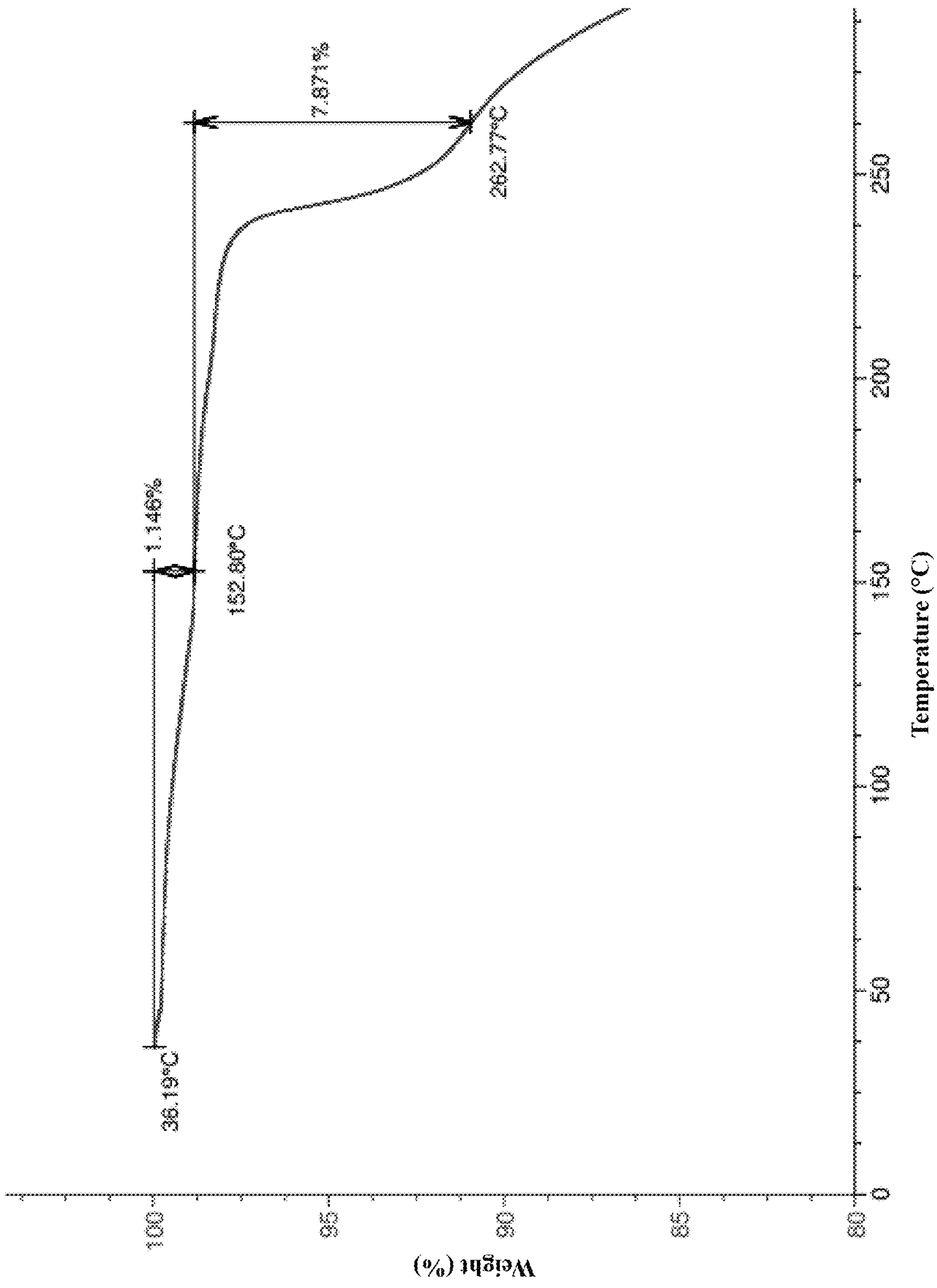
FIG. 9 is a TGA pattern of the crystalline form C of the compound of formula (I)

50 mg of the compound of formula (I) was added to a 4-mL glass bottle, 1 mL of acetonitrile was added, and the mixture was heated to 40° C. and stirred for 48 h. The mixture was naturally cooled to room temperature, centrifuged to separate the solid, and dried in vacuum to give 37 mg of solid, i.e., the crystalline form C. The XRPD pattern is shown in FIG. 7, the DSC pattern is shown in FIG. 8, and the TGA pattern is shown in FIG. 9.

Example 5: Preparation of Salt of Compound of Formula (I)

100 mg of the compound of formula (I) was added to a 4 mL glass bottle, and 2 mL of anhydrous tetrahydrofuran was added. The mixture was heated to 70° C. and stirred for 1 h to fully dissolve the compound, and then cooled to 40° C. A solution prepared from the corresponding acid or base (the specific chemicals and amounts are shown in Table 8) and 0.1 mL of water was added to the mixture, and the mixture was stirred at the temperature for 12 h. The mixture was centrifuged to separate a solid precipitate, and the precipitate was dried in vacuum to give a solid, i.e., the corresponding salt of the crystalline form of the compound of formula (I).

TABLE 8

Preparation of salt forms

Figure 10:
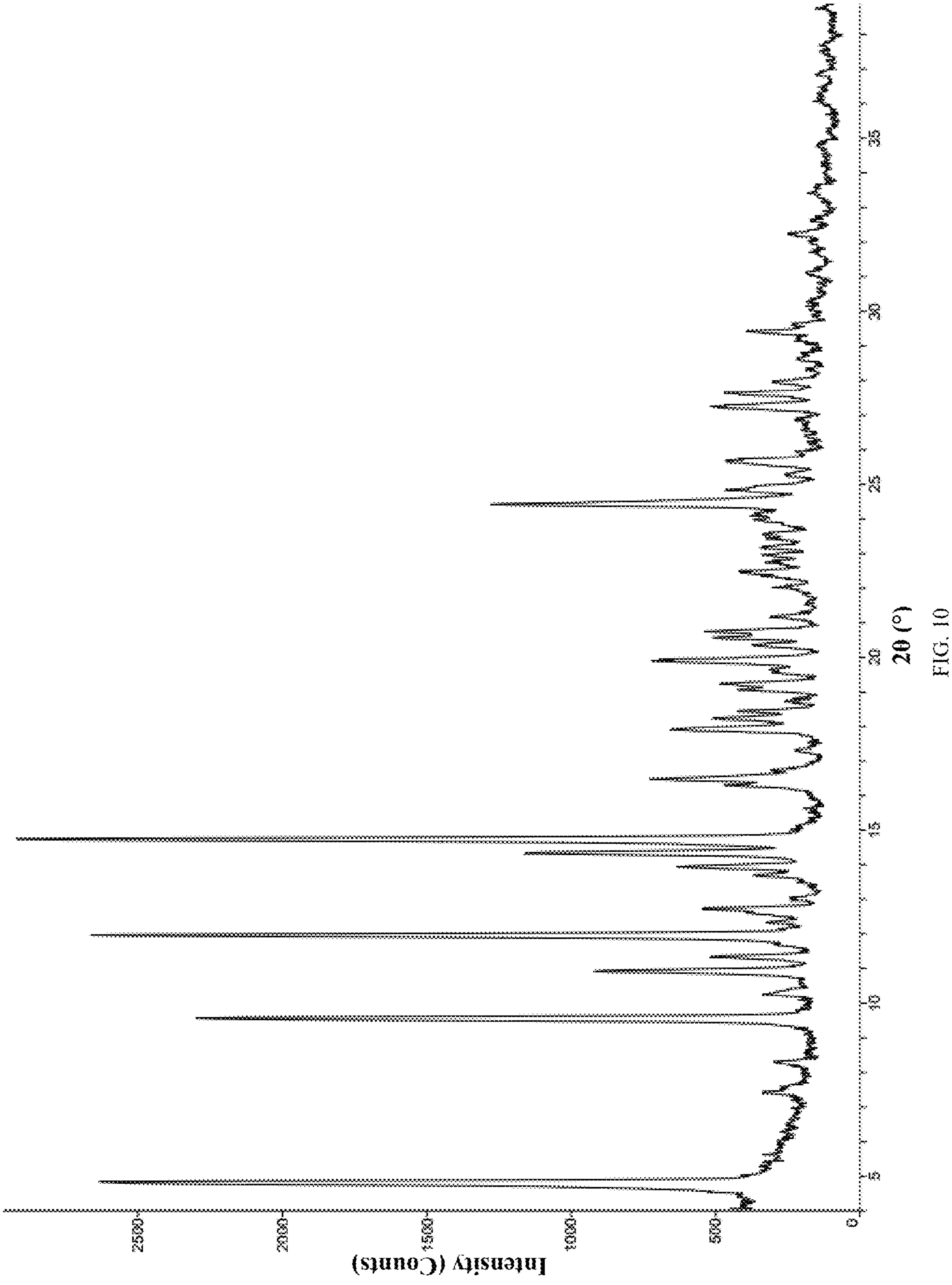
FIG. 10 is an XRPD pattern of a crystalline form of the compound of formula (II)
Figure 11:
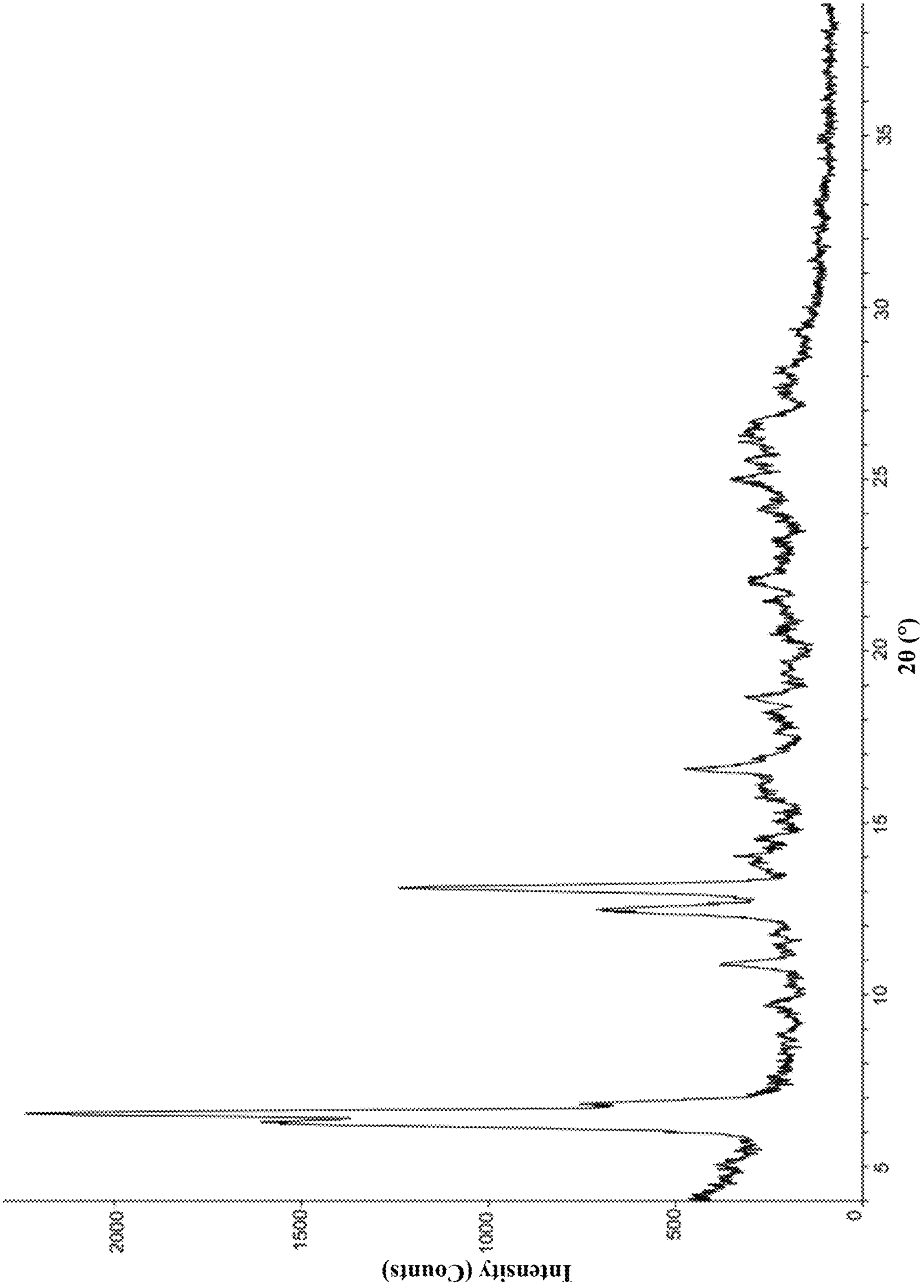
FIG. 11 is an XRPD pattern of a crystalline form of the compound of formula (III)
Figure 12:
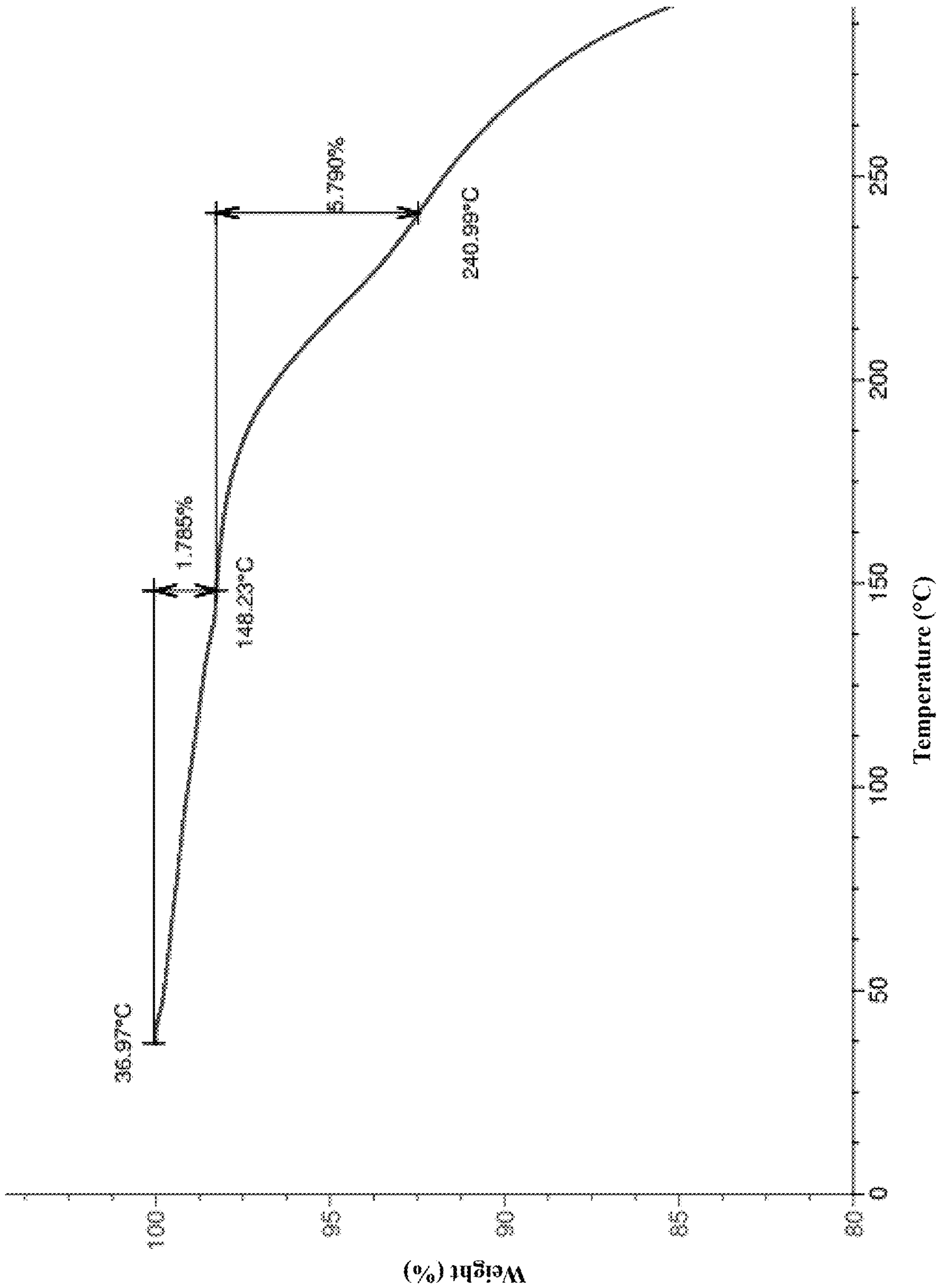
FIG. 12 is a TGA pattern of the crystalline form of the compound of formula (III)
Figure 16:
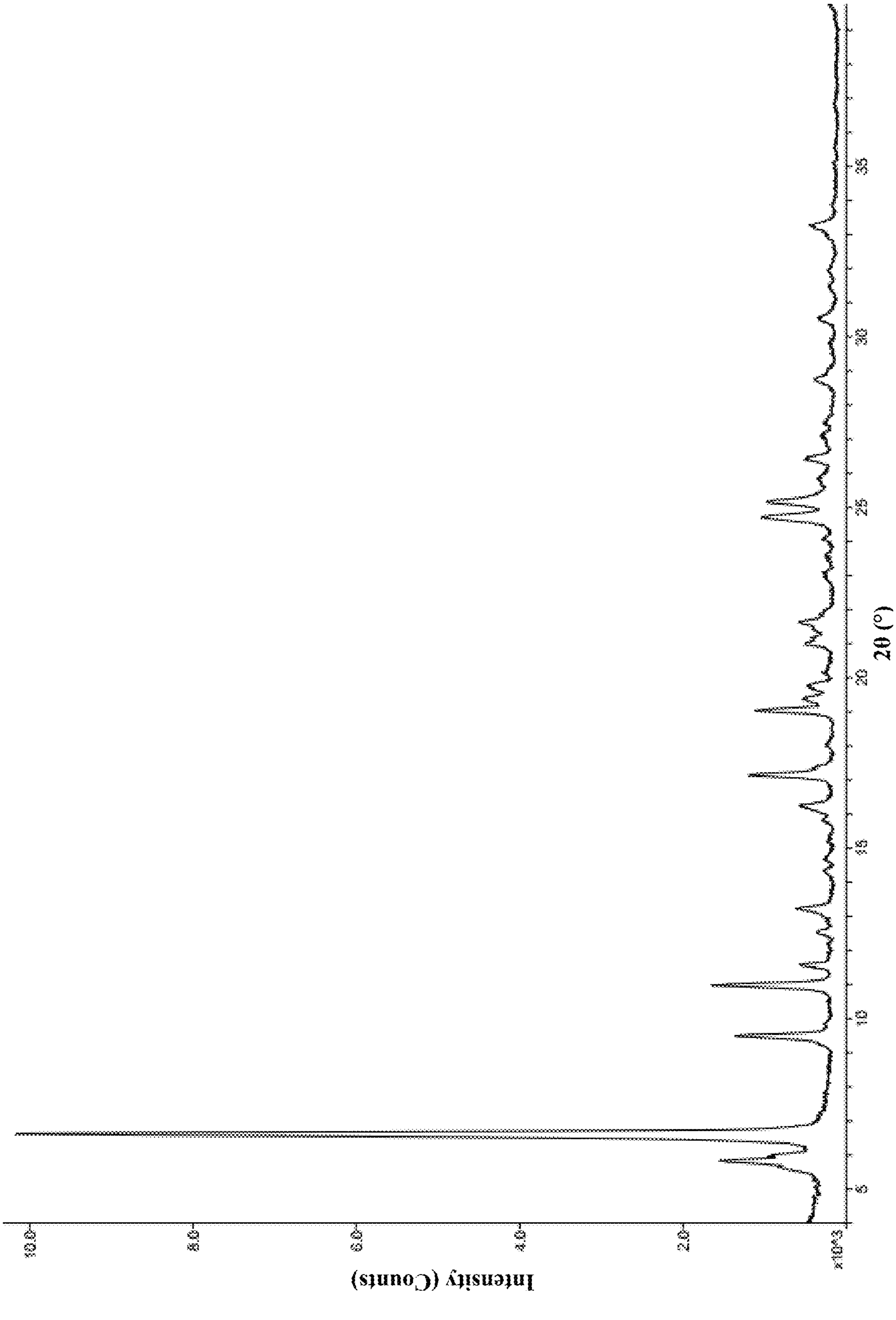
FIG. 16 is an XRPD pattern of a crystalline form of the compound of formula (V)
Figure 17:
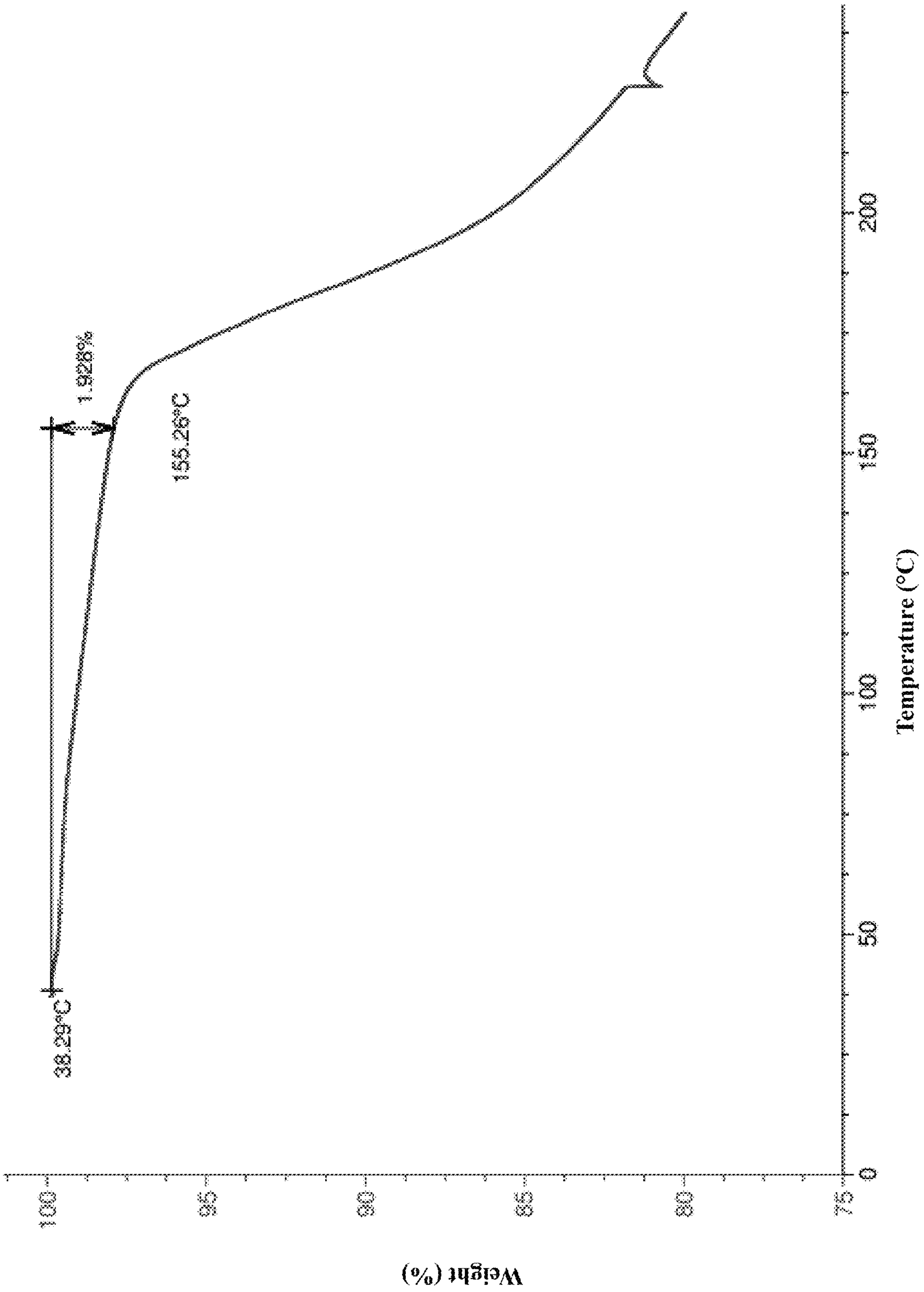
FIG. 17 is a TGA pattern of the crystalline form of the compound of formula (V)

| Salt form | Acid/base | Amount | $^1$HNMR | XRPD/ TGA/DSC characterization data |
|---|---|---|---|---|
| 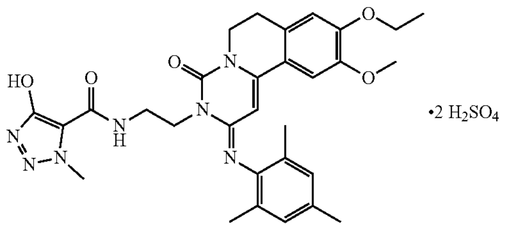 (II) | 98% sulfuric acid | 9.7 μL | $^1$H NMR (400 MHz, METHANOL-$d_4$) δ = 7.15 (s, 2H), 6.98 (s, 1H), 6.81 (s, 1H), 5.68 (s, 1H), 4.52 (t, J = 6.4 Hz, 2H), 4.21-4.10 (m, 7H), 3.89 (t, J = 6.4 Hz, 2H), 3.70 (s, 3H), 3.03 (t, J = 6.5 Hz, 2H), 2.38 (s, 3H), 2.26 (s, 6H), 1.43 (t, J = 7.0 Hz, 3H) | The XRPD pattern of the crystalline form thereof is shown in FIG. 10. |
| 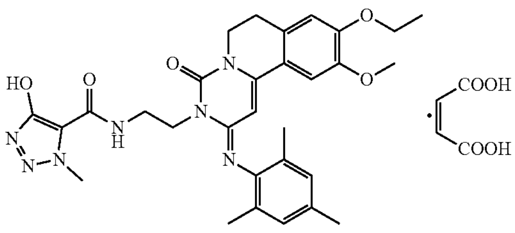 (V) | Maleic acid | 21 mg | $^1$H NMR (400 MHz, METHANOL-d4) δ = 7.13 (s, 2H), 6.96 (s, 1H), 6.80 (s, 1H), 6.26 (s, 2H), 5.66 (s, 1H), 4.52 (t, J = 6.4 Hz, 2H), 4.20-4.10 (m, 6H), 3.89 (t, J = 6.4 Hz, 2H), 3.70 (s, 3H), 3.02 (t, J = 6.4 Hz, 2H), 2.37 (s, 3H), 2.24 (s, 6H), 1.43 (t, J = 7.0 Hz, 3H) | The XRPD pattern of the crystalline form thereof is shown in FIG. 16, and the TGA pattern is shown in FIG. 17. |
| 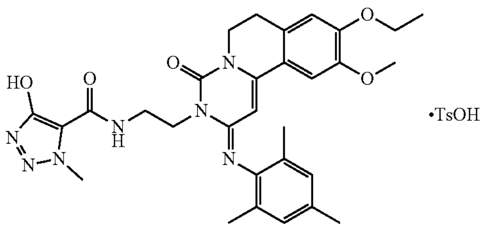 (III) | p-Toluenesulfonic acid | 31 mg | $^1$H NMR (400 MHz, METHANOL-d4) δ = 7.70 (d, J = 8.1 Hz, 2H), 7.23 (d, J = 8.0 Hz, 2H), 7.15 (s, 2H), 6.97 (s, 1H), 6.80 (s, 1H), 5.67 (s, 1H), 4.52 (t, J = 6.4 Hz, 2H), 4.21-4.10 (m, 7H), 3.89 (t, J = 6.4 Hz, 2H), 3.70 (s, 3H), 3.02 (t, J = 6.5 Hz, 2H), 2.38 (s, 3H), 2.37 (s, 3H), 2.25 (s, 6H), 1.43 (t, J = 7.0 Hz, 3H) | The XRPD pattern of the crystalline form thereof is shown in FIG. 11, and the TGA pattern is shown in FIG. 12. |

TABLE 8-continued

Figure 13:
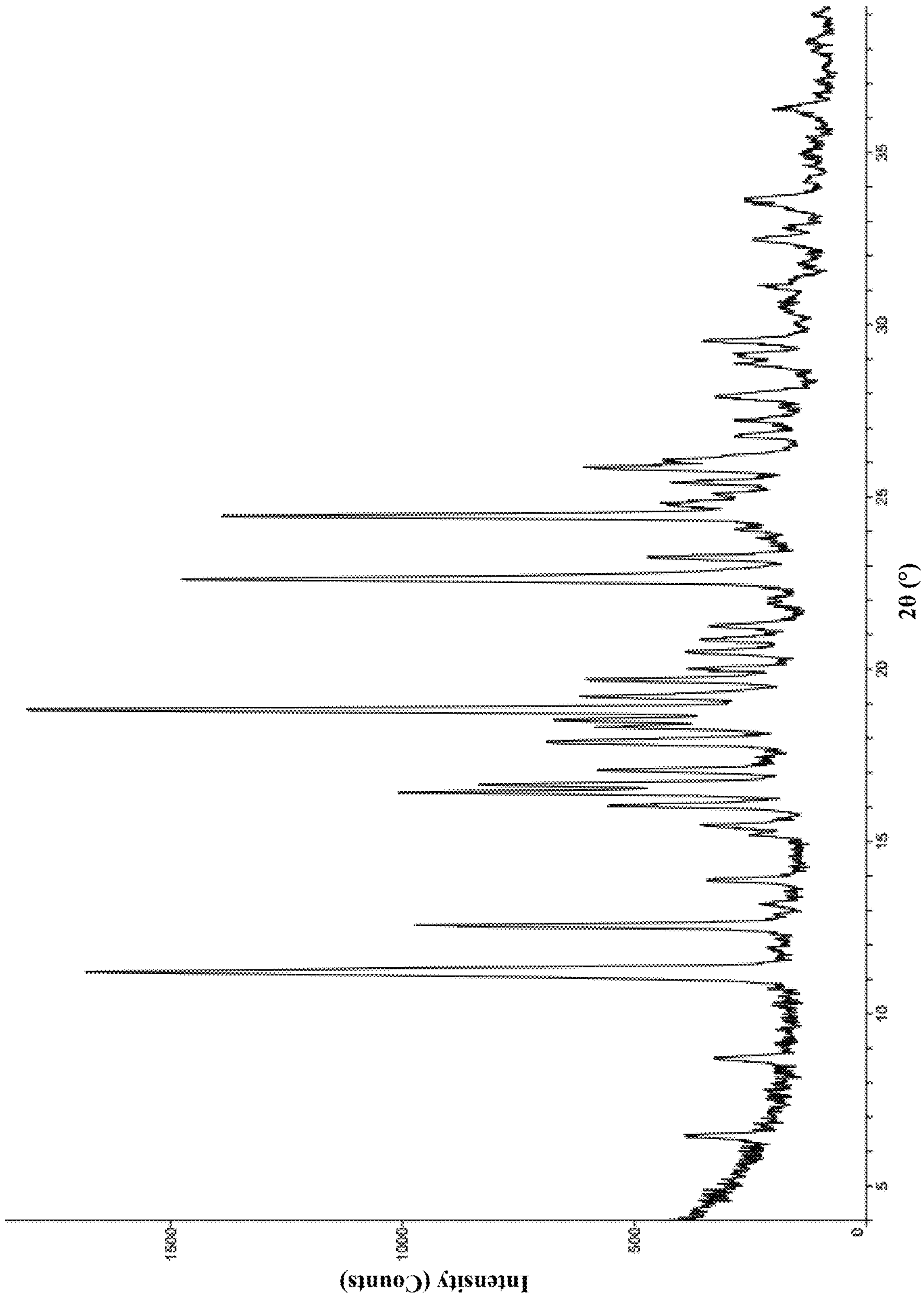
FIG. 13 is an XRPD pattern of a crystalline form of the compound of formula (IV)
Figure 14:
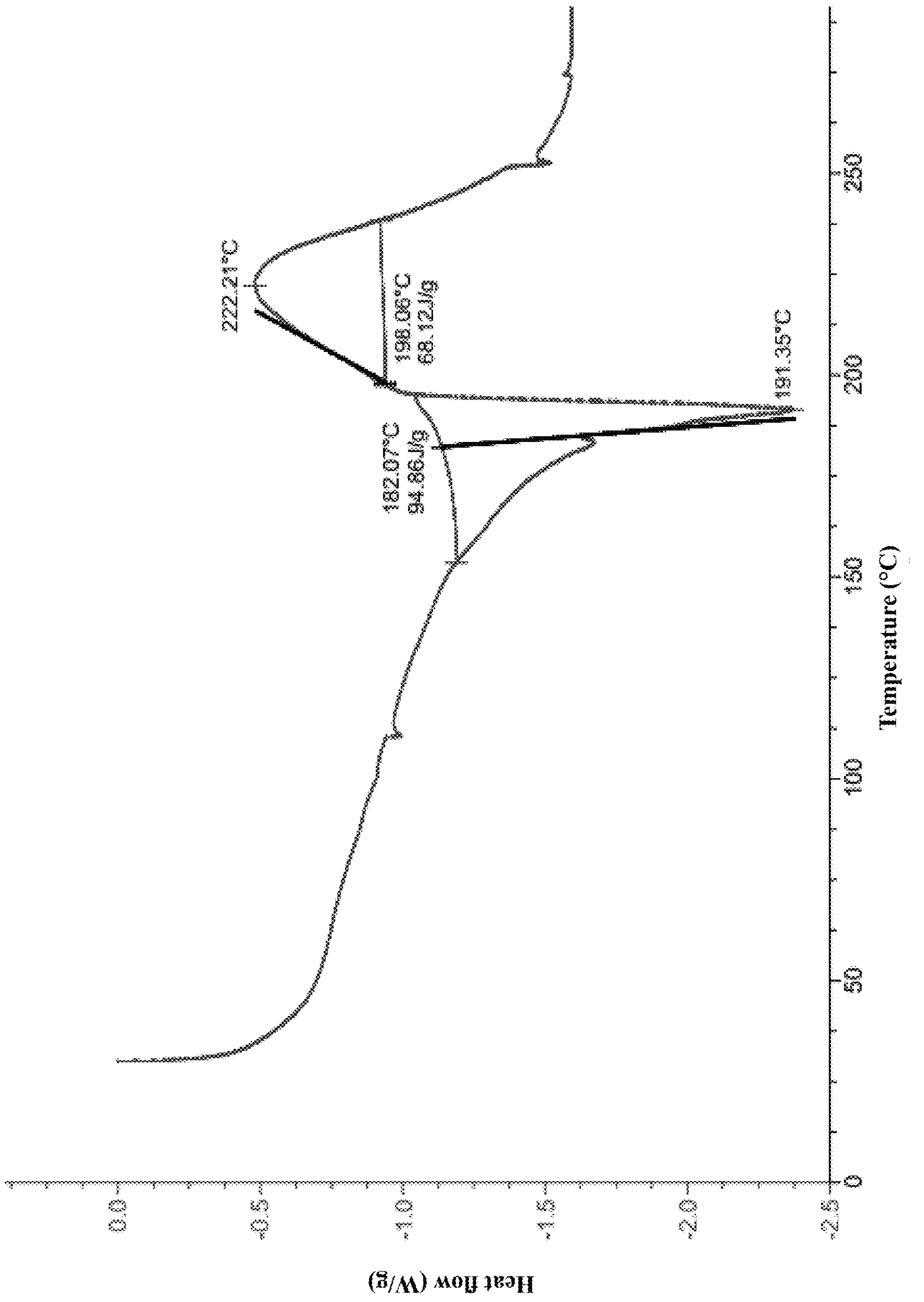
FIG. 14 is a DSC pattern of the crystalline form of the compound of formula (IV)
Figure 15:
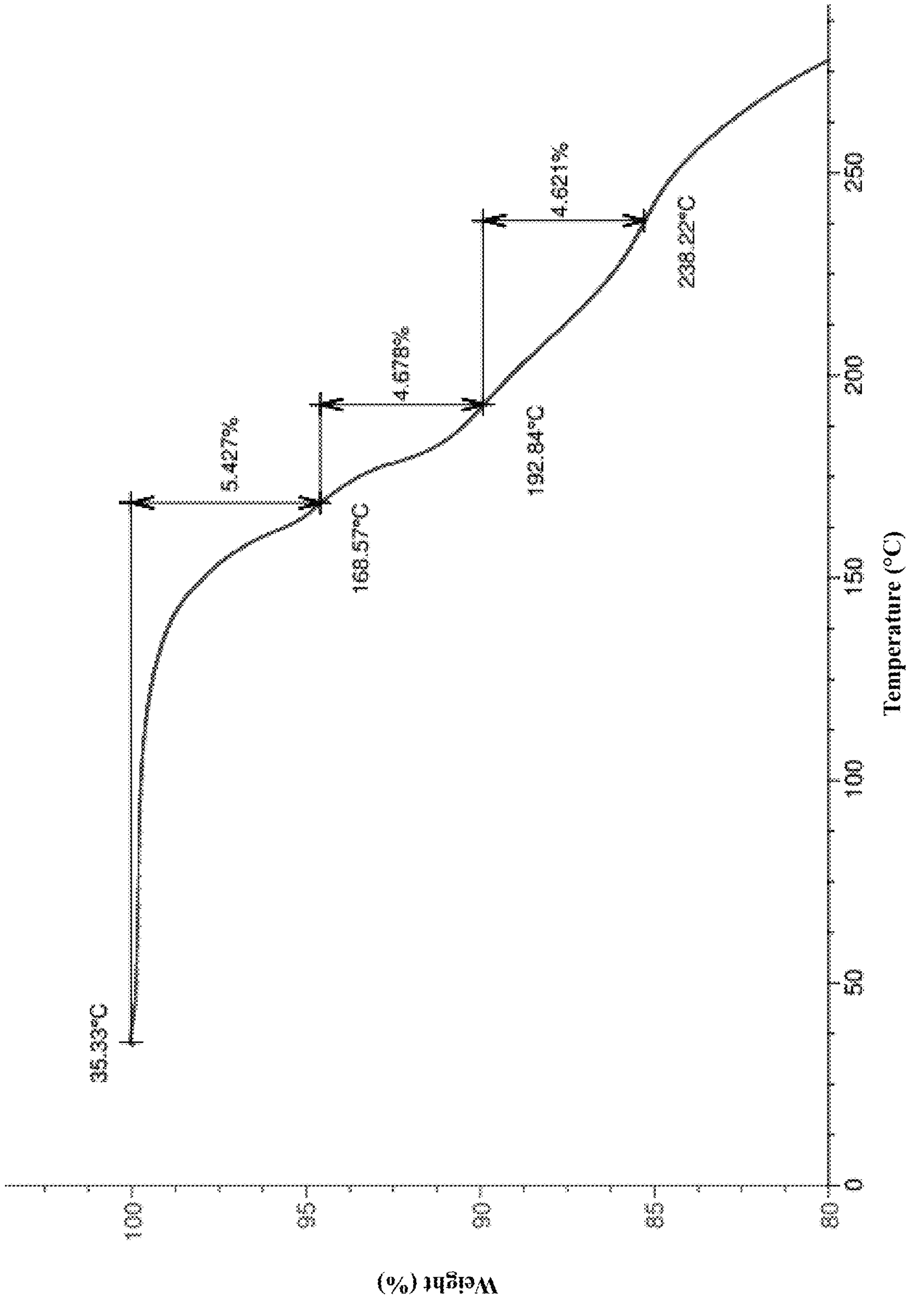
FIG. 15 is a TGA pattern of the crystalline form of the compound of formula (IV)

| Preparation of salt forms | | | | |
|---|---|---|---|---|
| Salt form | Acid/base | Amount | ¹HNMR | XRPD/ TGA/DSC characterization data |
| 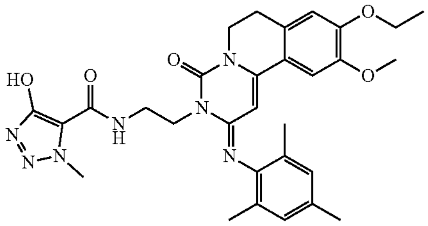 •MsOH (IV) | Methanesulfonic acid | 12 μL | ¹H NMR (400 MHz, METHANOL-d4) δ = 7.15 (s, 2H), 6.98 (s, 1H), 6.81 (s, 1H), 5.68 (s, 1H), 4.52 (t, J = 6.4 Hz, 2H), 4.22-4.12 (m, 7H), 3.89 (t, J = 6.4 Hz, 2H), 3.70 (s, 3H), 3.03 (t, J = 6.6 Hz, 2H), 2.69 (s, 3H), 2.38 (s, 3H), 2.26 (s, 6H), 1.43 (t, J = 7.0 Hz, 3H) | The XRPD pattern of the crystalline form thereof is shown in FIG. 13, the DSC pattern is shown in FIG. 14, and the TGA pattern is shown in FIG. 15. |

Example 6: Stability Study of Solid Crystalline Form B of the Compound of Formula (I) High Performance Liquid Chromatography (HPLC)

The chromatographic conditions of the HPLC method are seen in table below: Chromatographic column: Zorbax SB C-18, 4.6 mm×150 mm, 5 μm (PDS-HPLC-007)

Mobile phase A: 0.1% TFA in water

Mobile phase B: 100% ACN

Preparation of sample: the sample was dissolved in a mixed solvent of acetonitrile and water (acetonitrile: water=50:50 (v/v))

Solid Stability Testing

The stability of the compound in the following conditions was examined, and samples were taken at different time points to detect the content. About 5 mg of the crystalline form B of the compound of formula (I) was accurately weighted in duplicate, transferred to a dry and clean glass bottle, spread into a thin layer as test samples, and placed in experimental conditions of influential factors ((60° C.), (relative humidity 92.5%), illumination (total illumination of 1.2×106 Lux·hr/near UV energy of 200 w·hr/m2), (40° C., relative humidity 75%), or (60° C., relative humidity 75%)). The samples were covered with aluminum foils having holes, and thus completely exposed to the conditions. Sampling analysis was performed at 5 days, 10 days, 1 month, 2 months and 3 months. The samples were completely exposed to illumination (visible light of 1200000 Lux, UV of 200 W) at room temperature. The results are shown in Table 9.

TABLE 9

Results of solid stability sample content assay (5 d, 10 d, 1 M, 2 M and 3 M)

| RRT/Norm % | Total impurities % |
|---|---|
| Day 0 | 0.11 |
| 60° C.-5 days | 0.10 |
| 60° C.-10 days | 0.11 |
| 92.5% RH-5 days | 0.11 |
| 92.5% RH-10 days | 0.10 |
| In the dark | 0.11 |

TABLE 9-continued

Results of solid stability sample content assay (5 d, 10 d, 1 M, 2 M and 3 M)

| RRT/Norm % | Total impurities % |
|---|---|
| Illumination | 0.10 |
| 40° C.-75% RH-10 days | 0.10 |
| 60° C.-75% RH-10 days | 0.10 |
| 40° C.-75% RH-1 month | 0.10 |
| 60° C.-75% RH-1 month | 0.10 |
| 40° C.-75% RH-2 months | 0.08 |
| 40° C.-75% RH-3 months | 0.09 |

As can be seen, the crystalline form of the compound of formula (I) of the present application has good stability in the conditions of high temperature, high humidity or illumination without the increase of impurities during the test.

Example 7: Hygroscopicity Study of Crystalline Form B of Compound of Formula (I)

Instrument model: SMS DVS Advantage

Test conditions: the sample (10-20 mg, the crystalline form B prepared in Example 3) was placed in DVS sample tray for testing.

The detailed DVS parameters were as follows:

Temperature: 25° C.

Balancing: dm/dt=0.01%/min (shortest: 10 min, longest: 180 min)

Drying: drying at 0% RH for 120 min

RH (%) test gradient: 10%

Figure 18:
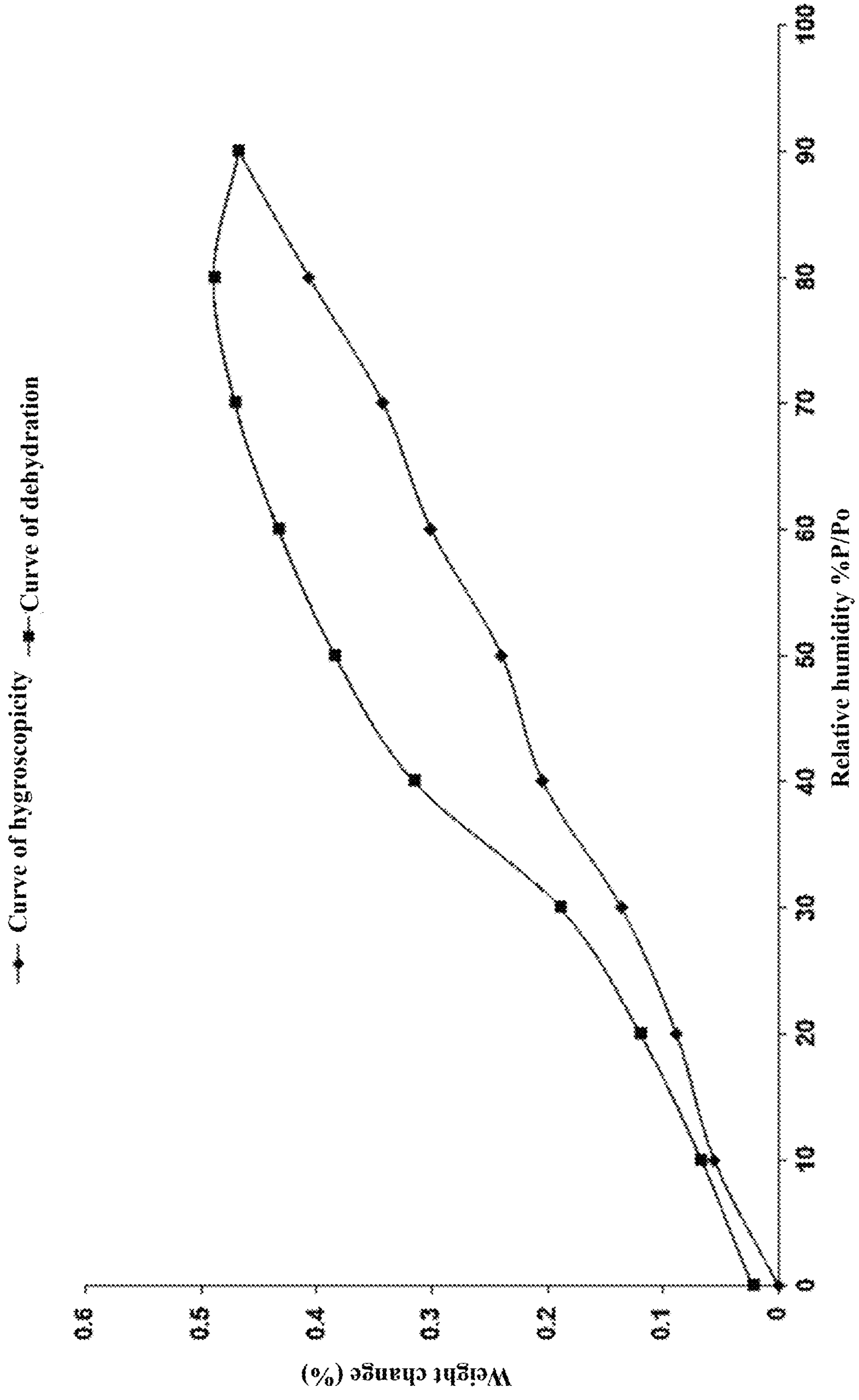
FIG. 18 is a DVS (dynamic vapor sorption) plot of the crystalline form B of the compound of formula (I)

Range of RH (%) test gradient: 0%-90%-0% The resulting dynamic vapor sorption (DVS) plot is shown in FIG. 18.

As can be seen from FIG. 18, the crystalline form of the compound of formula (I) of the present application has a low hygroscopicity.

Experimental Example 1: In Vitro Detection of the Inhibitory Activity of the Compound Against PDE 3A Enzyme Objective: to determine the AMP/GMP expression based on fluorescence polarization, i.e., to trace binding of AMP/GMP to antibody so as to indicate enzyme activity.

Reagents:

Buffer solution: 10 mM Tris-HCl (pH 7.5), 5 mM $MgCl_2$, 0.01% Brij 35, 1 mM dithiothreitol (DTT), and 1% DMSO.

Enzyme: recombinant human PDE3A (Gene accession number: NM_000921; amino acid 669-end) was expressed by baculovirus in Sf9 insect cells using an N-terminal GST tag, with the molecular weight being 84 kDa.

Enzyme substrate: 1 μM cAMP

Detection: Transcreener®AMP2/GMP2 antibody and AMP2/GMP2 AlexaFluor633 tracer.

Procedures:

1. The recombinant human PDE3A enzyme and enzyme substrate (1 μM cAMP) were each dissolved in newly prepared experimental buffer solution;
2. The PDE3A enzyme buffer solution was transferred into reaction wells;
3. The compound which was dissolved in 100% DMSO was added to the reaction wells containing PDE3A enzyme buffer solution by acoustic technique (echo 550; millilambda range) and the mixture was incubated for 10 min at room temperature;
4. The enzyme substrate buffer solution was added to the above reaction wells to initiate the reaction;
5. The resulting mixture was incubated at room temperature for 1 h;
6. The detection mixture (Transcreener®AMP2/GMP2 antibody and AMP2/GMP2 AlexaFluor633 tracer) was added to stop the reaction, and the resulting mixture was incubated for 90 min while slowly mixing. The measurement range of fluorescence polarization was Ex/Em=620/688.

Data analysis: the fluorescence polarization signal was converted to nM based on AMP/GMP standard curve and the percentage enzyme activity relative to DMSO control calculated by Excel. GraphPad Prism was used for curve fitting (drawing medical icon). The results are shown in Table 10.

Experimental Example 2: In Vitro Detection of the Inhibitory Activity of the Compound Against PDE4B Enzyme Objective: to determine the AMP/GMP expression based on fluorescence polarization, i.e., to trace binding of AMP/GMP to antibody so as to indicate enzyme activity.

Reagents:

Buffer solution: 10 mM Tris-HCl (pH 7.5), 5 mM $MgCl_2$, 0.01% Brij 35, 1 mM DTT, and 1% DMSO.

Enzyme: recombinant human PDE4B (Gene accession number: NM_002600; amino acid 305-end) was expressed by baculovirus in Sf9 insect cells using an N-terminal GST tag, with the molecular weight being 78 kDa.

Enzyme substrate: 1 μM cAMP

Detection: Transcreener®AMP2/GMP2 antibody and AMP2/GMP2 AlexaFluor633 tracer.

Procedures:

1. The recombinant human PDE4B enzyme and enzyme substrate (1 μM cAMP) were each dissolved in newly prepared buffer solution;
2. The PDE4B enzyme buffer solution was transferred into reaction wells;
3. The compound which was dissolved in 100% DMSO by acoustic technique (echo 550; millilambda range) was added to the reaction wells containing PDE4B enzyme buffer solution and the mixture was incubated for 10 minutes at room temperature;
4. The enzyme substrate buffer solution was added to the above reaction wells to initiate the reaction;
5. The resulting mixture was incubated at room temperature for 1 h;
6. The detection mixture (Transcreener®AMP2/GMP2 antibody and AMP2/GMP2 AlexaFluor633 tracer) was added to stop the reaction, and the resulting mixture was incubated for 90 min while slowly mixing. The measurement range of fluorescence polarization was Ex/Em=620/688.

Data analysis: the fluorescence polarization signal was converted to nM based on AMP/GMP standard curve and the percentage enzyme activity relative to DMSO control calculated by Excel. GraphPad Prism was used for curve fitting (drawing medical icon). The results are shown in Table 10:

TABLE 10

Results of in vitro screening test for the compound

| Compound | PDE3A $IC_{50}$(nM) | PDE4B $IC_{50}$(nM) |
|---|---|---|
| Compound of formula (I) | 0.03 | 0.41 |

The compound of the present application has significant dual inhibitory effect on PDE3 and PDE4.

Experimental Example 3: Pharmacokinetic Study in Beagle Dogs

In this study, male beagle dogs were selected as test animals, and LC-MS/MS was used for quantitatively measuring the drug concentration in plasma of beagle dogs at different time points after intravenous injection or intragastric administration of the compound of formula (I) so as to evaluate the pharmacokinetics of the compound of formula (I) in beagle dogs.

The clear solution of the compound of formula (I) was injected into two beagle dogs of 10-12 kg via the cephalic vein or saphenous vein, and the clear solution of the compound of formula (I) was administered intragastrically to two beagle dogs of 10-12 kg (fasted overnight). The animals were all subjected to a blood collection of approximately 500 μL each time from peripheral veins at 0.0333, 0.0833, 0.25, 0.5, 1, 2, 4, 6, 8 and 24 h post-dose, and the blood was transferred into commercial centrifuge tubes containing 0.85-1.15 mg of $K_2$ EDTA·$2H_2O$ anticoagulant, and plasma was separated by centrifugation at 3000 g for 10 min at 4° C. The plasma concentration was measured by LC-MS/MS, and the relevant pharmacokinetic parameters were calculated using pharmacokinetic software WinNonlin™ Version 6.3 (Pharsight, Mountain View, CA) using non-compartmental model linear-log trapezoidal method.

TABLE 11

| Pharmacokinetic parameters of the compound in beagle dogs | | | | | | | |
|---|---|---|---|---|---|---|---|
| Pharma- | Intravenous injection (0.5 mg/kg) | | | Intragastric administration (3 mg/kg) | | | |
| cokinetics in beagle dogs | Plasma clearance (mL/ min/kg) | Half-life (h) | Area under plasma concentration-time curve (0-inf, nM · h) | Peak concentration (nM) | Time to peak (h) | Area under plasma concentration-time curve (0-inf, nM · h) | Bio-availability (%) |
| Compound of formula (I) | 70.3 | 0.3 | 210 | 59.4 | 0.6 | 123 | 7.5 |

The compound of the present application has high in vivo plasma clearance, low systemic exposure in plasma by oral administration and low oral bioavailability.

Experimental Example 4: Inhibitory Effect on Activity of Isoenzymes (CYP1A2, CYP2C9, CYP2C19, CYP2D6 and CYP3A4) of Human Liver Microsomal Cytochrome P450

A total of 5 specific probe substrates of 5 isoenzymes of CYP, i.e., phenacetin (CYP1A2), diclofenac (CYP2C9), (S)-mephenytoin (CYP2C19), dextromethorphan (CYP2D6) and midazolam (CYP3A4) were each co-incubated with human liver microsomes and the compound of formula (I), and then reduced nicotinamide adenine dinucleotide phosphate (NADPH) was added to initiate the reaction. After the reaction was completed, the samples were treated, and the concentrations of 5 metabolites (acetaminophen, 4'-hydroxydiclofenac, 4'-hydroxymephenytoin, dextrorphan and 1'-hydroxymidazolam) generated from the specific substrates were quantitatively detected by LC-MS/MS to calculate the corresponding half maximal inhibitory concentrations ($IC_{50}$).

TABLE 12

| Inhibitory effect of compound of formula (I) on five CYP enzymes | | | | | |
|---|---|---|---|---|---|
| | $IC_{50}$ (μM) | | | | |
| Compound No. | CYP1A2 | CYP2C9 | CYP2C19 | CYP2D6 | CYP3A4 |
| Compound of formula (I) | 50 | 31 | 50 | 50 | 50 |

The compound of the present application has low inhibitory effect on the 5 isoenzymes (CYP1A2, CYP2C9, CYP2C19, CYP2D6 and CYP3A4) of human liver microsomal cytochrome P450.

Experimental Example 5: Pharmacodynamic Study in Cigarette Smoke-Induced Rat Acute Lung Injury Model Animals Male Sprague-Dawley rats (supplied by Shanghai SLAC Laboratory Animal Co., Ltd.), SPF grade, approximately 200 g.

Procedures

1. Animals were randomly divided into 6 groups according to body weight after arrival and a one-week acclimation;
2. On days 1-3 of the experiment, the corresponding compound of each group was atomized for 30 min. The animals in the model group and the treatment groups were exposed to cigarette smoke for 1 h, and after a 4-h interval, the animals were exposed to cigarette smoke again for 1 h. Cigarette smoke was given twice daily for 3 consecutive days. The control group animals were exposed to room air;
3. On day 4 of the experiment, the corresponding compound of each group was atomized for 30 min, and then the animals in the model group and the treatment groups were given the atomized 150 ng/mL LPS for 15 min by inhalation. After 3 h (from the time starting atomization), the animals were exposed to cigarette smoke for 1 h, and then the lung function (Penh and F) of the animals was examined; bronchoalveolar lavage fluid was collected for cell counting after the animals were euthanized with $CO_2$.
4. Administration Administration mode: the test compound and reference compound were given by atomization at the maximum atomization rate (approximately 12 mL) with the whole-body exposure atomization device for 30 min.

Administration frequency: the drug or solvent were given by atomization for 30 min in every morning before exposure to cigarette smoke, and were given before the inhalation of the atomized LPS on day 4.

5. Measurements of Pharmacodynamic Endpoints
   (1) Total white blood cells in BALF (bronchoalveolar lavage fluid);
   (2) Mch challenge pulmonary function test (airway resistance index Penh);

TABLE 13

| Grouping | | | |
|---|---|---|---|
| Group | Number of animals | Compound concentration in solution for atomization | Time of administration |
| Model group | 10 | — | 30 min before the first cigarette smoke exposure every day |
| Low dose group of the compound of formula (I) | 10 | 0.05 mg/ml | 30 min before the first cigarette smoke exposure every day |
| High dose group of the compound of formula (I) | 10 | 0.15 mg/ml | 30 min before the first cigarette smoke exposure every day |

Figure 19:
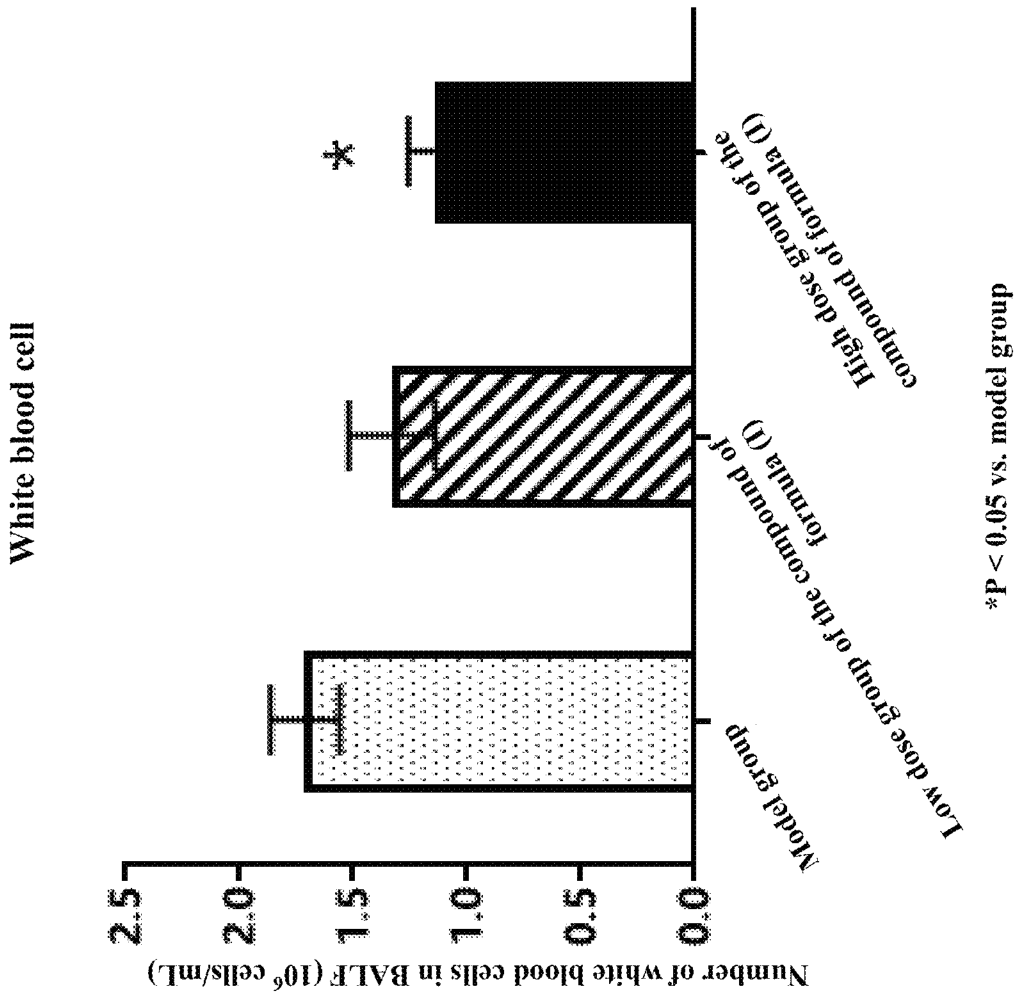
FIG. 19 shows the total number of white blood cells in BALF.
Figure 20:
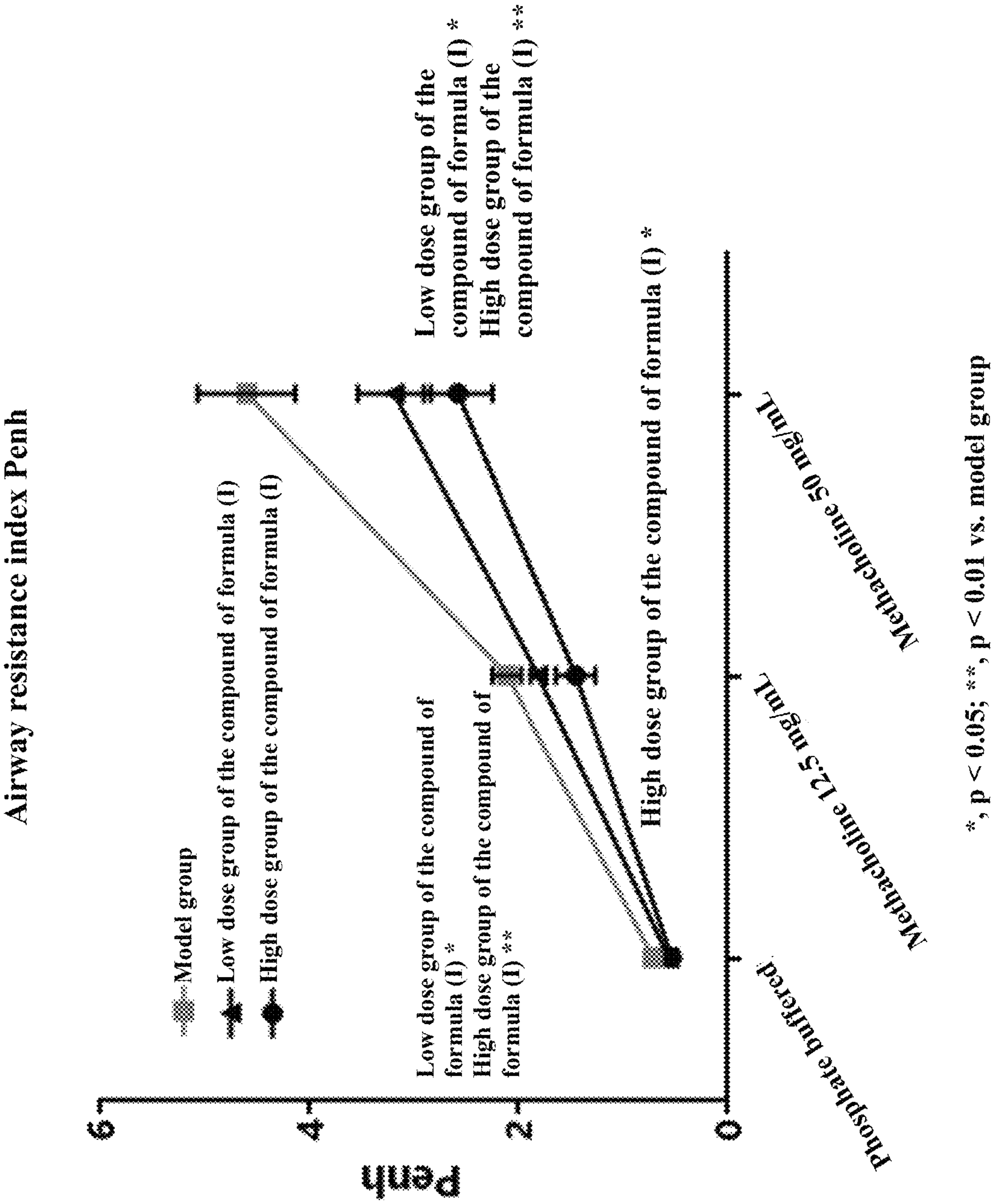
FIG. 20 shows the methacholine (Mch) challenge pulmonary function test (airway resistance index Penh).

The results are shown in FIG. 19 and FIG. 20.

The compound of the present application can reduce the total number of white blood cells in BALF and the airway resistance index Penh in a cigarette smoke-induced rat acute lung injury model.

Experimental Example 6: In Vitro Detection of the Inhibitory Activity of the Compound Against TNF-α in Human Peripheral Blood Mononuclear Cells Objective: to measure the anti-inflammatory activity at cellular level of the test compound based on the level of TNF-α in human peripheral blood mononuclear cells (hPBMCs).

Procedures:

1. Normal human whole blood was collected into an EDTA anticoagulation tube;
2. The PBMCs were separated by Ficoll density gradient centrifugation, and then counted, and the cell concentration was adjusted to $2\times10^6$/mL;
3. To each well of a U-bottom 96-well plate were added $2\times10^5$ cells, 1 ng/mL LPS, and solutions of the compound of formula (I) in DMSO at concentrations of 100 μM, 10 μM, 1 μM, 100 nM, 10 nM, 1 nM, 100 pM and 10 pM, with a system volume of 200 μL per well;
4. The mixture was incubated for 24 h, and then the supernatant was collected;
5. The level of TNF-α in the supernatant was detected by ELISA, an inhibition curve was fitted using Graphpad Prism software, and the $IC_{50}$ was calculated.

The results are shown in Table 14:

TABLE 14

Results of in vitro test for the compound

| Compound | hPBMC $IC_{50}$(nM) |
|---|---|
| Compound of formula (I) | 29.18 |

The compound of the present application has significant inhibitory effect on TNF-α in human peripheral blood mononuclear cells (hPBMCs).

The invention claimed is:

1. A crystalline form of a compound of formula (I) or a pharmaceutically acceptable salt thereof, wherein the pharmaceutically acceptable salt is sulfate, p-toluenesulfonate, methanesulfonate or maleate:

(I)

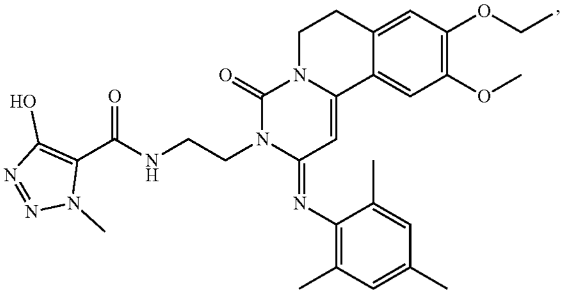

wherein the crystalline form of the compound of formula (I) is one of the following crystalline forms:

(1) a crystalline form comprising 4, 5, 6, 7 or 8 diffraction peaks in an X-ray powder diffraction (XRPD) pattern using Cu Kα radiation selected from the following 2θ angles: 4.14±0.2°, 6.56±0.2°, 6.98±0.2°, 8.20±0.2°, 11.50±0.2°, 12.66±0.2°, 13.94±0.2° and 16.35±0.2°;

(2) a crystalline form comprising 5, 6, 7, 8, 9, 10 or 11 diffraction peaks in an X-ray powder diffraction pattern using Cu Kα radiation selected from the following 2θ angles: 5.81±0.2°, 8.38±0.2°, 11.16±0.2°, 13.96±0.2°, 14.47±0.2°, 15.01±0.2°, 16.76±0.2°, 17.95±0.2°, 20.83±0.2°, 24.73±0.2° and 26.13±0.2°; or (3) a crystalline form comprising 4, 5, 6, 7, 8 or 9 diffraction peaks in an X-ray powder diffraction pattern using Cu Kα radiation selected from the following 2θ angles: 4.57±0.2°, 6.41±0.2°, 7.18±0.2°, 11.58±0.2°, 12.84±0.2°, 13.21±0.2°, 14.34±0.2°, 16.05±0.2° and 23.41±0.2°;

and wherein the crystalline form of the pharmaceutically acceptable salt is one of the following crystalline forms:

(i) a crystalline form of the compound of formula (II)

(II)

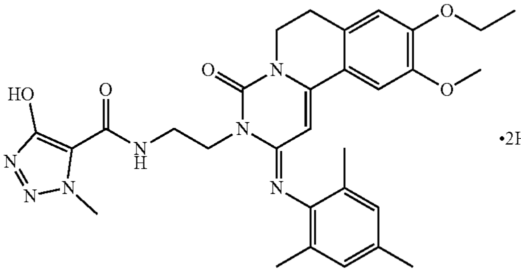

$\cdot 2H_2SO_4$ comprising 4, 5, 6, 7 or 8 diffraction peaks in an X-ray powder diffraction pattern using Cu Kα radiation selected from the following 2θ angles: 4.84±0.2°, 9.58±0.2°, 10.93±0.2°, 11.97±0.2°, 14.31±0.2°, 14.75±0.2°, 16.49±0.2° and 24.42±0.2°;

(ii) a crystalline form of the compound of formula (III)

(III)

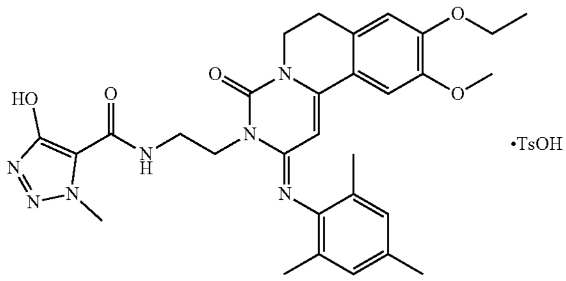

•TsOH comprising 3, 4, 5 or 6 diffraction peaks in an X-ray powder diffraction pattern using Cu Kα radiation selected from the following 2θ angles: 6.53±0.2°, 10.87±0.2°, 12.48±0.2°, 13.11±0.2°, 16.58±0.2° and 25.03±0.2°;

(iii) a crystalline form of the compound of formula (IV)

(IV)

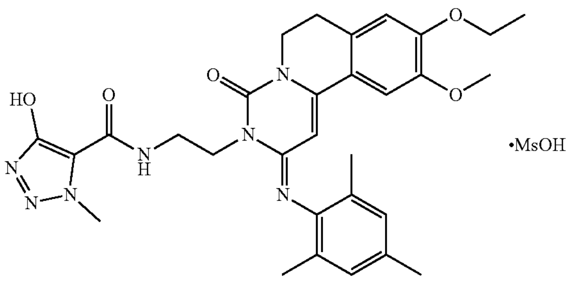

comprising 4, 5, 6, 7 or 8 diffraction peaks in an X-ray powder diffraction pattern using Cu Kα radiation selected from the following 2θ angles: 11.22±0.2°, 12.58±0.2°, 16.43±0.2°, 17.90±0.2°, 18.85±0.2°, 22.62±0.2°, 24.45±0.2° and 25.87±0.2°; or (iv) a crystalline form of the compound of formula (V)

(V)

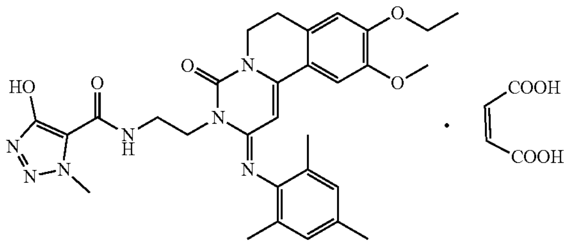

comprising 4, 5, 6, 7 or 8 diffraction peaks in an X-ray powder diffraction pattern using Cu Kα radiation selected from the following 2θ angles: 5.83±0.2°, 6.62±0.2°, 9.50±0.2°, 10.98±0.2°, 17.16±0.2°, 19.05±0.2°, 24.71±0.2° and 25.16±0.2°.

2. The crystalline form of the compound of formula (I) or the pharmaceutically acceptable salt thereof according to claim 1, wherein the crystalline form is a crystalline form of the compound of formula (I) having diffraction peaks in an X-ray powder diffraction pattern using Cu Kα radiation at the following 2θ angles: 4.14±0.2°, 6.98±0.2°, 8.20±0.2° and 11.50±0.2°; or having diffraction peaks at the following 2θ angles: 4.14±0.2°, 6.56±0.2°, 6.98±0.2°, 8.20±0.2°, 11.50±0.2°, 12.66±0.2°, 13.94±0.2° and 16.35±0.2°; or having diffraction peaks at the following 2θ angles: 4.14±0.2°, 6.56±0.2°, 6.98±0.2°, 8.20±0.2°, 9.35±0.2°, 11.50±0.2°, 12.66±0.2°, 13.94±0.2°, 14.52±0.2°, 16.35±0.2°, 21.52±0.2° and 24.57±0.2°; or the crystalline form is a crystalline form of the compound of formula (I) having an XRPD pattern using Cu Kα radiation as shown in FIG. 1.

3. The crystalline form of the compound of formula (I) or the pharmaceutically acceptable salt thereof according to claim 2, wherein the crystalline form is a crystalline form of the compound of formula (I) having endothermic peaks in a differential scanning calorimetry curve at 146.23±2° C. and/or 162.19±2° C.; or having exothermic peaks in a differential scanning calorimetry curve at 172.65±2° C. and/or 241.73±2° C.

4. The crystalline form of the compound of formula (I) or the pharmaceutically acceptable salt thereof according to claim 1, wherein the crystalline form is a crystalline form of the compound of formula (I) having diffraction peaks in an X-ray powder diffraction pattern using Cu Kα radiation at the following 2θ angles: 5.81±0.2°, 13.96±0.2°, 15.01±0.2°, 17.95±0.2° and 24.73±0.2°; or having diffraction peaks at the following 2θ angles: 5.81±0.2°, 8.38±0.2°, 11.16±0.2°, 13.96±0.2°, 14.47±0.2°, 15.01±0.2°, 16.76±0.2°, 17.95±0.2°, 20.83±0.2°, 24.73±0.2° and 26.13±0.2°; or having diffraction peaks at the following 2θ angles: 5.81±0.2°, 8.38±0.2°, 9.13±0.2°, 11.16±0.2°, 11.60±0.2°, 12.82±0.2°, 13.96±0.2°, 14.47±0.2°, 15.01±0.2°, 16.76±0.2°, 17.95±0.2°, 18.91±0.2°, 20.83±0.2°, 24.36±0.2°, 24.73±0.2°, 25.78±0.2° and 26.13±0.2°; or the crystalline form is a crystalline form of the compound of formula (I) having an XRPD pattern using Cu Kα radiation as shown in FIG. 4.

5. The crystalline form of the compound of formula (I) or the pharmaceutically acceptable salt thereof according to claim 4, wherein the crystalline form is a crystalline form of the compound of formula (I) having an exothermic peak in a differential scanning calorimetry curve at 247.70±2° C.

6. The crystalline form of the compound of formula (I) or the pharmaceutically acceptable salt thereof according to claim 1, wherein the crystalline form is a crystalline form of the compound of formula (I) having diffraction peaks in an X-ray powder diffraction pattern using Cu Kα radiation at the following 2θ angles: 4.57±0.2°, 6.41±0.2°, 7.18±0.2° and 14.34±0.2°; or having diffraction peaks at the following 2θ angles: 4.57±0.2°, 6.41±0.2°, 7.18±0.2°, 11.58±0.2°, 12.84±0.2°, 13.21±0.2°, 14.34±0.2°, 16.05±0.2° and 23.41±0.2°; or having diffraction peaks at the following 2θ angles: 4.57±0.2°, 6.41±0.2°, 7.18±0.2°, 9.07±0.2°, 11.58±0.2°, 12.84±0.2°, 13.21±0.2°, 14.34±0.2°, 16.05±0.2°, 18.15±0.2°, 19.26±0.2°, 20.85±0.2° and 23.41±0.2°; or the crystalline form is a crystalline form of the compound of formula (I) having an XRPD pattern using Cu Kα radiation as shown in FIG. 7.

7. The crystalline form of the compound of formula (I) or the pharmaceutically acceptable salt thereof according to claim 6, wherein the crystalline form is a crystalline form of the compound of formula (I) having exothermic peaks in a differential scanning calorimetry curve at 152.26±2° C. and/or 247.92±2° C.

8. The crystalline form of the compound of formula (I) or the pharmaceutically acceptable salt thereof according to claim 1, wherein the crystalline form is a crystalline form of the compound of formula (II) having diffraction peaks in an X-ray powder diffraction pattern using Cu Kα radiation at the following 2θ angles: 4.84±0.2°, 9.58±0.2°, 11.97±0.2° and 14.75±0.2°; or having diffraction peaks at the following 2θ angles: 4.84±0.2°, 9.58±0.2°, 10.93±0.2°, 11.97±0.2°, 14.31±0.2°, 14.75±0.2°, 16.49±0.2° and 24.42±0.2°; or having diffraction peaks at the following 2θ angles: 4.84±0.2°, 9.58±0.2°, 10.93±0.2°, 11.97±0.2°, 12.72±0.2°, 13.93±0.2°, 14.31±0.2°, 14.75±0.2°, 16.49±0.2°, 17.91±0.2°, 19.25±0.2°, 19.90±0.2°, 20.57±0.2°, 24.42±0.2° and 25.70±0.2°; or the crystalline form is a crystalline form of the compound of formula (II) having an XRPD pattern using Cu Kα radiation as shown in FIG. 10.

9. The crystalline form of the compound of formula (I) or the pharmaceutically acceptable salt thereof according to claim 1, wherein the crystalline form is a crystalline form of the compound of formula (III) having diffraction peaks in an X-ray powder diffraction pattern using Cu Kα radiation at the following 2θ angles: 6.53±0.2°, 12.48±0.2° and 13.11±0.2°; or having diffraction peaks at the following 2θ angles: 6.53±0.2°, 10.87±0.2°, 12.48±0.2°, 13.11±0.2°, 16.58±0.2° and 25.03±0.2°; or having diffraction peaks at the following 2θ angles: 6.53±0.2°, 10.87±0.2°, 12.48±0.2°, 13.11±0.2°, 14.04±0.2°, 16.58±0.2°, 25.03±0.2°, 25.56±0.2° and 26.66±0.2°; or the crystalline form is a crystalline form of the compound of formula (III) having an XRPD pattern using Cu Kα radiation as shown in FIG. 11.

10. The crystalline form of the compound of formula (I) or the pharmaceutically acceptable salt thereof according to claim 1, wherein the crystalline form is a crystalline form of the compound of formula (IV) having diffraction peaks in an X-ray powder diffraction pattern using Cu Kα radiation at the following 2θ angles: 11.22±0.2°, 18.85±0.2°, 22.62±0.2° and 24.45±0.2°; or having diffraction peaks at the following 2θ angles: 11.22±0.2°, 12.58±0.2°, 16.43±0.2°, 17.90±0.2°, 18.85±0.2°, 22.62±0.2°, 24.45±0.2° and 25.87±0.2°; or having diffraction peaks at the following 2θ angles: 11.22±0.2°, 12.58±0.2°, 16.43±0.2°, 17.08±0.2°, 17.90±0.2°, 18.85±0.2°, 19.23±0.2°, 19.72±0.2°, 22.62±0.2°, 23.27±0.2°, 24.45±0.2° and 25.87±0.2°; or having diffraction peaks at the following 2θ angles: 11.22±0.2°, 12.58±0.2°, 13.88±0.2°, 15.49±0.2°, 16.04±0.2°, 16.43±0.2°, 17.08±0.2°, 17.90±0.2°, 18.54±0.2°, 18.85±0.2°, 19.23±0.2°, 19.72±0.2°, 20.02±0.2°, 20.51±0.2°, 22.62±0.2°, 23.27±0.2°, 24.45±0.2°, 24.83±0.2°, 25.42±0.2°, 25.87±0.2°, 26.09±0.2° and 29.53±0.2°; or the crystalline form is a crystalline form of the compound of formula (IV) having an XRPD pattern using Cu Kα radiation as shown in FIG. 13.

11. The crystalline form of the compound of formula (I) or the pharmaceutically acceptable salt thereof according to claim 10, wherein the crystalline form is a crystalline form of the compound of formula (IV) having an endothermic peak at 191.35±2° C. and/or an exothermic peak at 222.21±2° C. in a differential scanning calorimetry curve.

12. The crystalline form of the compound of formula (I) or the pharmaceutically acceptable salt thereof according to claim 1, wherein the crystalline form is a crystalline form of the compound of formula (V) having diffraction peaks in an X-ray powder diffraction pattern using Cu Kα radiation at the following 2θ angles: 5.83±0.2°, 6.62±0.2°, 9.50±0.2° and 10.98±0.2°; or having diffraction peaks at the following 2θ angles: 5.83±0.2°, 6.62±0.2°, 9.50±0.2°, 10.98±0.2°, 17.16±0.2°, 19.05±0.2°, 24.71±0.2° and 25.16±0.2°; or having diffraction peaks at the following 2θ angles: 5.83±0.2°, 6.62±0.2°, 9.50±0.2°, 10.98±0.2°, 11.59±0.2°, 13.23±0.2°, 16.27±0.2°, 17.16±0.2°, 19.05±0.2°, 21.63±0.2°, 24.71±0.2° and 25.16±0.2°; or the crystalline form is a crystalline form of the compound of formula (V) having an XRPD pattern using Cu Kα radiation as shown in FIG. 16.

13. The crystalline form of the compound of formula (I) or the pharmaceutically acceptable salt thereof according to claim 1, wherein the crystalline form is in the form of a crystalline composition comprising the crystalline form of the compound of formula (I) or the pharmaceutically acceptable salt thereof, wherein the crystalline form accounts for 50% or more of the weight of the crystalline composition.

14. A pharmaceutical composition, comprising a therapeutically effective amount of the crystalline form of the compound of formula (I) or the pharmaceutically acceptable salt thereof according to claim 1.

15. A method for preparing a compound of formula (I), comprising: preparing the compound of formula (I) by method 1 or method 2; wherein the method 1 comprises: (1) reacting compound 1-2a to give compound BB-4; and (2) reacting compound BB-4 with 5-hydroxy-3-methyl-1,2,3-triazole-4-carboxylic acid to give the compound of formula (I),

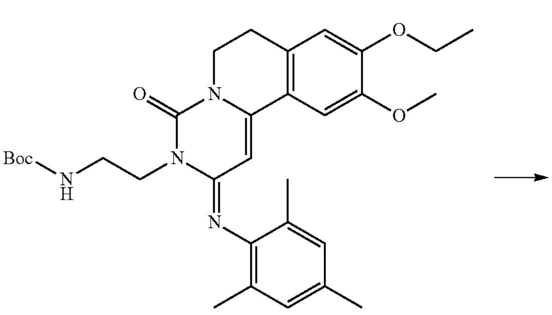

1-2a

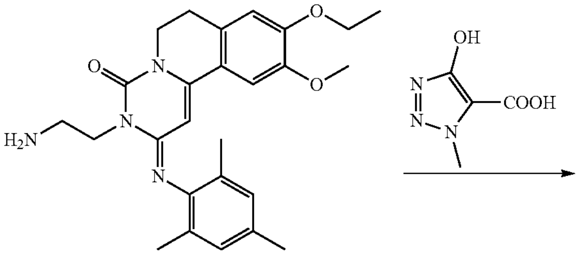

BB-4

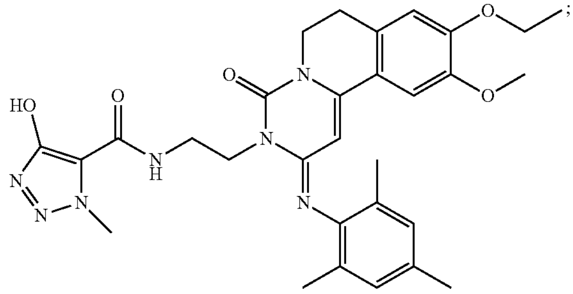

(I)

the method 2 comprises: reacting compound 1-4b to give the compound of formula (I)

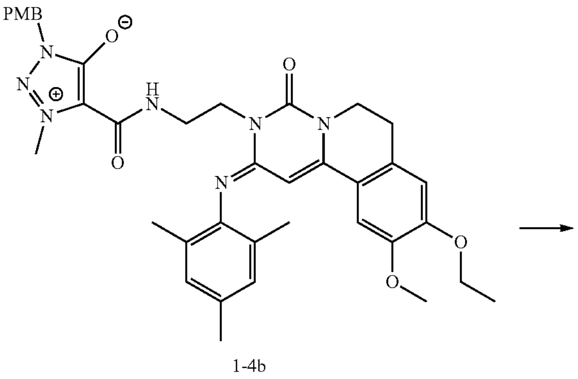

1-4b

-continued

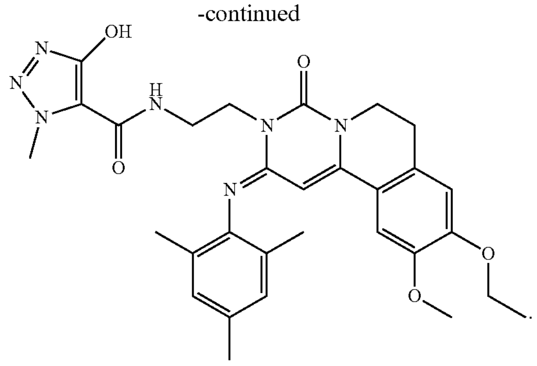

(I)

16. The method according to claim 15, wherein the compound of formula (I) is prepared by the method 1, and wherein compound 1-2a is prepared by reacting compound BB-1 with compound 1-1a,

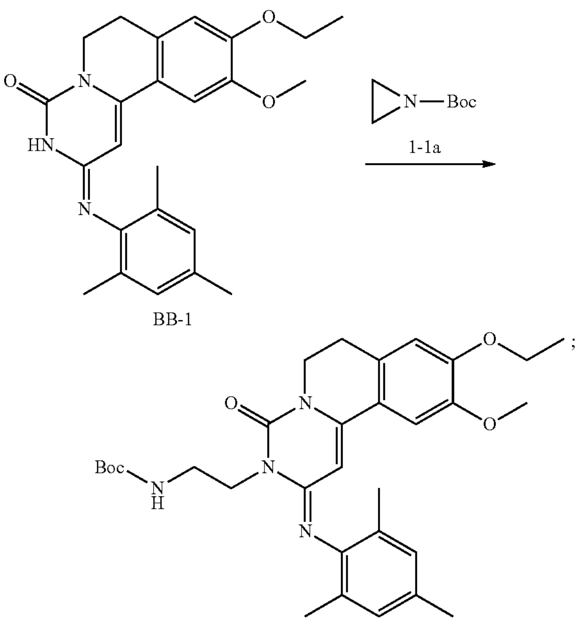

BB-1

1-2a the compound of formula (I) is prepared by the method 2, and wherein compound 1-4b is prepared by reacting compound BB-4 with compound 1-3b,

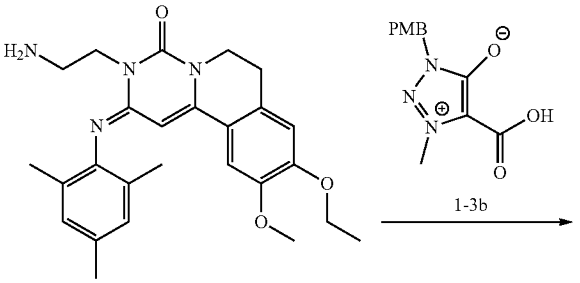

BB-4

-continued

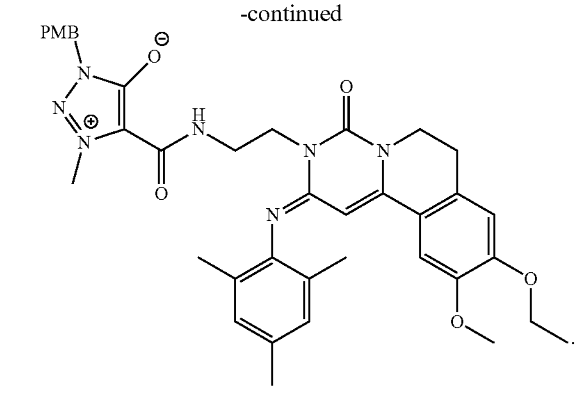

1-4b

17. The method according to claim 15, wherein compound BB-4 is prepared by reacting compound 1-1b,

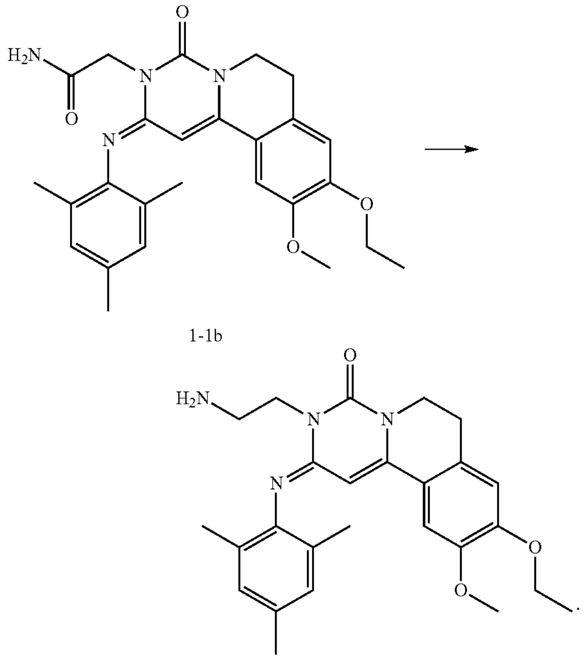

1-1b

BB-4

18. The method according to claim 17, wherein compound 1-1b is prepared by reacting compound BB-1 with compound a

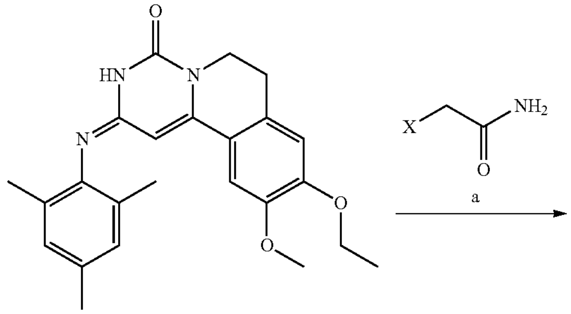

BB-1

-continued

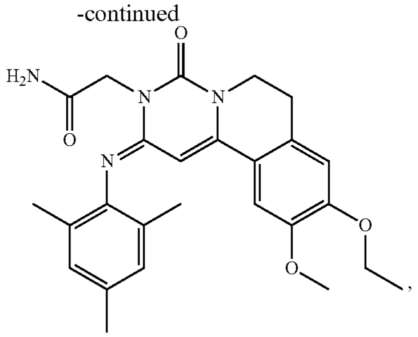

1-1b wherein X is a halogen.

19. A method for treating a condition associated with PDE3 and/or PDE4 in a mammal, comprising administering to a mammal in need thereof a therapeutically effective amount of the crystalline form of the compound of formula (I) or the pharmaceutically acceptable salt thereof according to claim 1, or a crystalline composition or a pharmaceutical composition comprising the crystalline form.

20. The method according to claim 19, wherein treating the condition associated with PDE3 and/or PDE4 is selected from anti-inflammatory action and bronchodilation; or selected from the treatment of asthma and chronic obstructive pulmonary disease.

* * * * *